(12) United States Patent
Hartley et al.

(10) Patent No.: US 7,282,326 B2
(45) Date of Patent: Oct. 16, 2007

(54) RECOMBINATIONAL CLONING USING ENGINEERED RECOMBINATION SITES

(75) Inventors: James L. Hartley, Frederick, MD (US); Michael A. Brasch, Gaithersburg, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 10/058,292

(22) Filed: Jan. 30, 2002

(65) Prior Publication Data

US 2003/0054552 A1 Mar. 20, 2003

Related U.S. Application Data

(60) Continuation of application No. 09/432,085, filed on Nov. 2, 1999, which is a division of application No. 09/233,493, filed on Jan. 20, 1999, now Pat. No. 6,143,557, which is a continuation of application No. 08/663,002, filed on Jun. 7, 1996, now Pat. No. 5,888,732, which is a continuation-in-part of application No. 08/486,139, filed on Jun. 7, 1995, now abandoned.

(51) Int. Cl.
*C12Q 1/68* (2006.01)
*C12N 15/10* (2006.01)
*C12N 15/31* (2006.01)
*C12N 15/63* (2006.01)
*C12N 15/64* (2006.01)
*C12P 21/00* (2006.01)
*C07H 21/04* (2006.01)

(52) U.S. Cl. .......... 435/6; 435/455; 435/69.1; 435/91.4; 435/91.5; 435/320.1

(58) Field of Classification Search ............ None
See application file for complete search history.

(56) References Cited

U.S. PATENT DOCUMENTS

| | | | |
|---|---|---|---|
| 4,626,505 A | 12/1986 | Falco | |
| 4,673,640 A | 6/1987 | Backman | |
| 4,683,195 A | 7/1987 | Mullis et al. | |
| 4,683,202 A | 7/1987 | Mullis | |
| 4,743,546 A | 5/1988 | Backman et al. | |
| 4,808,537 A | 2/1989 | Stroman et al. | |
| 4,855,231 A | 8/1989 | Stroman et al. | |
| 4,959,217 A | 9/1990 | Sanders et al. | |
| 4,959,317 A | 9/1990 | Sauer | |
| 4,965,188 A | 10/1990 | Mullis et al. | |
| 5,093,257 A | 3/1992 | Gray | |
| 5,102,797 A | 4/1992 | Tucker et al. | |
| 5,159,062 A * | 10/1992 | Knapp et al. | 530/350 |
| 5,227,288 A | 7/1993 | Blattner | |
| 5,286,632 A | 2/1994 | Jones | |
| 5,334,375 A | 8/1994 | Nabi et al. | |
| 5,334,575 A | 8/1994 | Noonan et al. | |
| 5,348,886 A | 9/1994 | Lee et al. | |
| 5,354,668 A | 10/1994 | Auerbach | |
| 5,378,618 A | 1/1995 | Sternberg et al. | |
| 5,434,066 A | 7/1995 | Bebee et al. | |
| 5,451,513 A | 9/1995 | Maliga et al. | |
| 5,470,727 A | 11/1995 | Mascarenhas et al. | |
| 5,527,695 A * | 6/1996 | Hodges et al. | 435/455 |
| 5,552,314 A | 9/1996 | Greener | |
| 5,591,609 A | 1/1997 | Auerbach | |
| 5,605,793 A | 2/1997 | Stemmer | |
| 5,614,389 A | 3/1997 | Auerbach | |
| 5,635,381 A | 6/1997 | Hooykaas et al. | |
| 5,650,308 A | 7/1997 | Baum | |
| 5,650,557 A | 7/1997 | Hannah et al. | |
| 5,654,182 A | 8/1997 | Wahl et al. | |
| 5,658,772 A | 8/1997 | Odell et al. | |
| 5,677,170 A | 10/1997 | Devine et al. | |
| 5,677,177 A * | 10/1997 | Wahl et al. | 435/325 |
| 5,695,971 A | 12/1997 | Kadokami et al. | |
| 5,710,248 A | 1/1998 | Grose | |
| 5,723,765 A | 3/1998 | Oliver et al. | |
| 5,728,551 A | 3/1998 | Devine et al. | |
| 5,733,733 A | 3/1998 | Auerbach | |
| 5,733,743 A | 3/1998 | Johnson et al. | |
| 5,744,336 A | 4/1998 | Hodges et al. | |
| 5,766,891 A | 6/1998 | Shuman | |
| 5,776,449 A | 7/1998 | Baum et al. | |
| 5,801,030 A | 9/1998 | McVey et al. | |
| 5,814,300 A | 9/1998 | Scott et al. | |
| 5,830,707 A | 11/1998 | Bushman | |
| 5,837,242 A | 11/1998 | Holliger et al. | |
| 5,837,458 A | 11/1998 | Minshull et al. | |
| 5,843,772 A | 12/1998 | Devine et al. | |

(Continued)

FOREIGN PATENT DOCUMENTS

CA 2141412 2/1994

(Continued)

OTHER PUBLICATIONS

Abremski e tal. J. Biol. Chem. 1984; 259:1509-14.*

(Continued)

*Primary Examiner*—David Guzo

(57) ABSTRACT

Recombinational cloning is provided by the use of nucleic acids, vectors and methods, in vitro and in vivo, for moving or exchanging segments of DNA molecules using engineered recombination sites and recombination proteins to provide chimeric DNA molecules that have the desired characteristic(s) and/or DNA segment(s).

32 Claims, 44 Drawing Sheets

U.S. PATENT DOCUMENTS

| | | | |
|---|---|---|---|
| 5,851,808 A | 12/1998 | Elledge et al. | |
| 5,858,657 A | 1/1999 | Winter et al. | |
| 5,871,907 A | 2/1999 | Winter et al. | |
| 5,874,259 A | 2/1999 | Szybalski | |
| 5,888,732 A | 3/1999 | Hartley et al. | |
| 5,910,438 A | 6/1999 | Bernard et al. | |
| 5,916,804 A | 6/1999 | Bushman | |
| 5,919,676 A | 7/1999 | Graham et al. | |
| 5,928,914 A | 7/1999 | Leboulch et al. | |
| 5,929,307 A | 7/1999 | Hodges et al. | |
| 5,962,255 A | 10/1999 | Griffiths et al. | |
| 5,981,177 A * | 11/1999 | Demirjian et al. | 435/6 |
| 5,989,872 A | 11/1999 | Luo et al. | |
| 6,010,884 A | 1/2000 | Griffiths et al. | |
| 6,040,138 A | 3/2000 | Lockhart et al. | |
| 6,040,430 A | 3/2000 | Stewart | |
| 6,063,627 A | 5/2000 | McVey et al. | |
| 6,066,778 A | 5/2000 | Ginsburg et al. | |
| 6,080,576 A | 6/2000 | Zambrowicz et al. | |
| 6,110,735 A | 8/2000 | Chartier et al. | |
| 6,120,764 A | 9/2000 | Graham et al. | |
| 6,121,043 A | 9/2000 | Cochran et al. | |
| 6,140,087 A | 10/2000 | Graham et al. | |
| 6,143,557 A | 11/2000 | Hartley et al. | |
| 6,156,497 A | 12/2000 | Kaleko | |
| 6,171,861 B1 | 1/2001 | Hartley et al. | |
| 6,225,121 B1 | 5/2001 | Savakis et al. | |
| 6,228,646 B1 | 5/2001 | Hardy | |
| 6,262,341 B1 | 7/2001 | Baszczynski et al. | |
| 6,270,969 B1 | 8/2001 | Hartley et al. | |
| 6,271,436 B1 | 8/2001 | Piedrahita et al. | |
| 6,277,608 B1 | 8/2001 | Hartley et al. | |
| 6,281,000 B1 | 8/2001 | Chartier et al. | |
| 6,303,301 B1 | 10/2001 | Mack | |
| 6,309,822 B1 | 10/2001 | Fodor et al. | |
| 6,333,155 B1 | 12/2001 | Lockhart et al. | |
| 6,361,972 B1 | 3/2002 | Harrington et al. | |
| 6,365,377 B1 | 4/2002 | Patten et al. | |
| 6,410,266 B1 | 6/2002 | Harrington et al. | |
| 6,410,317 B1 | 6/2002 | Farmer | |
| 6,436,707 B1 | 8/2002 | Zambrowicz et al. | |
| 6,544,790 B1 | 4/2003 | Sabatini | |
| 6,720,140 B1 | 4/2004 | Hartley et al. | |
| 2002/0007051 A1 | 1/2002 | Cheo et al. | |
| 2002/0068290 A1 | 6/2002 | Yarovinsky | |
| 2002/0094574 A1 | 7/2002 | Hartley et al. | |
| 2002/0106797 A1 | 8/2002 | Miles et al. | |
| 2002/0162126 A1 | 10/2002 | Beach et al. | |
| 2002/0172997 A1 | 11/2002 | Hartley et al. | |
| 2002/0182731 A1 | 12/2002 | Ji et al. | |
| 2002/0192819 A1 | 12/2002 | Hartley et al. | |
| 2003/0022179 A1 | 1/2003 | Chesnut et al. | |
| 2003/0027289 A1 | 2/2003 | Farmer | |
| 2003/0027337 A1 | 2/2003 | Droge et al. | |
| 2003/0054552 A1 | 3/2003 | Hartley et al. | |
| 2003/0054555 A1 | 3/2003 | Farmer et al. | |
| 2003/0059900 A1 | 3/2003 | Farmer | |
| 2003/0064515 A1 | 4/2003 | Hartley et al. | |
| 2003/0068799 A1 | 4/2003 | Hartley et al. | |
| 2003/0077804 A1 | 4/2003 | Byrd et al. | |
| 2003/0100110 A1 | 5/2003 | Hartley et al. | |
| 2003/0124555 A1 | 7/2003 | Brasch et al. | |
| 2003/0135888 A1 | 7/2003 | Zhu et al. | |
| 2003/0153055 A1 | 8/2003 | Miles et al. | |
| 2003/0157662 A1 | 8/2003 | Gerard et al. | |
| 2003/0157716 A1 | 8/2003 | Hartley et al. | |
| 2003/0175772 A1 | 9/2003 | Wang | |
| 2003/0175970 A1 | 9/2003 | Hartley et al. | |
| 2003/0176644 A1 | 9/2003 | Byrd et al. | |
| 2003/0186233 A1 | 10/2003 | Chesnut et al. | |
| 2003/0220249 A1 | 11/2003 | Hackett et al. | |
| 2004/0040053 A1 | 2/2004 | Nomura et al. | |
| 2004/0053412 A1 | 3/2004 | Hartley et al. | |
| 2004/0063207 A1 | 4/2004 | Hartley et al. | |
| 2004/0132133 A1 | 7/2004 | Bennett | |
| 2004/0171156 A1 | 9/2004 | Hartley et al. | |
| 2004/0171157 A1 | 9/2004 | Hartley et al. | |
| 2004/0219516 A1 | 11/2004 | Bennett et al. | |
| 2004/0219673 A1 | 11/2004 | Hartley et al. | |
| 2004/0229229 A1 | 11/2004 | Cheo et al. | |
| 2004/0253620 A1 | 12/2004 | Leong et al. | |
| 2004/0253631 A1 | 12/2004 | Hartley et al. | |
| 2004/0265863 A1 | 12/2004 | Chesnut et al. | |
| 2005/0009091 A1 | 1/2005 | Hartley et al. | |
| 2005/0069929 A1 | 3/2005 | Chestnut et al. | |
| 2005/0095615 A1 | 5/2005 | Welch et al. | |
| 2005/0176065 A1 | 8/2005 | Hanson | |
| 2005/0181417 A1 | 8/2005 | Miles et al. | |
| 2005/0208530 A1 | 9/2005 | Chesnut et al. | |

FOREIGN PATENT DOCUMENTS

| | | | |
|---|---|---|---|
| EP | 0 160 571 A2 | 11/1985 | |
| EP | 0 220 009 | 4/1987 | |
| EP | 0 300 422 | 1/1989 | |
| EP | 0 427 074 | 5/1991 | |
| EP | 0 542 466 A2 | 5/1993 | |
| EP | 542466 * | 5/1993 | 435/456 |
| EP | 1 035 208 | 9/2000 | |
| FR | 2 670 502 | 6/1992 | |
| WO | WO90/11375 | 10/1990 | |
| WO | WO91/02801 | 3/1991 | |
| WO | WO91/09957 | 7/1991 | |
| WO | WO91/16427 | 10/1991 | |
| WO | WO92/10577 | 6/1992 | |
| WO | WO92/15694 | 9/1992 | |
| WO | WO92/20791 | 11/1992 | |
| WO | WO92/22650 | 12/1992 | |
| WO | WO93/15191 | 8/1993 | |
| WO | WO93/19172 * | 9/1993 | 435/440 |
| WO | WO 93/19172 | 9/1993 | |
| WO | WO94/03624 | 2/1994 | |
| WO | WO94/09127 | 4/1994 | |
| WO | WO94/17176 | 8/1994 | |
| WO | WO94/18333 | 8/1994 | |
| WO | WO94/20604 | 9/1994 | |
| WO | WO95/00555 | 1/1995 | |
| WO | WO96/04393 | 2/1996 | |
| WO | WO96/19497 | 6/1996 | |
| WO | WO96/23904 A1 | 8/1996 | |
| WO | WO96/30498 | 10/1996 | |
| WO | WO96/40722 | 12/1996 | |
| WO | WO96/40724 | 12/1996 | |
| WO | WO97/06265 | 2/1997 | |
| WO | WO97/09436 | 3/1997 | |
| WO | WO97/25446 | 7/1997 | |
| WO | WO97/32481 | 9/1997 | |
| WO | WO97/47758 A1 | 12/1997 | |
| WO | WO98/10086 | 3/1998 | |
| WO | WO98/38326 A1 | 9/1998 | |
| WO | WO98/53056 | 11/1998 | |
| WO | WO99/10488 | 3/1999 | |
| WO | WO99/21977 | 5/1999 | |
| WO | WO99/25851 | 5/1999 | |
| WO | WO99/55851 | 11/1999 | |
| WO | WO 00/12687 | 3/2000 | |
| WO | WO 00/29000 | 5/2000 | |
| WO | WO 00/52027 | 9/2000 | |
| WO | WO 00/52141 | 9/2000 | |
| WO | WO 00/60091 | 10/2000 | |
| WO | WO 01/05961 | 1/2001 | |
| WO | WO 01/07572 | 2/2001 | |
| WO | WO 01/11058 | 2/2001 | |
| WO | WO 01/25466 | 4/2001 | |

| | | |
|---|---|---|
| WO | WO 01/31039 | 5/2001 |
| WO | WO 01/42509 | 6/2001 |
| WO | WO 01/62892 | 8/2001 |
| WO | WO 01/68836 | 9/2001 |
| WO | WO 02/00875 | 1/2002 |
| WO | WO 02/05294 | 1/2002 |
| WO | WO 02/08391 | 1/2002 |
| WO | WO 02/16594 | 2/2002 |
| WO | WO 02/46372 | 6/2002 |
| WO | WO 02/061034 | 8/2002 |
| WO | WO 02/062957 | 8/2002 |
| WO | WO 02/086144 | 10/2002 |
| WO | WO 02/095055 | 11/2002 |
| WO | WO 03/025161 | 3/2003 |
| WO | WO 03/044207 | 5/2003 |
| WO | WO 03/103600 | 12/2003 |
| WO | WO 2004/009768 | 1/2004 |
| WO | WO 2004/013290 | 2/2004 |
| WO | WO 2005/012487 A2 | 2/2005 |
| WO | WO 2005/014796 A2 | 2/2005 |

OTHER PUBLICATIONS

Fukushige et al. PNAS. 1992; 89:7905-09.*
Senecoff et al. J. Mol. Biol. 1988; 201:405-21.*
Stedman's Online Medical Dictionary, 27th Edition, http://216.251.232.159/semdweb/internetsomd/ASP/1529936.asp, accessed Jul. 19, 2006.*
Compact Oxford English Dictionary, http://www.askoxford.com/concise_oed/invitro?view=uk, accessed Jul. 19, 2006.*
Abremski, K., and Gottesman, S., "Purification of the Bacteriophage λ *xis* Gene Product Required for λ Excisive Recombination," *J. Biol. Chem.* 257(16):9658-9662, American Society for Biochemistry and Molecular Biology, Inc. (1982).
Abremski, K., and Hoess, R., "Bacteriophage P1 Site-specific Recombination—Purification and Properties of the Cre Recombinase Protein," *J. Biol. Chem.* 259:1509-1514, American Society for Biochemistry and Molecular Biology, Inc. (1984).
Abremski, K., et al., "Bacteriophage P1 Cre-*loxP* Site-specific Recombination: Site-specific DNA Topoisomerase Activity of the Cre Recombination Protein," *J. Biol. Chem.* 261(1):391-396, American Society for Biochemistry and Molecular Biology, Inc. (1986).
Abremski, K., et al., "Studies on the Properties of P1 Site-Specific Recombination: Evidence for Topologically Unlinked Products Following Recombination," *Cell* 32:1301-1311, Cell Press (1993).
Adams, D.E., et al., "Cre-*lox* Recombination in *Escherichia coli* Cells: Mechanistic Differences from the in Vitro Reaction," *J. Mol. Biol.* 226:661-673, Academic Press, Inc. (1992).
Albert, H., et al., "Site-specific integration of DNA into wild-type and mutant *lox* sites placed in the plant genome," *Plant J.* 7:649-659 Oxford Bios Scientific Publishers And Blackwell Scientific Publications In Association With The Society For Experimental Biology (Apr. 1995).
Andrews, B.J., et al., "The FLP Recombinase of the 2μ Circle DNA of Yeast: Interaction with Its Target Sequences," *Cell* 40:795-803, Cell Press, Cambridge, MA (1985).
Andrews, B.J., et al., "Interaction of the FLP Recombinase of the *Saccharomyces cerevisiae* 2μm Plasmid with Mutated Target Sequences," *Mol. Cell. Biol.* 6:2482-2489, American Society for Microbiology, Washington, D.C. (1986).
Anton, M., and Graham, F.L., "Site-Specific Recombination Mediated by an Adenovirus Vector Expressing the Cre Recombinase Protein: a Molecular Switch for Control of Gene Expression," *J. Virol.* 69:4600-4606, American Society for Microbiology, Washington, D.C. (Aug. 1995).
Araki, H., et al., "Site-specific Recombinase, R, Encoded by Yeast Plasmid pSR1," *J. Mol. Biol.* 225:25-37, Academic Press, Inc., New York, NY (1992).
Argos, P., et al., "The integrase family of site-specific recombinases: regional similarities and global diversity," *EMBO J.* 5(2):433-440, IRL Press Limited, Oxford (1986).

Astumian, J.H. et al., "Site-specific recombination between cloned attP and attB sites from the *Haemophilus influenza* bacteriophage HP1 propagated in recombination deficient *Escherichia coli,*" *J. Bacteriol.* 171: 1747-1750, American Society for Microbiology (1989).
Atlung, T., et al., "A versatile method for integration of genes and gene fusions into the λ attachment site of *Escherichia coli,*" *Gene* 107:11-17, Elsevier (1991).
Ausubel, F.M., et al., "Maps of Plasmids pBR322 and pUC19," in *Current Protocols in Molecular Biology*, John Wiley & Sons, Inc. (Apr. 1994).
Ausubel, F.M., et al., "Mutagenesis by the Polymerase Chain reaction," in: *Current Protocols in Molecular Biology*, John Wiley & Sons, Inc. pp. 8.5.1-8.5.9 (1991).
Babineau, D. et al., "The FLP Protein of the 2-micron Plasmid of Yeast," *J. Biol. Chem.* 260:12313-12391, American Society for Biochemistry and Molecular Biology, Inc. (1985).
Balakrishnan, R., et al., "A gene cassette for adapting *Escherichia coli* strains as hosts for *att*-Int-mediated rearrangement and $p_L$ expression vectors," *Gene* 138:101-104, Elsevier (Jan. 1994).
Bayley, C.C., et al., "Exchange of gene activity in transgenic plants catalyzed by the Cre-*lox* site specific recombination system," *Plant Mol. Biol.* 18:353-361, Dordrecht Kluwer Academic (1992).
Bernard, P., and Couturier, M., "Cell Killing by the F plasmid Ccdb Protein Involves Poisoning of DNA-topoisomerase II Complexes," *J. Mol. Biol.* 226:735-745, Academic Press, Inc. (1992).
Bernard, P., et al., "Positive Selection vectors using the F plasmid *ccd*B killer gene," *Gene* 148:71-74, Elsevier Science Publishers B.V. (Oct. 1994).
Bethke, B., and Sauer, B., "Segmental genomic replacement by Cre-mediated recombination: genotoxic stress activation of the p53 promoter in single-copy transformants," *Nucl. Acids Res.* 25:2828-2834, Oxford University Press (Jul. 1997).
Betz, U.A.K., et al., "Bypass of lethality with mosaic mice generated by Cre-*loxP*-mediated recombination," *Curr. Biol.* 6:1307-1316, Current Biology Ltd. (Oct. 1996).
Bhandari, P. and Gowrishankarm J., "An *Escherichia coli* Host Strain Useful for Efficient Overproduction of Cloned Gene Products with NaC1 as the Inducer," *J. Bacteriol.* 179:4403-4406, American Society for Microbiology (Jul. 1997).
Black, L.W., "In vitro packaging into phage T4 particles and specific recircularization of phage lambda DNAs," *Gene* 46:97-101, Elsevier (1986).
Bloch, C.A., et al., "Purification of *Escherichia coli* Chromosomal Segments without Cloning," *Biochem. Biophys. Res. Comm.* 223:104-111, Academic Press, Inc. (Jun. 1996).
Bochner, B. R., et al., "Positive Selection for Loss of Tetracycline Resistance," *J. Bacteriol.* 143:926-933, American Society for Microbiology (1980).
Boyd, A. C., "Turbo cloning: a fast, efficient method for cloning PCR products and other blunt-ended DNA fragments into plasmids," *Nucl. Acids Res.* 21(4):817-821, Oxford University Press (1993).
Broach, J. R., et al., "Recombination within the Yeast Plasmid 2μ Circle is Site-Specific," *Cell* 29:227-234, Cell Press (1982).
Brunelli, J. P. and Pall, M. L., "A Series of Yeast/*Escherichia coli* λ Expression Vectors Designed for Directional Cloning of cDNAs and *cre/lox*-Mediated Plasmid Excision," *Yeast* 9:1309-1318, John Wiley (1993).
Brunelli, J.P., and Pall, M.L., "Lambda/Plasmid Vector Construction by In Vivo *cre/lox*-Mediated Recombination," *BioTechniques* 16(6):1061-1064, Eaton Publishing Company (Jun. 1994).
Bubeck, P., et al., "Rapid cloning by homologous recombination in vivo," *Nucl. Acids Res.* 21:3601-3602, Oxford University Press (1993).
Buchholz, F., et al., "A simple assay to determine the functionality of Cre or FLP recombination targets in genomic manipulation constructs," *Nucl. Acids Res.* 24(15):3118-3119, Oxford University Press (Aug. 1996).
Buchholz, F., et al., "Different thermostabilities of FLP and Cre recombinases: implications for applied site-specific recombination," *Nucl. Acids Res.* 24(21):4256-4262, Oxford University Press (Nov. 1996).

Bushman, W., et al., "Control of Directionality in Lambda Site Specific Recombination," *Science* 230:906-911, Association for the Advancement of Science (1985).

Campbell, A. M., "Chromosomal Insertion Sites for Phages and Plasmids," *J. Bacteriol.* 174(23):7495-7499, American Society for Microbiology (1992).

Chapin, S.J., et al., "Differential expression of alternatively spliced forms of MAP4: a repertoire of structurally different microtubule-binding domains," *Biochem.* 34:2289-2301, American Chemical Society, Washington D.C. (Feb. 1995).

Chatterjee, P.K., and Coren, J.S., "Isolating large nested deletions in bacterial and P1 artificial chromosomes by in vivo P1 packaging of products o Cre-catalyzed recombination between the endogenous and a transposed *loxP* site," *Nucl. Acids Res.* 25:2205-2212, Oxford University Press (Jun. 1997).

Cox, M.M., "The FLP protein of the yeast 2-μm plasmid: Expression of a eukaryotic genetic recombination system in *Escherichia coli,"* *Proc. Natl. Acad. Sci. USA* 80:4223-4227, National Academy of Sciences of the USA (1983).

Craig, N.L. and Nash, H.A., "The Mechanism of Phage λ Site-Specific Recombination: Site-Specific Breakage of DNA by Int Topoisomerase," *Cell* 35:795-803, Cell Press, Cambridge, MA (1983).

Dale, E.C. and Ow, D.W., "Intra- and intermolecular site-specific recombination in plant cells mediated by bacteriophage P1 recombinase," *Gene* 91:79-85, Elsevier (1990).

Dale, E.C. and Ow, D.W., "Gene transfer with subsequent removal of the selection gene from the host genome," *Proc. Natl. Acad. Sci. USA* 88:10558-10562, National Academy of Sciences of the USA, Washington, D.C. (1991).

Dale, E.C., and Ow, D.W., "Mutations in the Cre/lox recombination site enhance the stability of recombination products: Applications for gene targeting in plants," *J. Cell. Biochem.* 16(Suppl. F):206, Abstract No. Y 108, Wiley-Liss, Inc. (1992).

Dang, D.T. and Perrimon, N., "Use of a Yeast Site-Specific Recombinase to Generate Embryonic Mosaics in Drosophila," *Develop. Genetics* 13:367-375, Wiley-Liss, Inc. (1992).

Davies, J., and Riechmann, L., "An antibody VH domain with a *lox*-Cre site integrated into its coding region: bacterial recombination within a single polypeptide chain," *FEBS Lett.* 377:92-96, Federation of European Biochemical Societies (Dec. 1995).

Degryse, E., "In vivo intermolecular recombination in *Escherichia coli*: application to plasmid constructions," *Gene* 170:45-50, Elsevier (Apr. 1996).

Devine, S. E., and Boeke, J.D., "Efficient integration of artificial transposons into plasmid targets in vitro: a useful tool for DNA mapping, sequencing and genetic analysis," *Nucl. Acids Res.* 22(18):3765-3772, Oxford University Press (Sep. 1994).

Diederich, L., et al., "New Cloning Vectors for Integration into the λ Attachment Site *attB* of the *Escherichia coli* Chromosome," *Plasmid* 28:14-24, Academic Press (1992).

Dymecki, S. M., "A modular set of *Flp, FRT* and *lacZ* fusion vectors for manipulating genes by site-specific recombination," *Gene* 171:197-201, Elsevier (Jun. 1996).

Elledge, S. J., et al., "λYES: A multifunctional cDNA expression vector for the isolation of genes by complementation of yeast and *Escherichia coli* mutations," *Proc. Natl. Acad. Sci. USA* 88:1731-1735, National Academy of Sciences of the USA (1991).

Feil, R., et al., "Regulation of Cre Recombinase Activity by Mutated Estrogen Receptor Ligand-Binding Domains," *Biochem. Biophys. Res. Comm.* 237:752-757, Academic Press, Inc. (Aug. 1977).

Ferguson, J., et al., "Construction and characterization of three yeast-*Escherichia coli* shuttle vectors designed for rapid subcloning of yeast genes on small DNA fragments," *Gene* 16:191-197, Elsevier (1981).

Fiering, S., et al., "An "in-out" strategy using gene targeting and FLP recombinase for the functional dissection of complex DNA regulatory elements: Analysis of the β-globin locus control region," *Proc. Natl. Acad. Sci. USA* 90:8469-8473, National Academy of Sciences of the USA (1993).

Filutowicz, M., et al., "Purification of the *Escherichia coli* integration host factor (IHF) in one chromatographic step," *Gene* 147:149-150, Elsevier (Sep. 1994).

Francia, M.V., and Lobo, J.M.G., "Gene Integration in the *Escherichia coli* Chromosome Mediated by Tn21 Integrase (Int21)," *J. Bacteriol.* 178:894-898, American Society for Microbiology (Feb. 1996).

Fukushige, S. and Sauer, B., "Genomic targeting with a positive-selection *lox* integration vector allows highly reproducible gene expression in mammalian cells," *Proc. Natl. Acad. Sci. USA* 89:7905-7909, National Academy of Sciences of the USA (1992).

Gage, P.J., et al., "A Cell-Free Recombination System for Site-Specific Integration of Multigenic Shuttle Plasmids into Herpes SImplex Type 1 Genome," *J. Virol.* 66:5509-5515, American Society for Microbiology (1992).

Geoffroy, F., et al., "A new phage display system to construct multicombinatorial libraries of very large antibody repertoires," *Gene* 151:109-113, Elsevier (Dec. 1994).

Glasgow, A.C., et al., "DNA-binding Properties of the Hin Recombinase," *J. Biol. Chem.* 264:10072-10082, American Society for Biochemistry and Molecular Biology, Inc. (1989).

Golic, K. G. and Lindquist, S., "The FLP Recombinase of Yeast Catalyzes Site-Specific Recombination in the Drosophila Genome," *Cell* 59:499-509, Cell Press (1989).

Götz, F., et al., "*Escherichia coli* 30S mutants lacking protein S20 are defective in translation initiation," *Biochim. Biophys. Acta* 1050:93-97, Elsevier Publishing Co. (1990).

Green, R. and Noller, H.F., "Ribosomes and Translation," *Ann. Rev. Biochem.* 66:679-716, Annual Reviews, Inc. (Jul. 1997).

Gu, H., et al., "Deletion of a DNA Polymerase β Gene Segment in T Cells Using Cell Type-Specific Gene Targeting," *Science* 265:103-106, Association for the Advancement of Science (Jul. 1994).

Guo, F., et al., "Asymmetric DNA bending in the Cre-*loxP* site-specific recombination synapse," *Proc. Natl. Acad. Sci. USA* 96:7143-7148, National Academy of Sciences of the USA (Jun. 1999).

Hall, R.M., and Collis, C.M., "Mobile gene cassettes and integrons: capture and spread of genes by site-specific recombination," *Mol. Microbiol.* 15:593-600, Blackwell Scientific Publications (Feb. 1995).

Hardy, S., et al., "Construction of Adenovirus Vectors through Cre-*lox* Recombination," *J. Virol.* 71(3):1842-1849, American Society for Microbiology (Mar. 1997).

Hasan, N., and Szybalski, W., "Control of cloned gene expression by promoter inversion in vivo: construction of improved vectors with a multiple cloning site and the $p_{tac}$ promoter," *Gene* 56:145-151, Elsevier (1987).

Hasan, N., et al., "*Escherichia coli* genome targeting, I. Cre-*lox*-mediated in vitro generation of *ori* plasmids and their in vivo chromosomal integration and retrieval," *Gene* 150:51-56, Elsevier (Dec. 1994).

Hashimoto-Gotoh, T., et al., "Improved vector, pHSG664, for direct streptomycin-resistance selection: cDNA cloning with G:C-tailing procedure and subcloning of double-digested DNA fragments," *Gene* 41:125-128, Elsevier (1986).

Hoekstra, M. F., et al., "Shuttle Mutagenesis: Bacterial Transposons for Genetic Manipulations in Yeast," *Meth. Enzymol.* 194:329-342, Academic Press Inc. (1991).

Hoess, R.H., et al., "P1 site-specific recombination: Nucleotide sequence of the recombining sites," *Proc. Natl. Acad. Sci. USA* 79:3398-3402, National Academy of Sciences of the USA (1982).

Hoess, R.H., et al., "Mechanism of Strand Cleavage and Exchange in the Cre-*lox* Site-specific Recombination System," *J. Mol. Biol.* 181:351-362, Academic Press, Inc. (1985).

Hoess, R., et al., "Formation of small circular DNA molecules via an in vitro site-specific recombination system," *Gene* 40:325-329, Elsevier (1985).

Hoess, R. H., et al., "The role of the *loxP* spacer region in P1 site-specific recombination," *Nucl. Acids Res.* 14(5):2287-2300, Oxford University Press (1986).

Hoess, R. H., and Abremski, K., "The Cre-*lox* Recombination System," *in: Nucleic Acids and Molecular Biology*, vol. 4, ed. by Eckstein, F. and D. M. J. Lilley, Springer-Verlag, Berlin, pp. 99-109 (1990).

Holt, C.L., and May, G.S., "A novel phage λ replacement Cre-*lox* vector that has automatic subcloning capabilities," *Gene 133*:95-97, Elsevier (1993).

Hoogenboom, H.R., et al., "Multi-subunit proteins on the surface of filamentous phage: methodologies for displaying antibody (Fab) heavy and light chains," *Nucl. Acids Res. 19*:4133-4137, Oxford University Press (1991).

Jaffé, A., et al., "Effects of the *ccd* Function of the F Plasmid on Bacterial Growth," *J. Bacteriol. 163*:841-849, American Society for Microbiology (1985).

Jayaram, M., "The *Int* family of site-specfic recombinases: Some thoughts on a general reaction mechanism," *J. Genet. 67*:29-36, Indian Academy of Sciences (1988).

Jeong, J.-H., et al., "Cloning and nucleotide sequencing of the genes, *rplU* and *rpmA*, for ribosomal proteins L21 and L27 of *Escherichia coli*," *J. DNA sequencing and Mapping 4*:59-67, Harwood Academic Publishers GmbH (1993).

Kanaar, R., et al., "Gin-Mediated Recombination of Catenated and Knotted DNA Substrates: Implications for the Mechanism of Interaction Between *Cis*-Acting Sites," *Cell 58*:147-159, Cell Press (1989).

Katz, L., et al., "Site-specific Recombination in *Escherichia coli* between the att sites of plasmid pSE211 from *Saccharopolyspora erythraea*," *Mol. Gen. Genet. 227*:155-159, Springer-Verlag (1991).

Kilby, N.J., et al., "Site-specific recombinases: tools for genome engineering," *Trends Genet. 9*:413-421, Elsevier Science Publishers Ltd. (1993).

Kim, S., et al., "Lambda Int Protein Bridges Between Higher Complexes at Two Distant Chromosomal Loci *att*L and *att*R," *Science 256*:198-203, Association for the Advancement of Science (1992).

Kitts, P.A. and Nash, H.A., "Bacteriophage Lambda Site-Specific Recombination Proceeds with a Defined Order of Strand Exchanges," *J. Mol. Biol. 204*:95-107, Academic Press, Inc. (1988).

Kozak, M., "An analysis of 5'-noncoding sequences from 699 vertebrate messenger RNAs," *Nucl. Acids res. 15*:8125-8132, Oxford University Press (1987).

Kozak, M., "Structural features in eukaryotic mRNAs that modulate the initiation of translation," *J. Biol. Chem 266*:19867-19870, American Society for Biochemistry and Molecular Biology, Inc. (1991).

Kraft, D.S., et al., "Stable Expression and Functional Characterization of a Human Cardiac Na$^+$ Channel Gene in Mammalian Cells," *J. Mol. Cell Cardiol. 27*:823-830, Academic Press Limited (Feb. 1995).

Kühn, R., et al., "Inducible Gene Targeting in Mice," *Science 269*:1427-1429, Association for the Advancement of Science (Sep. 1995).

Lafontaine, D., and Tollervey, D., "One-step PCR mediated strategy for the construction of conditionally expressed and epitope tagged yeast proteins," *Nucl. Acids Res. 24*:2469-2472, Oxford University Press (Sep. 1996).

Lake, J.A., "Evolving Ribosome Structure: Domains in Archaebacteria, Eubacteria, Eocytes and Eukaryotes," *Ann. Rev. Biochem. 54*:507-530, Annual Reviews, Inc. (1985).

Lakso, M., et al., "Targeted oncogene activation by site-specific recombination in transgenic mice," *Proc. Natl. Acad. Sci. USA 89*:6232-6236, National Academy of Sciences of the USA (1992).

Lander, E.S., "The New Genomics: Global Views of Biology," *Science 274*:536-539, Association for the Advancement of Science (Oct. 1996).

Landy, A., "Dynamic, Structural, and Regulatory Aspects of λ Site-Specific Recombination," *Annu. Rev. Biochem. 58*:913-949, Amercian Chemical Society (1989).

Landy, A., "Mechanistic and structural complexity in the site-specific recombination pathways on Int and FLP," *Curr. Op. Genet. Develop. 3*:699-707, Current Biology Ltd. (1993).

Lebreton, B., et al., "Mutations That Improve the Binding of Yeast FLP Recombinase to Its Substrate," *Genetics 118*:393-400, Genetics Society of America (1988).

Lee, E.C., et al., "Genetic Analysis of *Escherichia coli* Integration Host Factor Interactions with Its Bacteriophage λ H' Recognition Site," *J. Bacteriol. 173*:609-617, American Society for Microbiology (1991).

Lee, G., and Saito, I., "Role of nucleotide sequence of *lox*P spacer region in Cre-mediated recombination," *Gene 216*:55-65, Elsevier Science B.V. (Aug. 1998).

Leong, J.M., et al., "Generation of single base-pair deletions, insertions, and substitutions by a site-specific recombination system," *Proc. Natl. Acad. Sci. USA 82*:6990-6994, National Academy of Sciences of the USA (1985).

Liu, Q., et al., "The univector plasmid-fusion system, a method for rapid construction o recombinant DNA without restriction enzymes," *Curr. Biol. 8*:1300-1309, Current Biology Ltd. (Dec. 1998).

Lorbach, E. et al., "Site-specific Recombination in Human Cells Catalyzed by Phage λ Integrase Mutants," *J. Mol. Biol. 296*:1175-1181 Academic Press, Inc. (Mar. 2000).

Luckow, V. A., et al., "Efficient Generation of Infectious Recombinant Baculoviruses by Site-Specific Transposon-Mediated Insertion of Foreign Genes into a Baculovirus Genome Propagated in *Escherichia coli*," *J. Virol. 67*(8):4566-4579, American Society for Microbiology (1993).

Mackie, G.A., "Nucleotide Sequence of the Gene for Ribosomal Protein S20 and Its Flanking Regions," *J. Biol. Chem. 256*:8177-8182, American Society for Biochemistry and Molecular Biology, Inc. (1981).

Maeser, S., and Kahmann, R., "The Gin recombinase of phage Mu can catalyze site-specific recombination in plant protoplasts," *Mol. Gen. Genet. 230*:170-176, Springer-Verlag (1991).

Mahillon, J., et al., "IS231 and other *Bacillus thuringiensis* transposable elements: a review," *Genetica 93*:13-26, Dordrecht Kluwer Academic Publishers (Nov. 1994).

Matsuzaki, H., et al., "Chromosome Engineering in *Saccharomyces cerevisiae* by Using a Site-Specific Recombination System of a Yeast Plasmid," *J. Bacteriol. 172*:610-618, American Society for Microbiology (1990).

McCarthy, J.E. and Brimacombe, R., "Prokaryotic translation: the interactive pathway leading to initiation," *Trends Genet. 10*:402-407, Elsevier Science Publishers Ltd. (Nov. 1994).

Medberry, S.L., et al., "Intra-chromosomal rearrangements generated by Cre-*lox* site-specific recombination," *Nucl. Acids Res. 23*:485-490, Oxford University Press (Feb. 1995).

Miki, T. et al., "Control of Segregation of Chromosomal DNA by Sex Factor F in *Escherichia coli*. Mutants of DNA Gyrase Subunit A Suppress letD (*ccdB*) Product Growth Inhibition," *J. Mol. Biol. 225*:39-52, Academic Press, Inc. (1992).

Mizuuchi, K., and Mizuuchi, K., "Integrative Recombination of Bacteriophage λ: In Vitro Study of the Intermolecular Reaction," *Cold Spring Harb. Symp. Quant. Biol. 43*:1111-1114, Cold Spring Harbor Laboratory Press (1979).

Mizuuchi, M. and Mizuuchi, K., "The extent of DNA sequence required for a functional bacterial attachment site of phage lambda," *Nucl. Acids Res. 13*:1193-1208, Oxford University Press (1985).

Mozo, T. and Hooykaas, P. J. J., "Design of a novel system for the construction of vectors for Agrobacterium-mediated plant transformation," *Mol. Gen. Genet 236*:1-7, Springer-Verlag (1992).

Mullins, L.J., et al., "Efficient Cre-lox linearisation of BACs: applications to physical mapping and generation of transgenic animals," *Nucl. Acids Res. 25*(12):2539-2540, Oxford University Press (Jun. 1997).

Nagaraja, R. and Weisberg, R. A., "Specificity Determinants in the Attachment Sites of Bacteriophages HK022 and λ," *J. Bacteriol. 172*:6540-6550, American Society for Microbiology (1990).

Nash, H.A., "Integrative Recombination of Bacteriophage Lambda DNA In Vitro," *Proc. Natl. Acad. Sci. USA 72*:1072-1076, National Academy of Sciences of the USA (1975).

Nash, H.A., and Robertson, C.A., "Purification and properties of the *Escherichia coli* protein factor required for lambda integrative recombination," *J. Biol. Chem. 256*:9246-9253, American Society for Biochemistry and Molecular Biology Inc. (1981).

Nash, H. A., "Purification and Properties of the Bacteriophage Lambda Int Protein," *Meth. Enzymol. 100*:210-216, Academic Press Inc. (1983).

Nash, H. A., et al., "Role of homology in site-specific recombination of bacteriophage λ: Evidence against joining of cohesive ends," *Proc. Natl. Acad. Sci. USA 84*:4049-4053, National Academy of Sciences of the USA (1987).

Nash, H. and C.A. Robertson, "Heteroduplex substrates for bacteriophage lambda site-specific recombination: cleavage and strand transfer products," *EMBO J. 8*:3523-3533, IRL Press Limited (1989).

Nash, H.A., "Bending and supercoiling of DNA at the attachment site of bacteriophage λ," *Trends Biochem. Sci 15*:222-227, International Union of Biochemistry and Elsevier Trends Journal, Cambridge, England (1990).

Nomura, M., et al., "Regulation of the Synthesis of Ribosomes and Ribosomal Components," *Ann. Rev. Biochem. 53*:75-117, Annual Reviews, Inc., Palo Alto, CA (1984).

Numrych, T. E., et al., "A comparison of the effects of single-base and triple-base changes in the integrase arm-type binding sites on the site-specific recombination of bacteriophage lambda," *Nucl. Acids Res. 18*:3953-3959, Oxford University Press, Oxford, England (1990).

Numrych, T.E., et al., "Characterization of the bacteriophage lambda excisionase (Xis) protein: the C-terminus is required for Xis-integrase cooperativity but not for DNA binding," *EMBO J. 11*(10):3797-3806, IRL Press Limited, Oxford, England (1992).

Nunes-Düby, S.E., et al., "Half-*att* Site Substrates Reveal the Homology Independence and Minimal Protein Requirements for Productive Synapsis in λ Excisive Recombination," *Cell 59*:197-206, Cell Press (1989).

Nunes-Düby, et al., "Similarities and differences among 105 members of the Int family of site-specific recombinases," *Nucl. Acids Res. 26*:391-406, Oxford University Press (Jan. 1998).

Oberto, J., et al., "A segment of the phage HK022 chromosomes is a mosaic of other lambdoid chromosomes," *Nucl. Acids Res. 22*(3):354-356, Oxford University Press (Feb. 1994).

Oliner, J.D., et al., "In vivo cloning of PCR products in *E. coli*," *Nucl. Acids Res. 21*:5192-5197, Oxford University Press (1993).

Orban, P. C., et al., "Tissue- and site-specific DNA recombination in transgenic mice," *Proc. Natl. Acad. Sci. USA 89*:6861-6865, National Academy of Sciences of the USA (1992).

Osborne, B.I., et al., "A system for insertional mutagenesis and chromosomal rearrangement using the Ds transposon and Cre-*lox*,"*Plant J. 7*:687-701, Oxford Bios Scientific Publishers And Blackwell Scientific Publications In Association With The Society For Experimental Biology (Apr. 1995).

Padget, K. A. and Sorge, J. A., "Creating seamless junctions independent of restriction sites in PCR cloning," *Gene 168*:31-35, Elsevier (Feb. 1996).

Palazzolo, M. J., et al., "Phage lambda cDNA cloning vectors for subtractive hybridization, fusion-protein synthesis and Cre-*loxP* automatic plasmid subcloning," *Gene 88*:25-36, Elsevier (1990).

Pan, G., et al., "Ligation of Synthetic Activated DNA Substrates by Site-specific Recombinases and Topoisomerase I," *J. Biol. Chem. 268*(5):3683-3689, American Society for Biochemistry and Molecular Biology, Inc., Baltimore, MD (1993).

Parks, R.J., and Graham, F.L., "A Helper-Dependent System for Adenovirus Vector Production Helps Define a Lower Limit for Efficient DNA Packaging," *J. Virol. 71*(4):3293-3298, American Society for Microbiology (Apr. 1997).

Peakman, T. C., et al., "Highly efficient generation of recombinant baculoviruses by enzymatically mediated site-specific in vitro recombination," *Nucl. Acids Res. 20*:495-500, Oxford University Press (1992).

Peredelchuk, M.Y., and Bennett, G.N., "A method for construction of *E. coli* strains with multiple DNA insertions in the chromosome," *Gene 187*:231-238 Elsevier (Mar. 1997).

Pichel, J. G., et al., "Timing of SV40 oncogene activation by site-specific reombination determines subsequent tumor progression during murine lens development," *Gene 8*:3333-3342, Elsevier (1993).

Pierce, J. C., et al., "A positive selection vector for cloning high molecular weight DNA by the bacteriophage P1 system: Improved cloning efficacy," *Proc. Natl. Acad. Sci. USA 89*:2056-2060, National Academy of Science of the USA (1992).

Podhajska, A. J., et al., "Control of cloned gene expression by promoter inversion in vivo: construction of the heat-pulse-activated *att-nutL-p-att-N* module," *Gene 40*:163-168, Elsevier (1985).

Pósfai, G., et al., "In vivo excision and amplification of large segments of the *Escherichia coli* genome," *Nucl. Acids Res. 22*(12):2392-2398, Oxford University Press (Jun. 1994).

Prasad, P. V., et al., "Substrate Recognition by the 2μm Circle Site-Specific Recombinase: Effect of Mutations within the Symmetry Elements of the Minimal Substrate," *Mol. Cell. Biol. 6*:4329-4334, American Society for Microbiology (1986).

Qian, X., et al., "Reactions between Half- and Full-FLP Recombination Target Sites: A Model System for Analyzing Early Steps in FLP Protein-Mediated Site-Specific Recombination," *J. Biol. Chem 267*(11):7794-7805, American Society for Biochemistry and Molecular Biology, Inc. (1992).

Reed, R.R., "Transposon-Mediated Site-Specific Recombination: A Defined in Vitro System," *Cell 25*:713-719, Cell Press (1981).

Reed, R.R. and N.D. Grindley, "Transposon-Mediated Site-Specific Recombination in Vitro: DNA Cleavage and Protein-DNA Linkage at the Recombination Site," *Cell. 25*:721-728, Cell Press (1981).

Richet, E., et al., "The Interaction of Recombination Proteins with Supercoiled DNA: Defining the Role of Supercoiling in Lambda Integrative Recombination," *Cell 46*:1011-1021, Cell Press (1986).

Richet, E., et al., "Synapsis of Attachment Sites during Lambda Integrative Recombination Involves Capture of a Naked DNA by a Protein-DNA Complex," *Cell 52*:9-17, Cell Press (1988).

Sadowski, P., "Site-Specific Recombinases: Changing Partners and Doing the Twist," *J. Bacteriol. 165*(2):341-347, American Society for Microbiology (1986).

Sadowski, P.D., "The FLP recombinase of the 2-microns plasmid of *Saccharomyces cerevisiae,"Prog. Nucl. Acid Res. Mol. Biol. 51*:53-91, Academic Press (Jul. 1995).

Sauer, B., et al., "Site-specific insertion of DNA into a pseudorabies virus vector," *Proc. Natl. Acad. Sci. USA 84*:9108-9112, National Academy of Sciences of the USA (1987).

Sauer, B., "Functional Expression of the *cre-lox* Site-Specific Recombination System in the Yeast *Saccharomyces cervisiae*," *Mol. Cell. Biol. 7*:2087-2096, American Society for Microbiology (1987).

Sauer, B. and Henderson, N., "The cyclization of linear DNA in *Escherichia coli* by site-specific recombination," *Gene 70*:331-341, Elsevier (1988).

Sauer, B. and Henderson, N., "Cre-stimulated recombination at *loxP*-containing DNA sequences placed into the mammalian genome," *Nucl. Acids. Res. 17*:147-161, Oxford University Press (1989).

Sauer, B., "Manipulation of Transgenes by Site-Specific Recombination: Use of Cre Recombinase," *Meth. Enzymol.* 225:890-900, Academic Press Inc. (1993).

Sauer, B., "Site-specific recombination: developments and applications," *Curr. Op. Biotechnol.* 5:521-527, Current Biology, Ltd. (Oct. 1994).

Sauer, B., "Multiplex Cre/*lox* recombination permits selective site-specific DNA targeting to both a natural and an engineered site in the yeast genome," *Nucl. Acids Res.* 24(23):4608-4613, Oxford University Press (Dec. 1996).

Sauer, B., "Inducible Gene Targeting in Mice Using the Cre/*lox*system," *Methods 14*:381-392, Academic Press, Inc. (Apr. 1998).

Schindelhauer, D., and Cooke, H.J., "Efficient combinations of large DNA in vitro: in gel site specific recombination (IGSSR) of PAC fragments containing α satellite DNA and the human HPRT gene locus," *Nucl. Acids Res. 25*(11):2241-2243, Oxford University Press (Jun. 1997).

Schlake, T., and Bode, J., "Use of Mutated FLP Recognition Target (FRT) Sites for the Exchange of Expression Cassettes at Defined Chromosomal Loci," *Biochem. 33*:12746-12751, American Chemical Society (Nov. 1994).

Segall, A. M. and Nash, H. A., "Synaptic intermediates in bacteriophage lambda site-specific recombination: intergrase can align pairs of attachment sites," *EMBO J.* 12:4567-4576, IRL Press Limited (1993).

Segall, A.M., and Nash, H.A., "Architectural flexibility in lambda site-specific recombination: three alternate conformations channel the *attL* site into three distinct pathways," *Genes to Cells 1*: 453-463, Blackwell Science Ltd. (May 1996).

Senecoff, J.F., et al., "DNA Recognition by the FLP Recombinase of the Yeast 2 μ Plasmid—A Mutational Analysis of the FLP Binding Site," *J. Mol. Biol.* 201:405-421, Academic Press, Inc., New York, NY (1988).

Sheffield, P. et al., "Overcoming Expression and Purification Problems of RhoGDI Using a Family of "Parallel" Expression Vectors," *Protein Expr. Purific.* 15:34-39, Academic Press, New York, NY (Feb. 1999).

Shuman, S., "Recombination mediated by vaccinia virus DNA topoisomerase I in *Escherichia coli* is sequence specific," *Proc. Natl. Acad. Sci. USA* 88:10104-10108, National Academy of Sciences of the USA, Washington, D.C. (1991).

Simpson, J.C., et al., "Systematic subcellular localization of novel proteins identified by large-scale cDNA sequencing," *EMBO Reports* 1:287-292, IRL Press Limited (Sep. 2000).

Sizemore, C., et al., "Quantitative analysis of Tn10 Tet repressor binding to a complete set of *tet* operator mutants," *Nucl. Acids Res.* 18(10):2875-2880, Oxford University Press (1990).

Smith, A. J. H., et al., "A site-directed chromosomal translocation induced in embryonic stem cells by Cre-*loxP* recombination," *Nat. Gen.* 9:376-385, Nature Publishing Co. (Apr. 1995).

Snaith, M.R., et al., "Multiple cloning sites carrying *loxP* and *FRT* recognition sites for the Cre and Flp site-specific recombinases," *Gene* 166:173-174, Elsevier (Dec. 1995).

Spengler, S.J., et al., "The Stereostructure of Knots and Catenanes Produced by Phage λ Integrative Recombination: Implications for Mechanism and DNA Structure," *Cell* 42:325-334, Cell Press (1985).

Sternberg, N., et al., "Site-specific Recombination and Its Role in the Life Cycle of Bacteriophage P1," *Cold Spring Harbor Symp. Quant. Biol.* 45:297-309, Cold Spring Harbor Laboratory Press (1981).

Sternberg, N., et al., "Bacteriophage P1 *cre* Gene and its Regulatory Region," *J. Mol. Biol.* 187:197-212, Academic Press, Inc. (1986).

Sternberg, N., "Bacteriophage P1 cloning system for the isolation, amplification, and recovery of DNA fragments as large as 100 kilobase pairs," *Proc. Natl. Acad. Sci. USA* 87:103-107, National Academy of Sciences of the USA (1990).

Storck, T., et al., "Rapid construction in yeast of complex targeting vectors for gene manipulation in the mouse," *Nucl. Acids Res.* 24:4594-4596, Oxford University Press (Nov. 1996).

Stratagene catalog, "Gene Characterization Kits," pp. 39, Stratagene (1988).

Strathmann, M., et al., "Transposon-facilitated DNA sequencing," *Proc. Natl. Acad. Sci. USA* 88:1247-1250, National Academy of Sciences of the USA (1991).

Thompson, J. F., et al., "Mutations in an Integration Host Factor-Binding Site: Effect on Lambda Site-Specific Recombination and Regulatory Implications," *J. Bacteriol.* 168:1343-1351, American Society for Microbiology (1986).

Thompson, J.F., et al., "Helical-repeat dependence of integrative recombination of bacteriophage λ: Role of the *P1* and *H1* protein binding sites," *Proc. Natl. Acad. Sci. USA* 85:6323-6327, National Academy of Sciences of the USA (1988).

Thorpe, H.M., and Smith, M.C.M., "In vitro site-specific integration of bacteriophage DNA catalyzed by a recombinase of the resolvase/invertase family," *Proc. Natl. Acad. Sci. USA* 95:5505-5510, National Academy of Sciences of the USA (May 1998).

Tsurushita, N., et al., "Phage display vectors for in vivo recombination of immunoglobulin heavy and light chain genes to make large combinatorial libraries," *Gene* 172:59-63, Elsevier (Jun. 1996).

Vanin, E.F., et al., "Development of High-Titer Retroviral Producer Cell Lines by Using Cre-Mediated Recombination," *J. Virol.* 71:7820-7826, American Society for Microbiology (Oct. 1997).

Venkatesh, T.V., and Redding, C.M., "Ribosomal Protein S1 and NusA Protein Complexed to Recombination Protein β of Phage λ," *J. Bacteriol.* 175:1844-1846, American Society for Microbiology (1993).

Wang, G., et al., "pDUAL: A transposon-based cosmid cloning vector for generating nested deletions and DNA sequencing templates in vivo," *Proc. Natl. Acad. Sci. USA* 90:7874-7878, National Academy of Sciences of the USA (1993).

Wasserman, S.A., et al., "The helical repeat of double-stranded DNA varies as a function of catenation and supercoiling," *Nature* 334:448-450, Macmillan Publishers Ltd. (1988).

Waterhouse, P., et al., "Combinatorial infection and in vivo recombination: a stategy for making large phage antibody repertoires," *Nucl. Acids Res.* 21(9):2265-2266, Oxford University Press (1993).

Wierzbicki, A., et al., "A Mutational Analysis of the Bacteriophage P1 Recombinase Cre," *J. Mol. Biol.* 195:785-794, Academic Press, Inc. (1987).

Weisberg, R. A., and Landy, A., "Site-specific Recombination in Phage Lambda," in: "Lambda II," Hendrix, R. W. et al., eds., Cold Spring Harbor Laboratory Press, Cold Spring Harbor, N. Y., pp. 211-250 (1983).

Wild, J., et al., "A broad-host-range in vivo pop-out and amplification system for generating large quantities of 50- to 100-kb genomic fragments for direct DNA sequencing," *Gene* 179:181-188, Elsevier (Nov. 1996).

Wild, J., et al., "Targeting and retrofitting pre-existing libraries of transposon insertions with *FRT* and *oriV* elements for in-vivo generation of large quantities of any genomic fragment," *Gene* 223:55-66, Elsevier (Nov. 1998).

Winoto, A.,et al., "Directional Control of Site-specificed Recombination by Bacteriophage λ," *J. Mol. Biol.* 192:677-680, Academic Press, Inc. (1986).

Wittman, H.G., "Components of Bacterial Ribosomes," *Ann. Rev. Biochem.* 51:155-183, Annual Reviews, Inc. (1982).

Wittman, H.G., "Architecture of Prokaryotic Ribosomes," *Ann. Rev. Biochem.* 52:35-65, Annual Reeviews, Inc. (1983).

Yang, W., and Mizuuchi, K., "Site-specific recombination in plane view," *Structure* 5:1401-1406, Current Biology (Nov. 1997).

Yanisch-Perron, C., et al., "Improved M13 phage cloning vectors and host strains: nucleotide sequences of the M13mp18 and pUC19 vectors," *Gene* 33:103-119, Elsevier (1985).

Yoon, Y.G., et al., "Cre/*loxP*-mediated in vivo excision of large segments from yeast genome and their amplification based on the 2 μm plasmid-derived system," *Gene* 223:67-76, Elsevier (Nov. 1998).

York, D., et al., "Simple and efficient generation in vitro of nested deletions and inversions: Tn5 intramolecular transposition," *Nucl. Acids Res.* 26:1927-1933, Oxford University Press (Apr. 1998).

Zahra, D.G., et al., "Selective in-vivo recombination to increase antibody library size—an improved phage display vector system," *Gene* 227:49-54, Elsevier Science Publishers B.V. (Feb. 1999).

Zhang, Y. et al., "A new logic for DNA engineering using recombination in *Escherichia coli*," *Nat. Genet.* 20:123-128, Nature Publishing Co. (Oct. 1998).

Zhu, et al., "Homology requirements for ligation and strand exchange by the FLP recombinase," *J. Biol. Chem.* 270:11646-11653, American Society for Biochemistry and Molecular Biology, Inc. (May 1995).

Dialog File 351 (Derwent World Patents Index), unverified English language abstract for WIPO/PCT Publication No. WO 98/53056 (Document No. AM4) ; WPI Accession No. 1999-000502/199901.

Dialog File 351 (Derwent World Patents Index), unverified English language abstract for WIPO/PCT Publication No. WO 99/25851 (Document No. AP4) WPI Accession No. 1999-347485/199929.

Internatioanl Search Report for International Application No. PCT/US98/22589, mailed Oct. 26, 1998.

Pending U.S. Appl. No. 09/177,387, filed Oct. 23, 1998.
Pending U.S. Appl. No. 09/432,085, filed Nov. 2, 1999.
Pending U.S. Appl. No. 09/438,358, filed Nov. 12, 1999.
Pending U.S. Appl. No. 09/498,074, filed Feb. 4, 2000.
Pending U.S. Appl. No. 09/517,466, filed Mar. 2, 2000.
Pending U.S. Appl. No. 09/518,188, filed Mar. 2, 2000.
Pending U.S. Appl. No. 09/695,065, filed Oct. 25, 2000.

Pending U.S. Appl. No. 09/732,914, filed Dec. 11, 2000.
CLONTECH, "Creator™ Gene Cloning & Expression System," *CLONTECHniques* 15:7-11, CLONTECH, (Apr. 2000).
CLONTECH, "New Creator™ -Compatible Expression Systems," *CLONTECHniques* 15:2 pages, CLONTECH, (Oct. 2000).
CLONTECH, "Creator™ Acceptor Vector Construction Kit," *CLONTECHniques* 16:2 pages, CLONTECH, (Oct. 2001).
CLONTECH, "Creator™ pDNR-Dual Cloning Kit," *CLONTECHniques* 16:3 pages, CLONTECH, (Oct. 2001).
CLONTECH, "Creator™ SMART™ Library Construction Kit," *CLONTECHniques* 16:2 pages, CLONTECH, (Oct. 2001).
CLONTECH, "Creator™: The Universal Platform for Analysis of Gene Function," *Powerpoint Presentation*, pp. 1-9, CLONTECH, (Jul. 24, 2001), *available at* http://www.clontech.com/products/families/creator/popups/s1page1.shtml.
CLONTECH, "New Additions to the Creator™ Platform," *CLONTECHniques* 16:1-4, CLONTECH, (Jan. 2001).
Murayama, N., et al., "Evidence for Involvement of *Escherchia coli* Genes pmbA; csrA and a Previously Unrecognized Gene tldD, in the Control of DNA Gyrase by letD (ccdB) of Sex Factor F," *J. Mol. Biol.* 256:483-502, Academic Press Limited (1996).
Bauer, C.E., et al., "Extent of Sequence Homology Required for Bacteriophage Lambda Site-specific Recombination," *J. Mol. Biol.* 181:187-197 (1985).
Cherepanov, P.P., and Wackernagel, W., "Gene disruption in *Escherichia coli*: Tc$^R$ and Km$^R$ cassettes with the option of Flp-catalyzed excison of the antibiotic-resistance determinant," *Gene* 158:9-14 (received by library in Jun. 1995).
Collis, C.M., and Hall, R.M., "Expression of Antibiotic Resistance Genes in the Integrated Cassettes of Integrons," *Antimicrob. Agents Chemother.* 39:155-162 (Jan. 1995).
Qin, M., et al., "Cre recombinase-mediated site-specific recombination between plant chromosomes," *Proc. Natl. Acad. Sci. USA* 91:1706-1710 (Mar. 1994).
Akagi, K., et al., "Cre-mediated somatic site-specific recombination in mice," *Nucl. Acids Res.* 25:1781-1788, Oxford University Press (1997).
Aladjem, M.I., et al., "Positive Selection of FLP-Mediated Unequal Sister Chromatid Exchange Products in Mammalian Cells," *Mol. Cell. Biol.* 17:857-861, American Society for Microbiology (1997).
Angelastro, J.M., et al., "Identification of diverse nerve growth factor- regulated genes by serial analysis of gene expression (SAGE) profiling," *Proc. Natl. Acad. Sci. USA* 97:10424-10429, National Academy of Sciences (2000).
Angrand, P.-O., et al., "Inducible expression based on regulated recombination: a single vector strategy for stable expression in cultured cells," *Nucl. Acids Res.* 26:3263-3269, Oxford University Press (1998).
Ayres, E.K., et al., "Precise Deletions in Large Bacterial Genomes by Vector-mediated Excision (VEX). The *trfA* Gene of Promiscuous Plasmid RK2 is Essential for Replication in Several Gram-negative Hosts," *J. Mol. Biol.* 230:174-185, Academic Press (1993).
Backman, K., et al., "Use of Synchronous Site-Specific Recombination In Vivo to Regulate Gene Expression," *Bio/Technology* 2:1045-1049, Nature Publishing Company (1984).
Bai, C., et al., "SKP1 Connects Cell Cycle Regulators to the Ubiquitin Protoeolysis Machinery through a Novel Motif, the F-Box," *Cell* 86:263-274, Cell Press (1996).
Barnes, G., and Rine, J., "Regulated expression of endonuclease EcoRI in *Saccharomyces cerevisiae*: Nuclear entry and biological consequence," *Proc. Natl. Acad. Sci. USA* 82:1354-1358, National Academy of Sciences (1985).
Bernard, P., "Positive Selection of Recombinant DNA by CcdB," *Biotechniques* 21:320-323, Eaton Publishing Company (1996).
Bernard, P., et al., "The F Plasmid CcdB Protein Induces Efficient ATP-dependent DNA Cleavage by Gyrase," *J. Mol. Biol.* 234:534-541, Academic Press (1993).
Brent, R., and Ptashne, M., "A bacterial repressor protein or a yeast transcriptional terminator can block upstream activation of a yeast gene," *Nature* 312:612-615, Macmillan Journals Ltd. (1984).
Boshart, M.., et al., "A Very Strong Enhancer is Located Upstream of an Immediate Early Gene of Human Cytomegalovirus," *Cell* 41:521-530, The MIT Press (1985).

Bouhassira, E.E., et al., "Transcriptional Behavior of LCR Enhancer Elements Integrated at the Same Chromosomal Locus by Recombinase-Mediated Cassette Exchange," *Blood* 90:3332-3344, The American Society of Hematology (1997).
Burioni, R., et al., "An improved phage display vector for antibody repertoire cloning by construction of combinatorial libraries," *Res. Virol.* 148:161-164, Elsevier (1997).
Capone, J. P., et al., "Introduction of UAG, UAA, and UGA Nonsense Mutations at a Specific Site in the *Escherichia coli* Chloramphnicol Acetyltransferase Gene: Use in Measurement of Amber, Ochre, and Opal Suppression in Mammalian Cells," *Mol. Cell. Biol.* 6:3059-3067, American Society for Microbiology (1986).
Chanock, R.M., et al., "Human Monoclonal Antibody Fab Fragments Cloned from Combinatorial Libraries: Potential Usefulness in Prevention and/or Treatment of Major Human Viral Diseases," *Infect. Agents Dis.* 2:118-131, Raven Press (1993).
Chong, S., et al., "Single-column purification of free recombinant proteins using a self-cleavable affinity tag derived from a protein splicing element," *Gene* 192:271-281, Elsevier Science B.V. (1997).
Choulika, A., et al. "Transfer of Single Gene-Containing Long Terminal Repeats into the Genome of Mammalian Cells by a Retroviral Vector Carrying the *cre* Gene and the *loxP* Site." *J. Virol.* 70:1792-1798, American Society for Microbiology (1996).
Chuang, C.-F., and Meyerowitz, E.M., "Specific and heritable genetic interference by double-stranded RNA in *Arabidopsis thaliana,*" *Proc. Natl. Acad. Sci. USA* 97:4985-4990, National Academy of Sciences (2000).
Cormack, B., "Directed Mutagenesis Using the Polymerase Chain Reaction," in *Current Protocols in Molecular Biology*, Ausubel, F.M., et al., eds., John Wiley & Sons, Inc., New York, NY, pp. 8.5.1-8.5.10 (1997).
Cigan, A.M., et al., "Mutational Analysis of the *HIS4* Translational Initiator Region in *Saccharomyces cerevisiae,*" *Mol. Cell. Biol.* 8:2964-2975, American Society for Microbiology (1998).
Curcio, M.J., and Garfinkel, D.J., "Single-step selection for Ty1 element retrotransposition," *Proc. Natl. Acad. Sci. USA* 88:936-940, National Academy of Sciences (1991).
Datson, N.A., et al., "MicroSAGE: a modified procedure for serial analysis of gene expression in limited amounts of tissue," *Nucl. Acids Res.* 27:1300-1307, Oxford University Press (1999).
Davis, C.R., et al., "Analysis of the Mechanism of Action of the *Saccharomyces cerevisiae* Dominant Lethal cdc42$^{G12V}$ and Dominant Negative cdc42$^{D118A}$ Mutations," *J. Biol. Chem.* 273:849-858, The American Society for Biochemistry and Molecular Biology (1998).
Deng, M.-D., and Coleman, J.R., "Ethanol Synthesis by Genetic Engineering in Cyanobacteria," *Appl. Environ. Microbiol.* 65:523-528, American Society for Microbiology (1999).
Derbyshire, V., and Belfort, M., "Lightning strikes twice: Intron-intein coincidence," *Proc. Natl. Acad. Sci. USA* 95:1356-1357, National Academy of Sciences (1998).
Dijkema, R., et al., "Cloning and expression of the chromosomal immune interferon gene of the rat." *EMBO J.* 4:761-767, IRL Press Limited (1985).
Enquist, L.W., and Weisberg, R.A., "The Red Plaque Test: A Rapid Method for Identification of Excision Defective Variants of Bacteriophage Lambda," *Virology* 72: 147-153, Academic Press (1976).
Esposito, D., and Scocca, J.J., "The integrase family of tyrosine recombinases: evolution of a conserved active site domain," *Nucl. Acids Res.* 25:3605-3614, Oxford University Press (1997).
Feinbaum, F., "Vectors Derived from Plasmids," in *Current Protocols in Molecular Biology* , Ausubel, F. M., et al., eds., John Wiley & Sons, Inc., New York, NY, pp. 1.5.1-1.5.17 (1998).
Flanagan, P.M., and Fennewald, M.A., "Analysis of Inhibitors of the Site-specific Recombination Reaction Mediated by TN3 Resolvase," *J. Mol. Biol.* 206:295-304, Academic Press (1989).
Flores, A., et al., "A protein-protein interaction map of yeast RNA polymerase III," *Proc. Natl. Acad. Sci. USA* 96:7815-7820, National Academy of Science (1999).

Francia, M.V., et al., "The IntI1 Integron Preferentially Binds Single-Stranded DNA of the *attC* Site," *J. Bacteriol. 181*:6844-6849, American Society for Microbiology (1999).

Gateway™ Cloning Technology, Version 1, GIBCO BRL, Life Technologies Instruction Manual, [retrieved from <http://www.lifetech.com/gateway>], pp. 1-60 (1999).

Gay, P., et al., "Positive Selection Procedure for Entrapment of Insertion Sequence Elements in Gram-Negative Bacteria," *J. Bacteriol. 164*:918-921, American Society for Microbiology (1985).

Gay, P., et al., "Cloning Structural Gene *sacB*, Which Codes for Exoenzyme Levansucrase of *Bacillus subtilis*: Expression of the Gene in *Escherichia coli*," *J. Bacteriol. 153*:1424-1433, American Society for Microbiology (1983).

Gorman, C. M., et al. "The Rous sarcoma virus long terminal repeat is a strong promoter when introduced into a variety of eukaryotic cells by DNA-mediated transfection," *Proc. Natl. Acad. Sci. USA 79*:6777-6781, National Academy of Sciences (1982).

Grindley, N.D.F., and Kelley, W.S., "Effects of Different Alleles of the *E. coli* K12 *polA* Gene on the Republication of Non-transferring Plasmids," *Molec. Gen. Genet. 143*:311-318, Springer Verlag (1976).

Gronostajski, R.M., and Sadowski, P.D., "The FLP Protein of the 2-micron Plasmid of Yeast. Inter- and Intramolecular Reactions," *J. Biol. Chem. 260*:12328-12335, The American Society of Biological Chemists (1985).

Haffter, P., and Bickle, T.A., "Enhancer-indepedent mutants of the Cin Recombinase have a relaxed topological specificty," *EMBO J. 7*:3991-3996, IRL Press Limited (1988).

Hancock, R.E.W., and Scott, M.G., "The role of antimicrobial peptides in animal defenses," *Proc. Acad. Sci. USA 97*:8856-8861, National Academy of Sciences (2000).

Hehl, R., et al., "Structural analysis of Tam3, a transposable element from *Antirrhinum majus*, reveals homologies to the Ac element from maize," *Plant Molec. Biol. 16*:369-371, Kluwer Academic Publishers (1991).

Henikoff, S., "Unidirectional digestion with exonuclease III creates targeted breakpoints for DNA sequencing," *Gene 28*:351-359, Elsevier Science Publishers (1984).

Hochuli, E., et al., "Genetic Approach to Facilitate Purification of Recombinant Proteins with a Novel Metal Chelate Adsorbent." *Bio/Technology 6*: 1321-1325, Nature Publishing Company (1988).

Hoess, R.H., and Abremski, K., "Interaction of the bacteriophage P1 recombinase Cre with the recombing site *loxP*," *Proc. Natl. Acad. Sci. USA 81*:1026-1029, National Academy of Sciences (1984).

Iida, S., et al., "A site-specific, conservative recombination system carried by bacteriophage P1. Mapping of the recombinase gene *cin* and the crossover sites *cix* for the inversion of the C segment." *EMBO J. 1*:1445-1453, IRL Press Limited (1982).

Iino, T., and Kutsukake, K., "*Trans*-acting Genes of Bacteriophages P1 and Mu Mediate Inversion of a Specific DNA Segment Involved in Flagellar Phase Variation of *Salmonella*," *Cold Spring Harbor Symp. Quant. Biol. 45*:11-16, Cold Spring Harbor Laboratory (1981).

Johnson, R.C., et al., "Isolation of the gene encoding the Hin recombinational enhancer binding protein," *Proc. Natl. Acad. Sci. USA 85*:3484-3488, National Academy of Sciences (1998).

Kaniga, K., et al., "A wide-host-range suicide vector for improving reverse genetics in Gram-negative bacteria: inactivation of the *blaA* gene of *Yersinia enterocolitica*," *Gene 109*:137-141, Elsevier Science B.V. (1991).

Kealey, J.T., et al., "Production of polyketide natural product in nonpolyketide-producing prokaryotic and eukaryotic hosts," *Proc. Natl. Acad. Sci. USA 95*:505-509, National Academy of Sciences (1998).

Kholodenko, B.N., et al., "Metabolic Design: How to Engineer a Living Cell to Desired Metabolite Concentrations and Fluxes," *Biotechnol. Bioengineer. 59*:239-247, John Wiley & Son (1998).

Kim, D.W., "Use of the human elongation factor 1a promoter as a versatile and efficient expression systems," *Gene 91*:217-223, Elsevier Sciences B.V. (1990).

Klippel, A., et al., "Isolation and characterization of unusual *gin* mutants," *EMBO J. 7*:3983-3989, IRL Press Limited (1988).

Koch, C., et al., "*Escherichia coli* host factor for site-specific DNA inversion: Cloning and characterization of the *fis* gene," *Proc. Natl. Acad. Sci. USA 85*:4237-4241, National Academy of Sciences (1988).

Kolb, A.F., and Siddell, S.G., "Genomic targeting with an MBP-Cre fusion protein," *Gene 183*:53-60, Elsevier Science B.V. (1996).

Kouprina, N., et al., "Rescue of Targeted Regions of Mammalian Chromosomes by in Vivo Recombination in Yeast," *Genome Res. 8*:666-672, Cold Spring Harbor Laboratory Press (1998).

Kozak, M., "Comparison of Initiation of Protein Synthesis in Procaryotes, Eucaryotes, and Organelles," *Microbiol. Rev. 47*:1-45, American Society for Microbiology (1983).

Krautwald, S. and Baccarini, M. "Bacterially Expressed Murine CSF-1 Possesses Agonistic Activity in its Monomeric Form." *Biochem. Biophys. Res. Commun. 192*: 720-727, Academic Press (1993).

Langeveld, S.A. et al., "Expression of an *Escherichia coli phr* gene in the yeast *Saccharomyces cerevisiae*," *Mol. Gen. Genet. 199*: 396-400, Springer-Verlag (1985).

Leslie, N.R., and Sherratt, D.H., "Site-specific recombination in the replication termius region of *Escherichia coli*: functional replacement of dif," *EMBO J. 14*:1561-1570, Oxford University Press (Apr. 1995).

Leung, L.L.K., "Application of Combinatorial Libraries and Protein Engineering to the Discovery of Novel Anti-Thrombotic Drugs," *Thromb. Haemost. 74*:373-376, F.K. Schattauer Verlagsgesellschaft mbH (Jul. 1995).

Li, Z.-W., et al. Generation of mice with a 200-kb amyloid precursor protein gene deletion by Cre recombinase-medicated site-specific recombination in embryonic stem cells. *Proc. Natl. Acad. Sci. USA 93*:6158-6162, National Academy of Sciences (1996).

Lu, F., and Churchward, G., "Conjugative Transposition" Tn*916* integrase contains two independent DNA binding domains that recognize differnt DNA sequences, *EMBO J. 13*:1541-1548, Oxford University Press (Apr. 1994).

Madison, L.L., and Huisman, G.W., "Metabolic Engineering of Poly(3-Hydroxyalkanoates): From DNA to Plastic," *Microbiol. Mol. Biol. Reviews 63*:21-53, American Society for Microbiology (1999).

Maemura, K., et al., "Generation of a Dominant-negative Mutant of Endothelial PAS Domain Protein 1 by Deletion of a Potent C-terminal Transactivation Domain," *J. Biol. Chem. 274*:31565-31570, The American Society for Biochemistry and Molecular Biology (1999).

Mahillon, J., et al., "Subdivision of the *Escherichia coli* K-12 genome for sequencing: manipulation and DNA sequence of transposable elements introducing unique restriction sites," *Gene 223*:47-54, Elsevier Science B.V. (1998).

Malynn, B.A., et al., "The *scid* Defect Affects the Final Step of the Immunoglobulin VDJ Recombinase Mechanism," *Cell 54*:453-460, Cell Press (1988).

Maniatis, T., et al., "Regulation of Inducible and Tissue-Specific Gene Expression," *Science 236*:1237-1245, American Association for the Advancement of Science (1987).

Mendiola, M.W., and de la Cruz, F., "Specificity of insertion of IS91, an insertion sequence present in a-haemolysin plasmids of *Escherichia coli*," *Mol. Microbiol. 3*:979-984, Blackwell Scientific Publications (1989).

Mercier, J., et al., "Structural and Functional Characterization of *tnpI*, a Recombinase Locus in Tn21 and Related b-Lactamase Transposons," *J. Bacteriol. 172*:3745-3757, American Society for Microbiology (1990).

Metcalf, W.W., et al., "Conditionally Replicative and Conjugative Plasmids Carrying *lacZa* for Cloning, Mutagenesis, and Allele Replacement in Bacteria," *Plasmid 35*:1-13, Academic Press (1996).

Mette, M.F., et al., "Transcriptional silencing and promoter methylation triggered by double-stranded RNA," *EMBO J. 19*:5194-5201, Oxford University Press (2000).

Meyer-Leon, L., et al., "Purfication of the FLP site-specific recombinase by affinity chromatography and re-examination of basic properties of the system," *Nucl. Acids Res. 15*:6469-6488, IRL Press Limited (1987).

Miller, H.i., et al., "*int*-h: an *int* Mutation of Phage λ That Enhances Site-Specific Recombination," *Cell* 20: 721-729, The MIT Press (1980).

Mizushima, S., and Nagat, S., "pEF-BOS, a powerful mammalian expression vector," *Nucl. Acids Res.* 18:5322, Oxford University Press (1990).

Nagy, A., "Cre Recombinase: The Universal Reagent for Genome Tailoring," *Genesis* 26:99-109, Wiley-Liss (2000).

Nash, H.A., and Robertson, C.A., "Purification and Properties of the *Escherichia coli* Protein Factor Required for λ Integrative Recombination," *J. Biol. Chem.* 256:9246-9253, The American Society of Biological Chemists (1981).

Odell, J.T., et al., "Seed-Specific Gene Activation Mediated by the Cre/lox Site-Specific Recombination System," *Plant Physiol.* 106:447-458, American Society of Plant Physiologists (Oct. 1994).

O'Gara, J.P., et al., "Identification and Molecular Genetic Analysis of Multiple Loci Contributing to High-Level Tellurite Resistance in *Rhodobacter sphaeroides* 2.4.1," *Appl. Environ. Microbiolol.* 63:4713-4720, American Society for Microbiology (1985).

Okayama, H., and Berg, P., "Bacteriophage Lambda Vector for Transducing a cDNA Clone Library into Mammalian Cells," *Mol. Cell. Biol.* 5:1136-1142, American Society for Microbiology (1985).

Osuna, R., et al., "Identification of two functional regions in Fis: the N-terminus is required to promote Hin-mediated DNA inversion by not λ excision," *EMBO J.* 10:1593-1603, Oxford University Press (1991).

Pal, S.K., et al., "P1 Plasmid Replication. Role of Initiator Titration in Copy Number Control," *J. Mol. Biol.* 192:275-285, Academic Press (1986).

Panke, S., et al., "Engineering of Quasi-Natural *Pseudomonas putida* Strains for Toluene Metabolism through an *ortho*-Cleavage Degradation Rathway," *Appl. Environ. Microbiol.* 64:748-751, American Society for Microbiology (1998).

Patel, P.H., and Loeb, L.A., "DNA polymerase active site is highly mutable: Evolutionary consequences," *Proc. Natl. Acad. Sci. USA* 97:5095-5100, National Academy of Sciences (2000).

Perler, F.B., "InBase, the New England Biolabs Intein Database," *Nucl. Acids Res.* 27:346-347, Oxford University Press (1999).

Persson, M.A.A., "Combinatorial Libraries," *Intern. Rev. Immunol.* 10:153-63, Harwood Academic Publishers GmbH (1993).

Phillips-Jones, M.K., et al., "Context Effects on Misreading and Suppression at UAG Codons in Human Cells," *Mol. Cell. Biol.* 15:6593-6600, American Society for Microbiology (Dec. 1995).

Powell, J., "Enhanced concatemer cloning-a modification to the SAGE (Serial Analysis of Gene Expression) technique," *Nucl. Acids Res.* 26:3445-3446, Oxford University Press (1998).

Prieto, M.A., et al., "Molecular Characterization of the 4-Hydroxyphenylacetate Catabolic Pathway of *Escherichia coli* W: Engineering a Mobile Aromatic Degradative Cluster," *J. Bacteriol.* 178:111-120, American Society for Microbiology (1996).

Qin, M., et al., "Site-specific cleavage of chromosomes in vitro through Cre-lox recombination," *Nucl. Acids Res.* 23:1923-1927, Oxford University Press (Jun. 1995).

Ross, W., and Landy, A., "Patterns of λ Int Recognition in the Regions of Strand Exchange," *Cell* 33:261-272, The MIT Press (1983).

Sambrook, J., et al., *Molecular Cloning: A Laboratory Manual, 2nd ed.*, Cold Spring Harbor Laboratory Press, New York, NY, pp. 16.6-16.8, (1989).

Sandhu, J.S., "Protein Engineering of Antibodies," *Crit. Rev. Biotechnol.* 12:437-462, CRC Press, Inc. (1992).

Sato, T., et al., "The *cisA* Cistron of *Bacillus subtilis* Sporulation Gene *spoIVC* Encodes a Protein Homologous to a Site-Specific Recombinase," *J. Bacteriol.* 172:1092-1098, American Society for Microbiology (1990).

Sauer, B., et al., "Construction of Isogenic Cell Lines Expressing Human and Rat Angiotensin II $AT_1$ Receptors by Cre-Mediated Site-Specific Recombination," *Methods: A Companion to Methods in Enzymology* 4:143-149, Academic Press (1992).

Sauer, B., and Henderson, N., "Site-specific DNA recombination in mammalian cells by the Cre recombinase of bacteriophage P1," *Proc. Natl. Acad. Sci. USA* 85: 5166-5170, National Academy of Sciences (1988).

Sauer, B., "Expression and Functioning in Yeast of a Bacterial Site Specific Recombination System," *J. Cell. Bio. Chem. Supp.* 10(b): 242, abs. No. I340, Alan R. Liss, Inc. (1986).

Schild, D., et al., "Cloning of three human multifunction de *novo* purine biosynthetic genes by functional complementation of yeast mutations," *Proc. Natl. Acad. Sci. USA* 87:2916-2920, National Academy of Sciences (1990).

Schnepf, E., et al., "*Bacillus thuringiensis* and Its Pesticidal Crystal Proteins," *Microbiol. Mol. Biol. Rev.* 62:775-806, American Society for Microbiology (1998).

Scott, S.D. and Marples, B., "Comment on the use of the cre/*lox*P recombinase system for gene therapy vectors," *Gene Therapy* 7:1706, Macmillan Publishers Ltd. (2000).

Segall, A. M., et al., "Architectural elements in nucleoprotein complexes: interchangeability of specific and non-specific DNA binding proteins," *EMBO J.* 13:4536-4548, Oxford University Press (Oct. 1994).

Shim, J., et al., "Distinct and Redundant Functions of µ1 Medium Chains of the AP-1 Clathrin-Associated Protein Complex in the Nematode *Caenorhabditis elegans*," *Mol. Biol. Cell* 11:2743-2756, American Society for Biology (2000).

Skraly, F.A., et al., "Construction and Characterization of a 1,3-Propanediol Operon," *Appl. Environ. Microbiol.* 64:98-105, American Society for Microbiology (1998).

Spinella, D.G., et al., "Tandem arrayed ligation of expressed sequence tags (TALEST): a new method for generating global gene expression profiles," *Nucl. Acids Res.* 27(e22):i-viii, Oxford University Press (1999).

Stark, W.M., et al., "Site-Specific Recombination by Tn3 Resolvase: Topological Changes in the Forward and Reverse Reactions," *Cell* 58:779-790, Cell Press (1989).

Stassi, D.L., et al., "Ethyl-substituted erythromycin derivatives producted by directed metabolic engineering," *Proc. Natl. Acad. Sci. USA* 95:7305-7309, National Academy of Sciences of the USA (1998).

Stellwagen, A.E., and Craig, N.L., "Mobile DNA elements: controlling transposition with ATP-dependent molecular switches," *Trends Biochem. Sci.* 23:486-490, Elsevier Science (1998).

Stenzel, T.T., et al., "The Integration Host Factor of *Escherichia coli* Binds to Bent DNA at the Origin of Replication of the Plasmid pSC101," *Cell* 49:709-717, Cell Press (1987).

Stryer, L., "The DNA Template Contains Stop Signals for transcription," in *Biochemistry*, 2nd ed., W.H. Freeman and Co., New York, NY, p. 610 (1981).

Sugiura, S., et al., "Minimal Essential Origin of Plasmid pSC101 Replication: Requirement of a Region Downstream of Iterons," *J. Bacteriol.* 175:5993-6001, American Society for Microbiology (1993).

Uetsuki, T., et al., "Isolation and Characterization of the Human Chromosomal Gene for Polypeptide Chain Elognation Factor-1a," *J. Biol. Chem.* 2645791-5798, The American Society for Biochemistry and Molecular Biology (1989).

van den Berg, A., et al., "Serial analysis of gene expression: rapid RT-PCR analysis of unknown SAGE tags," *Nucl. Acid Res.* 27(e17):i-iii, Oxford University Press (1999).

Vetter, D., et al., "Site-specific recombination of yeast 2-µm DNA in vitro," *Proc. Natl. Acad. Sci. USA* 80: 7284-7288, National Academy of Sciences (1983).

Voss, S.D., et al., "The role of enhancers in the regulation of cell-type-specific transcriptional control," *Trends Biochem. Sci.* 11:287-289, Elsevier Science (1986).

Voziyanov, Y., et al., "A general model for site-specific recombination by the integrase family recombinases," *Nucl. Acids Res.* 27:930-941, Oxford University Press (1999).

Yoon, H., et al., "SSL1, a suppressor fo a *HIS*4 5'-UTR stem-loop mutation, is essential for translation initiation and affects UV resistance in yeast," *Genes Dev.* 6:2463-2477, Cold Spring Harbor Laboratory Press (1992).

Amin, A.A., et al., "Synthesis of an Enzymatically Active FLP Recombinase In Vitro: Search for a DNA-Binding Domain," *Molec. Cell. Biol.* 9: 1987-1995, American Society for Microbiology (1989).

Bliska, J.B and Cozzarelli, N.R., "Use of Site-Specific Recombination as a Probe of DNA Structure and Metabolism in Vivo," *J. Molec. Biol. 194*:205-218, Academic Press Inc. (1987).

Chatterjee, P.K. and Sternberg, N.L., "Retrofitting High Molecular Weight DNA Cloned in P1: Introduction of Reporter Genes, Markers Selectable in Mammalian Cells and Generation of Nested Deletions," *Genet. Anal.: Biomolec. Eng. 13*:33-42, Elsevier Science B.V. (Jul. 1996).

Huang, L.-C., et al., "A bacterial model system for chromosomal targeting," *Nucl. Acids Res. 19*:443-448, Oxford University Press (1991).

Kanegae, Y., et al., "Efficient gene activation in mammalian cells by using recombinant adenovirus expressing site-specific Cre recombinase," *Nucl. Acids Res. 23*:3816-3821, Oxford University Press (Oct. 1995).

Lieber, A., et al., "Recombinant Adenoviruses with Large Deletions Generated by Cre-Mediated Excision Exhibit Different Biological Properties Compared with First-Generation Vectors In Vitro and In Vivo," *J. Virol. 70*:8944-8960, American Society for Microbiology (Dec. 1996).

Liu, X. and Gorovsky, M.A., "Mapping the 5' and 3' Ends of *Tetrahymena thermophelia* mRNAs Using RNA Ligase Mediated Amplification of cDNA Ends (RLM-Race)," *Nucl. Acids Res.* 21:4954-4960, Oxford University Press (1993).

Wang, Y. et al., "Targeted DNA recombination in vivo using an adenovirus carrying the cre recombinase gene," *Proc. Natl. Acad. Sci. USA 93*:3932-3936, National Academy of Science (Apr. 1996).

U.S. Appl. No. 11/106,715, Byrd et al., filed Apr. 15, 2005.

U.S. Appl. No. 11/249,274, Hartley et al., filed Oct. 14, 2005.

U.S. Appl. No. 11/251,821, Brasch et al., filed Oct. 18, 2005.

Ball, C.A., and Johnson, R.C., "Efficient Excision of Phage λ from the *Escherichia coli* Chromosome Requires the Fis Protein," *J. Bacteriol. 173*: 4027-4031, American Society for Microbiology (Jul. 1991).

Institut Pasteur Website, Introduction: http://www.pasteur.fr/recherche/unites/pmtg/integ/intro.html, accessed Jun. 19, 2003.

Institut Pasteur Website, Figure 1: http://www.pasteur.fr/recherche/unites/pmtg/integ/fig1.html, accessed Jun. 19, 2003.

Institut Pasteur Website, Figure 2: http://www.pasteur.fr/recherche/unites/pmtg/integ/fig2.html, accessed Jun. 19, 2003.

Institut Pasteur Website, Figure 3: http://www.pasteur.fr/recherche/unites/pmtg/integ/fig3.html, accessed Jun. 19, 2003.

Institut Pasteur Website, Main Page: http://www.pasteur.fr/recherche/unites/pmtg, accessed Jun. 19, 2003.

Kuempel, P., et al., "Use of a transposon (Tn*dif*) to obtain suppressing and nonsuppressing insertions of the *dif* resolvase site of *Eschericia coli*," *Genes & Development 10*:1162-1171, Cold Spring Harbor Laboratory Press (May 1, 1996).

Lee, M.H., et al., "Site-specific integration of mycobacteriophage L5: Integration-proficient vectors for *Mycobacterium smegmatis, Mycobacterium tuberculosis*, and baciller Calmette-Guérin," *Proc. Natl. Acad. Sci. USA 88*:3111-3115, National Academy of Sciences (1991).

Lenski, R.E., et al., "Genetic Analysis of a Plasmid-Encoded, Host Genotype-Specific Enhancement of Bacterial Fitness," *J. Bacteriol. 176*:3140-3147, American Society For Microbiology (1994).

Manning, P.A., et al., "Gene Capture in *Vibrio cholera*," *Trends in Microbiology 7*:93-95, Elsevier Science (1999).

Shuman, S., "Novel Approach to Molecular Cloning and Polynucleotide Synthesis Using Vaccinia DNA Topoisomerase," *J. Biol. Chem. 269*:32678-32684, American Society for Biochemistry and Molecular Biology, Inc. (1994).

Stuurman, J., et al., "Single-site manipulation of tomato choromosomes in vitro and in vivo using Cre-*lox* site-specific recombination," *Plant Molecular Biology 32*:901-913, Kluwer Academic Publishers (Nov. 27, 1996).

Zechiedrich, E.L., et al., "Topoisomerase IV, not gyrase, decatenates products of site-specific recombination in *Escherichia coli,*" *Genes Dev. 11*:2580-2592, Cold Spring Harbor Laboratory Press (1997).

Agah, R., et al., "Gene Recombination in Postmitotic Cells. Targeted Expression of Cre Recombinase Provokes Cardiac-restricted, Site-specific Rearrangement in Adult Ventricular Muscle In Vivo," *J. Clin. Invest. 100*:169-179, The American Society for Clinical Investigation, Inc. (Jul. 1997).

Baum, J.A., "Tn*5401*, a New Class II Transposable Element from *Bacillus thuringiensis,*" *Bacteriol. 176*:2835-2845, American Society for Microbiology (1994).

Benoist, C. and Chambon, P., "In vivo sequence requirements of the SV40 early promoter region," *Nature 290*:304-310, Macmillan Journals, Ltd. (1981).

Botstein, D., et al., "Making Mutations In Vitro and Putting Them Back Into Yeast," in *From Gene to Protein: Translation into Biotechology*, Ahmad, F., et al., eds., Academic Press, New York, NY pp. 265-274 (1982).

Broach, J.R., "The Yeast Plasmid 2μ Circle," *Cell 28*:203-204, MIT (1982).

Cenatiempo, Y., "Prokaryotic gene expression in vitro: transcription-translation coupled systems," *Biochimie 68*:505-515, Elsevier (1986).

Christiansen, B., et al., "A Resolvase-Like Protein Is Required for the Site-Specific Integration of the Temperate Lactococcal Bacteriophage TP901-1," *J. Bacteriol. 178*:5164-5173, American Society for Microbiology (Sep. 1996).

Crellin, P.K. and Rood, J.I., "The Resolvase/Invertase Domain of the Site-Specific Recombinase TnpX Is Functional and Recognizes a Target Sequence That Resembles the Junction of the Circular Form of the *Clostridum perfringens* Transposon Tn*4451,*" *J. Bacteriol. 179*:5148-5156, American Society for Microbiology (Aug. 1997).

Ferrin, L.J. and Camerini-Otero, R.D., "Sequence-specific ligation of DNA using RecA protein," *Proc. Natl. Acad. Sci. USA 95*:2152-2157, National Academy of Science (Mar. 1998).

Golic, K.G. and Golic, M.M., "Engineering the Drosophilia Genome: Chromosome Rearrangements by Design," *Genetics 144*:1693-1711, The Genetics Society of American (1996).

Gottesman, S., "Bacterial Regulation: Global Regulatory Networks," *Ann. Rev. Genet. 18*:415-441, Annual Reviews, Inc. (1984).

Guo, F., et al., "Structure of Cre recombinase complexed with DNA in a site-specific recombination synapse," *Nature 389*:40-46, Nature Publishing Group (Sep. 1997).

Hallet, B. and Sherratt, D.J., "Transposition and site-specific recombination: adapting DNA cut-and-paste mechanisms to a variety of genetic rearrangements," *FEMS Microbiol. Rev. 21*:157-178, Elsevier Science B.V. (Sep. 1997).

Harner, D.H. and Walling, M., "Regulation In Vivo of a Cloned Mammalian Gene: Cadmium Induces the Transcription of a Mouse Metallothionein Gene in SV40 Vectors," *J. Mol. Appl. Genet. 1*:273-288, Raven Press (1982).

Hanks, S.K. and Hunter, T., "The eukaryotic protein kinase superfamily: kinase (catalytic) domain structure and classification," *FASEB J. 9*:576-596, The Federation of American Societies for Experimental Biology (May 1995).

Hartley, J.L., et al., "DNA Cloning Using In Vitro Site-Specific Recombination," *Genome Res. 10*:1788-1795, Cold Spring Harbor Laboratory Press (Nov. 2000).

Heyman, J.A., et al., "Genome-Scale Cloning and Expression of Individual Open Reading Frames Using Topoisomerase I-Mediated Ligation," *Genome Res. 9*:383-392, Cold Spring Harbor Laboratory Press (Apr. 1999).

Huang, L-C., et al., "Convenient and Reversible Site-Specific Targeting of Exogenous DNA into a Bacterial Chromosome by Use of the FLP Recombinase: the FLIRT System," *J. Bacteriol. 179*:6076-6083, American Society for Microbiology (Oct. 1997).

John, Jr., J.F. and Twitty, J.A., "Plasmids as Epidemiologic Markers in Nosocomial Gram-Negative Bacilli: Experience at a University and Review of the Literature," *Rev. Infect. Dis. 8*:693-704, University of Chicago (1986).

Johnston, S.A. and Hopper, J.E., "Isolation of the yeast regulatory gene *GAL4* and analysis of its dosage effects on the galactose/melibiose regulon," *Proc. Natl. Acad. Sci. USA 79*:6971-6975, National Academy of Sciences (1982).

Kendall, K.J. and Cohen, S.N., "Plasmid Transfer in *Streptomyces lividans*: Identification of a *kil-kor* System Associated with the Transfer Region of pIJ101," *J. Bacteriol. 169*:4177-4183, American Society for Microbiology (1987).

Lyznik, L.A., et al., "Activity of yeast FLP recombinase in maize and rice photoplasts," *Nucleic Acids Res. 21*:969-975, Oxford University Press (1993).

Maniatis, T., "Recombinant DNA Procedures in the Study of Eukaryotic Genes," in *Cell Biology: A Comprehensive Treatise, vol. 3, Gene Expression: The Production of RNA's*, Goldstein, L., and Prescott, D.M., eds., Academic Press, Inc., New York, NY, pp. 563-608 (1980).

Mayer, B.J. and Baltimore, D., "Signalling through SH2 and SH3 domains," *Trends Cell Biol. 3*:8-13, Elsevier Science (1993).

McKnight, S.L., "Functional Relationships between Transcriptional Control Signals of the Thymidine Kinase Gene of Herpes Simplex Virus," *Cell 31*:355-365, MIT (1982).

Nunes-Düby, S.E., et al., "λ Integrase cleaves DNA *in cis,*" *EMBO J. 13*:4421-4430, Oxford University Press (1994).

Odell, J., et al., "Site-directed recombination in the genome of transgenic tobacco," *Mol. Gen. Genet. 223*:369-378, Springer-Verlag (1990).

Peterson, B.Ø. and Shuman, S., "Histidine 265 Is Important for Covalent Catalysis by Vaccinia Topisomerase and Is Conserved in All Eukaryotic Type I Enzymes," *J. Biol. Chem. 272*:3891-3896, The American Society for Biochemistry and Molecular Biology, Inc. (Feb. 1997).

Rausch, H. and Lehmann, M., "Structural analysis of the actinophage ΦC31 attachment site," *Nucleic Acids Res. 19*:5187-5189, IRL Press (1991).

Russell, M., "A recombination-based cloning system that decreases time to protein analysis," *Am. Biotechnol. Lab. 18*:8,10, International Scientific Communications, Inc. (Jun. 2000).

Sadowski, I., et al., "A Noncatalytic Domain Conserved among Cytoplasmic Protein-Tyrosine Kinases Modifies the Kinase Function and Transforming Acitivity of Fujinami Sarcoma Virus P130*gag-fps*," *Mol. Cell. Biol. 6*:4396-4408, American Society for Microbiology (1986).

Sauer, B. and Henderson, N., "Targeted Insertion of Exogenous DNA into the Eukaryotic Genome by the Cre Recombinase," *New Biol. 2*:441-449, Saunders Scientific Publications/W.B. Saunders Company (1990).

Senecoff, J.F., et al., "The FLP recombinase of the yeast 2-μm plasmid: Characterization of its recombination site," *Proc. Natl. Acad. Sci. USA 82*:7270-7274, National Academy of Science (1985).

Shaikh, A.C. and Sadowski, P.D., "The Cre Recombinase Cleaves the *lox* Site in *trans,*" *J. Biol. Chem. 272*:5695-5702, The American Society for Biochemistry and Molecular Biology, Inc. (Feb. 1997).

Shirai, M., et al., "Site-Specific Integration of the Actinophage R4 Genome into the Chromosome of *Streptomyces parvulus* upon Lysogenization," *J. Bacteriol. 173*:4237-4239, American Society for Microbiology (1991).

Short, J.M., et al., "80 ZAP: a bacteriophage λ expression vector with in vivo excision properties," *Nucleic Acids Res. 16*:7583-7600, Oxford University Press (1988).

Shuman, S., et al., "Characterization of Vaccinia Virus DNA Topoisomerase I Expressed in *Escherichia coli,*" *J. Biol. Chem. 263*:16401-16407, The American Society for Biochemistry and Molecular Biology, Inc. (1988).

Shuman, S., "Site-specified Interaction of Vaccinia Virus Topiosomerase I with Duplex DNA. Minimal DNA Substrate for Strand Cleavage In Vitro," *J. Biol. Chem. 266*:11372-11379, The American Society for Biochemistry and Molecular Biology, Inc. (1991).

Shuman, S., "Erratum: Site-specific Interaction of Vaccinia Virus Topoisomerase I with Duplex DNA. Minimal DNA Substrate for Strand Cleave In Vitro," *J. Biol. Chem. 266*:20576-20577, The American Society for Biochemistry and Molecular Biology, Inc. (1991).

Silver, P.A., et al., "Amino termius of the yeast *GAL4* gene product is sufficient for nuclear localization," *Proc. Natl. Acad. Sci. USA 81*:5951-5955, National Academy of Sciences (1984).

Sinclair, B., "Honing Your Cloning," *The Scientist 14*:29-32, The Scientist Inc. (Aug. 21, 2000) available at: http://www.the-scientist.com/yr2000/aug/profile1_000821.html.

Stark, W.M., et al., "Catalysis by site-specific recombinases," *Trends Genet. 8*:432-439, Elsevier Science (1992).

Ulmanen, I., et al., "Transcription and Translation of Foreign Genes in *Bacillus subtilis* by the Aid of a Secretion Vector," *J. Bacteriol. 162*:176-182, American Society for Microbiology (1985).

van Deursen, J., et al., "Cre-mediated site-specific translocation between nonhomologous mouse chromosomes," *Proc. Natl. Acad. Sci. USA 92*:7376-7380, National Academy of Sciences (1995).

Ward, J.M., et al., "Construction and characterisation of a series of multi-copy promoter-probe plasmid vectors for *Streptomyces* using the aminoglycoside phosphotransferase gene from Tn5 as indicator," *Mol. Gen. Genet. 203*:468-478, Springer-Verlag (1986).

Invitrogen Life Technologies online catalog, "Directional TOPO Entry Vectors," 4 pages, accessed Sep. 27, 2002, available at: http://www.invitrogen.com/content.cfm?pageid=3799 &cfid=2897960&cftoken=88086554.

Invitrogen Online Catalog, "The Echo™ Cloning System: The Future of Cloning is Here," available at: http://web.archive.org/web/20010112191100/www.invitrogen.com/catalog_project/cat_echo.html, accessed Jul. 7, 2004.

Invitrogen Online Catalog, "The Echo™ Cloning System: The Future of Cloning is Here," available at http://invitrogen.com/content.cfm?pageid=3371&cfid=16767784&cftoken=62396683, accessed Jul. 7, 2004.

Dialog File 351, Derwent World Patent Index, unverified English Language Abstract for French Patent No. FR 2 670 502 (Document AL20) and PCT Patent No. WO 92/10577 (Document AM20), WPI Accession No. 9107201.

Bruckner, R.C., and Cox, M.M., "The Histone-like H Protein of *Escherichia coli* is a ribosomal protein s3," *Nucl. Acids Res. 17*:3145-3161, Oxford University Press (1989).

Ohara, O., and Temple, G., "Directional cDNA library construction assisted by the in vitro recombination reaction," *Nucl. Acids Research 29*:e22(1-8). Oxford University Press (Feb. 2001).

* cited by examiner

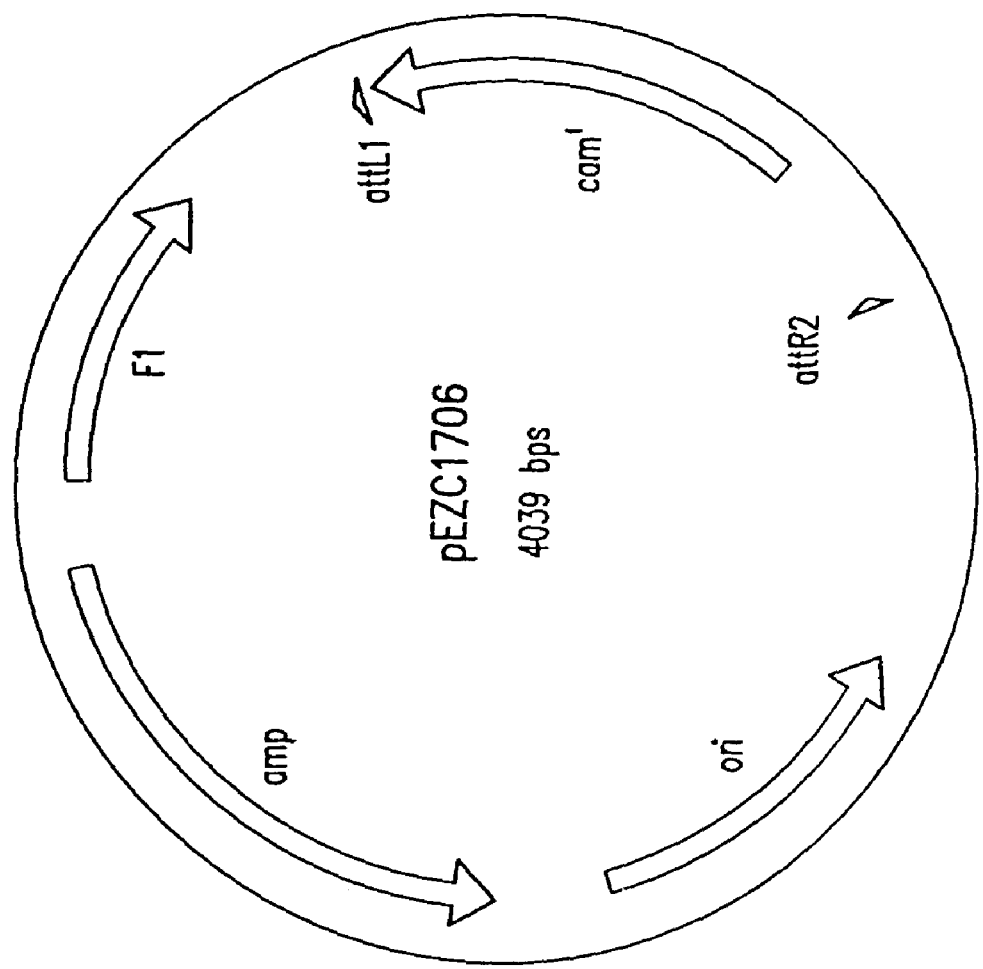

RECOMBINATIONAL CLONING USING ENGINEERED RECOMBINATION SITES

CROSS REFERENCE TO RELATED APPLICATIONS

The present application is a continuation of U.S. application Ser. No. 09/432,085, filed Nov. 2, 1999, which is a divisional of U.S. application Ser. No. 09/233,493, filed Jan. 20, 1999 (now U.S. Pat. No. 6,143,557), which is a continuation of U.S. application Ser. No. 08/663,002, filed Jun. 7, 1996 (now U.S. Pat. No. 5,888,732), which is a continuation-in-part of U.S. application Ser. No.08/486,139, filed Jun. 7, 1995 (now abandoned), which applications are entirely incorporated herein by reference.

BACKGROUND OF THE INVENTION

1. Field of the Invention

The present invention relates to recombinant DNA technology. DNA and vectors having engineered recombination sites are provided for use in a recombinational cloning method that enables efficient and specific recombination of DNA segments using recombination proteins. The DNAs, vectors and methods are useful for a variety of DNA exchanges, such as subcloning of DNA, in vitro or in vivo.

2. Related Art

Site specific recombinases. Site specific recombinases are enzymes that are present in some viruses and bacteria and have been characterized to have both endonuclease and ligase properties. These recombinases (along with associated proteins in some cases) recognize specific sequences of bases in DNA and exchange the DNA segments flanking those segments. The recombinases and associated proteins are collectively referred to as "recombination proteins" (see, e.g., Landy, A., *Current Opinion in Biotechnology* 3:699-707 (1993)).

Numerous recombination systems from various organisms have been described. See, e.g., Hoess et al., *Nucleic Acids Research* 14(6):2287 (1986); Abremski et al., *J. Biol. Chem.* 261(1):391 (1986); Campbell, *J. Bacteriol.* 174(23):7495 (1992); Qian et al., *J. Biol. Chem.* 267(11):7794 (1992); Araki et al., *J. Mol. Biol.* 225(1):25 (1992); Maeser and Kahnmann (1991) *Mol. Gen. Genet.* 230:170-176).

Many of these belong to the integrase family of recombinases (Argos et al. *EMBO J.* 5:433-440 (1986)). Perhaps the best studied of these are the Integrase/att system from bacteriophage λ (Landy, A. *Current Opinions in Genetics and Devel.* 3:699-707 (1993)), the Cre/loxP system from bacteriophage P1 (Hoess and Abremski (1990) In *Nucleic Acids and Molecular Biology*, vol. 4. Eds.: Eckstein and Lilley, Berlin-Heidelberg:Springer-Verlag; pp. 90-109), and the FLP/FRT system from the *Saccharomyces cerevisiae* 2μ circle plasmid (Broach et al. *Cell* 29:227-234 (1982)).

Backman (U.S. Pat. No. 4,673,640) discloses the in vivo use of λ recombinase to recombine a protein producing DNA segment by enzymatic site-specific recombination using wild-type recombination sites attB and attP.

Hasan and Szybalski (*Gene* 56:145-151 (1987)) discloses the use of λ Int recombinase in vivo for intramolecular recombination between wild type attP and attB sites which flank a promoter. Because the orientations of these sites are inverted relative to each other, this causes an irreversible flipping of the promoter region relative to the gene of interest.

Palazzolo et al. *Gene* 88:25-36 (1990), discloses phage lambda vectors having bacteriophage λ arms that contain restriction sites positioned outside a cloned DNA sequence and between wild-type loxP sites. Infection of *E. coli* cells that express the Cre recombinase with these phage vectors results in recombination between the loxP sites and the in vivo excision of the plasmid replicon, including the cloned cDNA.

Pósfai et al. (*Nucl. Acids Res.* 22:2392-2398 (1994)) discloses a method for inserting into genomic DNA partial expression vectors having a selectable marker, flanked by two wild-type FRT recognition sequences. FLP site-specific recombinase as present in the cells is used to integrate the vectors into the genome at predetermined sites. Under conditions where the replicon is functional, this cloned genomic DNA can be amplified.

Bebee et al. (U.S. Pat. No. 5,434,066) discloses the use of site-specific recombinases such as Cre for DNA containing two loxP sites is used for in vivo recombination between the sites.

Boyd (*Nucl. Acids Res.* 21:817-821 (1993)) discloses a method to facilitate the cloning of blunt-ended DNA using conditions that encourage intermolecular ligation to a dephosphorylated vector that contains a wild-type loxP site acted upon by a Cre site-specific recombinase present in *E. coli* host cells.

Waterhouse et al. (PCT No. 93/19172 and *Nucleic Acids Res.* 21 (9):2265 (1993)) disclose an in vivo method wherelight and heavy chains of a particular antibody were cloned in different phage vectors between loxP and loxP 511 sites and used to transfect new *E. coli* cells. Cre, acting in the host cells on the two parental molecules (one plasmid, one phage), produced four products in equilibrium: two different cointegrates (produced by recombination at either loxP or loxP 511 sites), and two daughter molecules, one of which was the desired product.

In contrast to the other related art, Schlake & Bode (*Biochemistry* 33:12746-12751 (1994)) discloses an in vivo method to exchange expression cassettes at defined chromosomal locations, each flanked by a wild type and a spacer-mutated FRT recombination site. A double-reciprocal crossover was mediated in cultured mammalian cells by using this FLP/FRT system for site-specific recombination.

Transposases. The family of enzymes, the transposases, has also been used to transfer genetic information between replicons. Transposons are structurally variable, being described as simple or compound, but typically encode the recombinase gene flanked by DNA sequences organized in inverted orientations. Integration of transposons can be random or highly specific. Representatives such as Tn7, which are highly site-specific, have been applied to the in vivo movement of DNA segments between replicons (Lucklow et al., *J. Virol.* 67:4566-4579 (1993)).

Devine and Boeke *Nucl. Acids Res.* 22:3765-3772 (1994), discloses the construction of artificial transposons for the insertion of DNA segments, in vitro, into recipient DNA molecules. The system makes use of the integrase of yeast TY1 virus-like particles. The DNA segment of interest is cloned, using standard methods, between the ends of the transposon-like element TY1. In the presence of the TY1 integrase, the resulting element integrates randomly into a second target DNA molecule.

DNA cloning. The cloning of DNA segments currently occurs as a daily routine in many research labs and as a prerequisite step in many genetic analyses. The purpose of these clonings is various, however, two general purposes can be considered: (1) the initial cloning of DNA from large DNA or RNA segments (chromosomes, YACs, PCR fragments, mRNA, etc.), done in a relative handful of known vectors such as pUC, pGem, pBlueScript, and (2) the subcloning of these DNA segments into specialized vectors for functional analysis. A great deal of time and effort is expended both in the initial cloning of DNA segments and in the transfer of DNA segments from the initial cloning vectors to the more specialized vectors. This transfer is called subcloning.

The basic methods for cloning have been known for many years and have changed little during that time. A typical cloning protocol is as follows:

(1) digest the DNA of interest with one or two restriction enzymes;
(2) gel purify the DNA segment of interest when known;
(3) prepare the vector by cutting with appropriate restriction enzymes, treating with alkaline phosphatase, gel purify etc., as appropriate;
(4) ligate the DNA segment to vector, with appropriate controls to estimate background of uncut and self-ligated vector;
(5) introduce the resulting vector into an *E. coli* host cell;
(6) pick selected colonies and grow small cultures overnight;
(7) make DNA minipreps; and
(8) analyze the isolated plasmid on agarose gels (often after diagnostic restriction enzyme digestions) or by PCR The specialized vectors used for subcloning DNA segments are functionally diverse. These include but are not limited to: vectors for expressing genes in various organisms; for regulating gene expression; for providing tags to aid in protein purification or to allow tracking of proteins in cells; for modifying the cloned DNA segment (e.g., generating deletions); for the synthesis of probes (e.g., riboprobes); for the preparation of templates for DNA sequencing; for the identification of protein coding regions; for the fusion of various protein-coding regions; to provide large amounts of the DNA of interest, etc. It is common that a particular investigation will involve subcloning the DNA segment of interest into several different specialized vectors.

As known in the art, simple subcloning can be done in one day (e.g., the DNA segment is not large and the restriction sites are compatible with those of the subcloning vector). However, many other subcloning can take several weeks, especially those involving unknown sequences, long fragments, toxic genes, unsuitable placement of restriction sites, high backgrounds, impure enzymes, etc. Subcloning DNA fragments is thus often viewed as a chore to be done as few times as possible.

Several methods for facilitating the cloning of DNA segments have been described, e.g., as in the following references.

Ferguson, J., et al. *Gene* 16:191 (1981), discloses a family of vectors for subcloning fragments of yeast DNA. The vectors encode kanamycin resistance. Clones of longer yeast DNA segments can be partially digested and ligated into the subcloning vectors. If the original cloning vector conveys resistance to ampicillin, no purification is necessary prior to transformation, since the selection will be for kanamycin.

Hashimoto-Gotoh, T., et al. *Gene* 41:125 (1986), discloses a subcloning vector with unique cloning sites within a streptomycin sensitivity gene; in a streptomycin-resistant host, only plasmids with inserts or deletions in the dominant sensitivity gene will survive streptomycin selection.

Accordingly, traditional subcloning methods, using restriction enzymes and ligase, are time consuming and relatively unreliable. Considerable labor is expended, and if two or more days later the desired subclone can not be found among the candidate plasmids, the entire process must then be repeated with alternative conditions attempted. Although site specific recombinases have been used to recombine DNA in vivo, the successful use of such enzymes in vitro was expected to suffer from several problems. For example, the site specificities and efficiencies were expected to differ in vitro; topologically-linked products were expected; and the topology of the DNA substrates and recombination proteins was expected to differ significantly in vitro (see, e.g., Adams et al., *J. Mol. Biol.* 226:661-73 (1992)). Reactions that could go on for many hours in vivo were expected to occur in significantly less time in vitro before the enzymes became inactive. Multiple DNA recombination products were expected in the biological host used, resulting in unsatisfactory reliability, specificity or efficiency of subcloning. In vitro recombination reactions were not expected to be sufficiently efficient to yield the desired levels of product.

Accordingly, there is a long felt need to provide an alternative subcloning system that provides advantages over the known use of restriction enzymes and ligases.

SUMMARY OF THE INVENTION

The present invention provides nucleic acid, vectors and methods for obtaining chimeric nucleic acid using recombination proteins and engineered recombination sites, in vitro or in vivo. These methods are highly specific, rapid, and less labor intensive than what is disclosed or suggested in the related background art. The improved specificity, speed and yields of the present invention facilitates DNA or RNA subcloning, regulation or exchange useful for any related purpose. Such purposes include in vitro recombination of DNA segments and in vitro or in vivo insertion or modification of transcribed, replicated, isolated or genomic DNA or RNA.

The present invention relates to nucleic acids, vectors and methods for moving or exchanging segments of DNA using at least one engineered recombination site and at least one recombination protein to provide chimeric DNA molecules which have the desired characteristic(s) and/or DNA segment(s). Generally, one or more parent DNA molecules are recombined to give one or more daughter molecules, at least one of which is the desired Product DNA segment or vector. The invention thus relates to DNA, RNA, vectors and methods to effect the exchange and/or to select for one or more desired products.

One embodiment of the present invention relates to a method of making chimeric DNA, which comprises
 (a) combining in vitro or in vivo
   (i) an Insert Donor DNA molecule, comprising a desired DNA segment flanked by a first recombination site and a second recombination site, wherein the first and second recombination sites do not recombine with each other;
   (ii) a Vector Donor DNA molecule containing a third recombination site and a fourth recombination site, wherein the third and fourth recombination sites do not recombine with each other; and
   (iii) one or more site specific recombination proteins capable of recombining the first and third recombinational sites and/or the second and fourth recombinational sites;
 thereby allowing recombination to occur, so as to produce at least one Cointegrate DNA molecule, at least one desired Product DNA molecule which comprises said desired DNA segment, and optionally a Byproduct DNA molecule; and then, optionally, (b) selecting for the Product or Byproduct DNA molecule.

Another embodiment of the present invention relates to a kit comprising a carrier or receptacle being compartmentalized to receive and hold therein at least one container, wherein a first container contains a DNA molecule comprising a vector having at least two recombination sites flanking a cloning site or a Selectable marker, as described herein. The kit optionally further comprises:
 (i) a second container containing a Vector Donor plasmid comprising a subcloning vector and/or a Selectable marker of which one or both are flanked by one or more engineered recombination sites; and/or
 (ii) a third container containing at least one recombination protein which recognizes and is capable of recombining at least one of said recombination sites.

Other embodiments include DNA and vectors useful in the methods of the present invention. In particular, Vector Donor molecules are provided in one embodiment, wherein DNA segments within the Vector Donor are separated either by, (i) in a circular Vector Donor, at least two recombination sites, or (ii) in a linear Vector Donor, at least one recombination site, where the recombination sites are preferably engineered to enhance specificity or efficiency of recombination.

One Vector Donor embodiment comprises a first DNA segment and a second DNA segment, the first or second segment comprising a Selectable marker. A second Vector Donor embodiment comprises a first DNA segment and a second DNA segment, the first or second DNA segment comprising a toxic gene. A third Vector Donor embodiment comprises a first DNA segment and a second DNA segment, the first or second DNA segment comprising an inactive fragment of at least one Selectable marker, wherein the inactive fragment of the Selectable marker is capable of reconstituting a functional Selectable marker when recombined across the first or second recombination site with another inactive fragment of at least one Selectable marker.

The present recombinational cloning method possesses several advantages over previous in vivo methods. Since single molecules of recombination products can be introduced into a biological host, propagation of the desired Product DNA in the absence of other DNA molecules (e.g., starting molecules, intermediates, and by-products) is more readily realized. Reaction conditions can be freely adjusted in vitro to optimie enzyme activities. DNA molecules can be incompatible with the desired biological host (e.g., YACs, genomic DNA, etc.), can be used. Recombination proteins from diverse sources can be employed, together or sequentially.

Other embodiments will be evident to those of ordinary skill in the art from the teachings contained herein in combination with what is known to the art.

BRIEF DESCRIPTION OF THE FIGURES

FIG. 6B depicts a vector diagram of pEZC1706.

DETAILED DESCRIPTION OF THE PREFERRED EMBODIMENTS

It is unexpectedly discovered in the present invention that subcloning reactions can be provided using recombinationl cloning. Recombination cloning according to the present invention uses DNAs, vectors and methods, in vitro and in vivo, for moving or exchanging segments of DNA molecules using engineered recombination sites and recombination proteins. These methods provide chimeric DNA molecules that have the desired characteristic(s) and/or DNA segment(s).

The present invention thus provides nucleic acid, vectors and methods for obtaining chimeric nucleic acid using recombination proteins and engineered recombination sites, in vitro or in vivo. These methods are highly specific, rapid, and less labor intensive than what is disclosed or suggested in the related background art. The improved specificity, speed and yields of the present invention facilitates DNA or RNA subcloning, regulation or exchange useful for any related purpose. Such purposes include in vitro recombination of DNA segments and in vitro or in vivo insertion or modification of transcribed, replicated, isolated or genomic DNA or RNA.

Definitions

In the description that follows, a number of terms used in recombinant DNA technology are utilized extensively. In order to provide a clear and consistent understanding of the specification and claims, including the scope to be given such terms, the following definitions are provided.

Byproduct: is a daughter molecule (a new clone produced after the second recombination event during the recombinational cloning process) lacking the DNA which is desired to be subcloned.

Cointegrate: is at least one recombination intermediate DNA molecule of the present invention that contains both parental (starting) DNA molecules. It will usually be circular. In some embodiments it can be linear.

Host: is any prokaryotic or eukaryotic organism that can be a recipient of the recombinational cloning Product. A "host," as the term is used herein, includes prokaryotic or eukaryotic organisms that can be genetically engineered. For examples of such hosts, see Maniatis et al., *Molecular Cloning: A Laboratory Manual*, Cold Spring Harbor Laboratory, Cold Spring Harbor, N.Y. (1982).

Insert: is the desired DNA segment (segment A of FIG. 1) which one wishes to manipulate by the method of the present invention. The insert can have one or more genes.

Insert Donor: is one of the two parental DNA molecules of the present invention which carries the Insert. The Insert Donor DNA molecule comprises the Insert flanked on both sides with recombination signals. The Insert Donor can be linear or circular. In one embodiment of the invention, the Insert Donor is a circular DNA molecule and further comprises a cloning vector sequence outside of the recombination signals (see FIG. 1).

Figure 1:
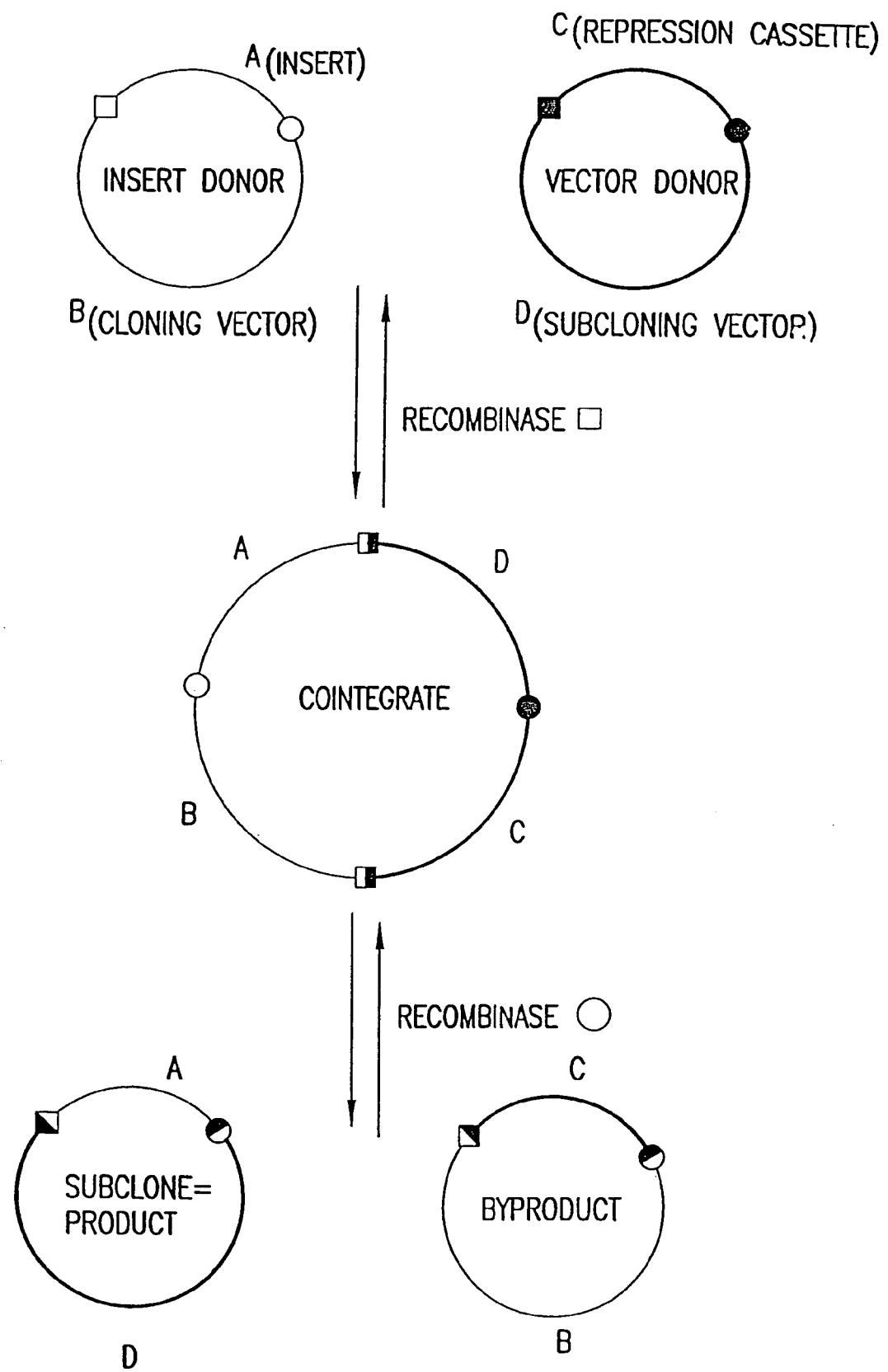
FIG. 1 depicts one general method of the present invention, wherein the starting (parent) DNA molecules can be circular or linear. The goal is to exchange the new subcloning vector D for the original cloning vector B. It is desirable in one embodiment to select for AD and against all the other molecules, including the Cointegrate. The square and circle are sites of recombination: e.g., loxP sites, att sites, etc. For example, segment D can contain expression signals, new drug markers, new origins of replication, or specialized functions for mapping or sequencing DNA.

Product: is one or both the desired daughter molecules comprising the A and D or B and C sequences which are produced after the second recombination event during the recombinational cloning process (see FIG. 1). The Product contains the DNA which was to be cloned or subcloned.

Promoter: is a DNA sequence generally described as the 5'-region of a gene, located proximal to the start codon. The transcription of an adjacent DNA segment is initiated at the promoter region A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Recognition sequence: Recognition sequences are particular DNA sequences which a protein, DNA, or RNA molecule (e.g., restriction endonuclease, a modification methylase, or a recombinase) recognizes and binds. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., *Current Opinion in Biotechnology* 5:521-527 (1994). Other examples of recognition sequences are the attB, attP, attL, and attR sequences which are recognized by the recombinase enzyme λ Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins IHF, FIS, and Xis. See Landy, *Current Opinion in Biotechnology* 3:699-707 (1993). Such sites are also engineered according to the present invention to enhance methods and products.

Recombinase: is an enzyme which catalyzes the exchange of DNA segments at specific recombination sites.

Recombinational Cloning: is a method described herein, whereby segments of DNA molecules are exchanged, inserted, replaced, substituted or modified, in vitro or in vivo.

Recombination proteins: include excisive or integrative proteins, enzymes, co-factors or associated proteins that are involved in recombination reactions involving one or more recombination sites. See, Landy (1994), infra.

Repression cassette: is a DNA segment that contains a repressor of a Selectable marker present in the subcloning vector.

Selectable marker: is a DNA segment that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of Selectable markers include but are not limited to: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as β-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1-5 above (e.g., antisense oligonucleotides); (7) DNA segments that bind products that modify a substrate (e.g. restriction endonucleases); (8) DNA segments that can be used to isolate a desired molecule (e.g. specific protein binding sites); (9) DNA segments that encode a specific nucleotide sequence which can be otherwise non-functional (e.g., for PCR amplification of subpopulations of molecules); and/or (10) DNA segments, which when absent, directly or indirectly confer sensitivity to particular compounds.

Selection scheme: is any method which allows selection, enrichment, or identification of a desired Product or Product(s) from a mixture containing the Insert Donor, Vector Donor, and/or any intermediates, (e.g. a Cointegrate) Byproducts. The selection schemes of one preferred embodiment have at least two components that are either linked or unlinked during recombinational cloning. One component is a Selectable marker. The other component controls the expression in vitro or in vivo of the Selectable marker, or survival of the cell harboring the plasmid carrying the Selectable marker. Generally, this controlling element will be a repressor or inducer of the Selectable marker, but other means for controlling expression of the Selectable marker can be used. Whether a repressor or activator is used will depend on whether the marker is for a positive or negative selection, and the exact arrangement of the various DNA segments, as will be readily apparent to those skilled in the art A preferred requirement is that the selection scheme results in selection of or enrichment for only one or more desired Products. As defined herein, to select for a DNA molecule includes (a) selecting or enriching for the presence of the desired DNA molecule, and (b) selecting or enriching against the presence of DNA molecules that are not the desired DNA molecule.

In one embodiment, the selection schemes (which can be carried out reversed) will take one of three forms, which will be discussed in terms of FIG. 1. The first, exemplified herein with a Selectable marker and a repressor therefor, selects for molecules having segment D and lacking segment C. The second selects against molecules having segment C and for molecules having segment D. Possible embodiments of the second form would have a DNA segment carrying a gene toxic to cells into which the in vitro reaction products are to be introduced. A toxic gene can be a DNA that is expressed as a toxic gene product (a toxic protein or RNA), or can be toxic in and of itself. (In the latter case, the toxic gene is understood to carry its classical definition of "heritable trait".)

Examples of such toxic gene products are well known in the art, and include, but are not limited to, restriction endonucleases (e.g., DpnI) and genes that kill hosts in the absence of a suppressing function, e.g., kicB. A toxic gene can alternatively be selectable in vitro, e.g., a restriction site.

In the second form, segment D carries a Selectable marker. The toxic gene would eliminate transformants harboring the Vector Donor, Cointegrate, and Byproduct molecules, while the Selectable marker can be used to select for cells containing the Product and against cells harboring only the Insert Donor.

The third form selects for cells that have both segments A and D in cis on the same molecule, but not for cells that have both segments in trans on different molecules. This could be embodied by a Selectable marker that is split into two inactive fragments, one each on segments A and D.

The fragments are so arranged relative to the recombination sites that when the segments are brought together by the recombination event, they reconstitute a functional Selectable marker. For example, the recombinational event can link a promoter with a structural gene, can link two fragments of a structural gene, or can link genes that encode a heterodimeric gene product needed for survival, or can link portions of a replicon.

Site-specific recombinase: is a type of recombinase which typically has at least the following four activities: (1) recognition of one or two specific DNA sequences; (2) cleavage of said DNA sequence or sequences; (3) DNA topoisomerase activity involved in strand exchange; and (4) DNA ligase activity to reseal the cleaved strands of DNA. See Sauer, B., Current Opinions in Biotechnology 5:521-527 (1994). Conservative site-specific recombination is distinguished from homologous recombination and transposition by a high degree of specificity for both partners. The strand exchange mechanism involves the cleavage and rejoining of specific DNA sequences in the absence of DNA synthesis (Landy, A. (1989) Ann Rev. Biochem. 58:913-949).

Subcloning vector: is a cloning vector comprising a circular or linear DNA molecule which includes an appropriate replicon. In the present invention, the subcloning vector (segment D in FIG. 1) can also contain functional and/or regulatory elements that are desired to be incorporated into the final product to act upon or with the cloned DNA Insert (segment A in FIG. 1). The subcloning vector can also contain a Selectable marker (contained in segment C in FIG. 1).

Vector: is a DNA that provides a useful biological or biochemical property to an Insert. Examples include plasmids, phages, and other DNA sequences which are able to replicate or be replicated in vitro or in a host cell, or to convey a desired DNA segment to a desired location within a host cell. A Vector can have one or more restriction endonuclease recognition sites at which the DNA sequences can be cut in a determinable fashion without loss of an essential biological function of the vector, and into which a DNA fragment can be spliced in order to bring about its replication and cloning. Vectors can further provide primer sites, e.g., for PCR, transcriptional and/or translational initiation and/or regulation sites, recombinational signals, replicons, Selectable markers, etc. Clearly, methods of inserting a desired DNA fragment which do not require the use of homologous recombination or restriction enzymes (such as, but not limited to, UDG cloning of PCR fragments (U.S. Pat. No. 5,334,575, entirely incorporated herein by reference), T:A cloning, and the like) can also be applied to clone a fragment of DNA into a cloning vector to be used according to the present invention. The cloning vector can further contain a Selectable marker suitable for use in the identification of cells transformed with the cloning vector.

Vector Donor: is one of the two parental DNA molecules of the present invention which carries the DNA segments encoding the DNA vector which is to become part of the desired Product. The Vector Donor comprises a subcloning vector D (or it can be called the cloning vector if the Insert Donor does not already contain a cloning vector) and a segment C flanked by recombination sites (see FIG. 1). Segments C and/or D can contain elements that contribute to selection for the desired Product daughter molecule, as described above for selection schemes. The recombination signals can be the same or different, and can be acted upon by the same or different recombinases. In addition, the Vector Donor can be linear or circular.

Description

One general scheme for an in vitro or in vivo method of the invention is shown in FIG. 1, where the Insert Donor and the Vector Donor can be either circular or linear DNA, but is shown as circular. Vector D is exchanged for the original cloning vector A. It is desirable to select for the daughter vector containing elements A and D and against other molecules, including one or more Cointegrate(s). The square and circle are different sets of recombination sites (e.g., lox sites or att sites). Segment A or D can contain at least one Selection Marker, expression signals, origins of replication, or specialized functions for detecting, selecting, expressing, mapping or sequencing DNA, where D is used in this example.

Examples of desired DNA segments that can be part of Element A or D include, but are not limited to, PCR products, large DNA segments, genomic clones or fragments, cDNA clones, functional elements, etc., and genes or partial genes, which encode useful nucleic acids or proteins. Moreover, the recombinational cloning of the present invention can be used to make ex vivo and in vivo gene transfer vehicles for protein expression and/or gene therapy.

In FIG. 1, the scheme provides the desired Product as containing vectors D and A, as follows. The Insert Donor (containing A and B) is first recombined at the square recombination sites by recombination proteins, with the Vector Donor (containing C and D), to form a Co-integrate having each of A-D-C-B. Next, recombination occurs at the circle recombination sites to form Product DNA (A and D) and Byproduct DNA (C and B). However, if desired, two or more different Co-integrates can be formed to generate two or more Products.

In one embodiment of the present in vitro or in vivo recombinational cloning method, a method for selecting at least one desired Product DNA is provided. This can be understood by consideration of the map of plasmid pEZC726 depicted in FIG. 2. The two exemplary recombination sites are attP and loxP. On one segment defined by these sites is a kanamycin resistance gene whose promoter has been replaced by the tetOP operator/promoter from transposon Tn 10. In the absence of tet repressor protein, E. coli RNA polymerase transcribes the kanamycin resistance gene from the tetOP. If tet repressor is present, it binds to tetOP and blocks transcription of the kanamycin resistance gene. The other segment of pEZC726 has the tet repressor gene expressed by a constitutive promoter. Thus cells transformed by pEZC726 are resistant to chloramphenicol, because of the chloramphenicol acetyl transferase gene on the same segment as tetR, but are sensitive to kanamycin. The recombination reactions result in separation of the tetR gene from the regulated kanamycin resistance gene. This separation results in kanamycin resistance in cells receiving the desired recombination Product.

Two different sets of plasmids were constructed to demonstrate the in vitro method. One set, for use with Cre recombinase only (cloning vector 602 and subcloning vector 629 (FIG. 3)) contained loxP and loxP 511 sites. A second set, for use with Cre and integrase (cloning vector 705 and subcloning vector 726 (FIG. 2)) contained loxP and att sites. The efficiency of production of the desired daughter plasmid was about 60 fold higher using both enzymes than using Cre alone. Nineteen of twenty four colonies from the Cre-only reaction contained the desired product, while thirty eight of thirty eight colonies from the integrase plus Cre reaction contained the desired product plasmid.

Other Selection Schemes A variety of selection schemes can be used that are known in the art as they can suit a particular purpose for which the recombinational cloning is carried out. Depending upon individual preferences and needs, a number of different types of selection schemes can be used in the recombinational cloning method of the present invention. The skilled artisan can take advantage of the availability of the many DNA segments or methods for making them and the different methods of selection that are routinely used in the art. Such DNA segments include but are not limited to those which encodes an activity such as, but not limited to, production of RNA, peptide, or protein, or providing a binding site for such RNA, peptide, or protein. Examples of DNA molecules used in devising a selection scheme are given above, under the definition of "selection scheme".

Additional examples include but are not limited to:

(i) Generation of new primer sites for PCR (e.g., juxtaposition of two DNA sequences that were not previously juxtaposed);

(ii) Inclusion of a DNA sequence acted upon by a restriction endonuclease or other DNA modifying enzyme, chemical, ribozyme, etc.;

(iii) Inclusion of a DNA sequence recognized by a DNA binding protein, RNA, DNA, chemical, etc.) (e.g., for use as an affinity tag for selecting for or excluding from a population) (Davis, *Nucl. Acids Res.* 24:702-706 (1996); *J. Virol.* 69: 8027-8034 (1995));

(iv) In vitro selection of RNA ligands for the ribosomal L22 protein associated with Epstein-Barr virus-expressed RNA by using randomized and cDNA-derived RNA libraries;

(vi) The positioning of functional elements whose activity requires a specific orientation or juxtaposition (e.g., (a) a recombination site which reacts poorly in tans, but when placed in cis, in the presence of the appropriate proteins, results in recombination that destroys certain populations of molecules; (e.g., reconstitution of a promoter sequence that allows in vitro RNA synthesis). The RNA can be used directly, or can be reverse transcribed to obtain the desired DNA construct;

(vii) Selection of the desired product by size (e.g., fractionation) or other physical property of the molecule(s); and (viii) Inclusion of a DNA sequence required for a specific modification (e.g., methylation) that allows its identification.

After formation of the Product and Byproduct in the method of the present invention, the selection step can be carried out either in vitro or in vivo depending upon the particular selection scheme which has been optionally devised in the particular recombinational cloning procedure.

For example, an in vitro method of selection can be devised for the Insert Donor and Vector Donor DNA molecules. Such scheme can involve engineering a rare restriction site in the starting circular vectors in such a way that after the recombination events the rare cutting sites end up in the Byproduct. Hence, when the restriction enzyme which binds and cuts at the rare restriction site is added to the reaction mixture in vitro, all of the DNA molecules carrying the rare cutting site, i.e., the starting DNA molecules, the Cointegrate, and the Byproduct, will be cut and rendered nonreplicable in the intended host cell. For example, cutting sites in segments B and C (see FIG. 1) can be used to select against all molecules except the Product. Alternatively, only a cutting site in C is needed if one is able to select for segment D, e.g., by a drug resistance gene not found on B.

Similarly, an in vitro selection method can be devised when dealing with linear DNA molecules. DNA sequences complementary to a PCR primer sequence can be so engineered that they are transferred, through the recombinational cloning method, only to the Product molecule. After the reactions are completed, the appropriate primers are added to the reaction solution and the sample is subjected to PCR. Hence, all or part of the Product molecule is amplified.

Other in vivo selection schemes can be used with a variety of E. coli cell lines. One is to put a repressor gene on one segment of the subcloning plasmid, and a drug marker controlled by that repressor on the other segment of the same plasmid. Another is to put a killer gene on segment C of the subcloning plasmid (FIG. 1). Of course a way must exist for growing such a plasmid, i.e., there must exist circumstances under which the killer gene will not kill. There are a number of these genes known which require particular strains of E. coli. One such scheme is to use the restriction enzyme DpnI, which will not cleave unless its recognition sequence GATC is methylated. Many popular common E. coli strains methylate GATC sequences, but there are mutants in which cloned DpnI can be expressed without harm.

Of course analogous selection schemes can be devised for other host organisms. For example, the tet repressor/operator of Tn10 has been adapted to control gene expression in eukaryotes (Gossen, M., and Bujard, H., *Proc. Natl. Acad Sci. USA* 89:5547-5551 (1992)). Thus the same control of drug resistance by the tet repressor exemplified herein can be applied to select for Product in eukaryotic cells.

Recombination Proteins

In the present invention, the exchange of DNA segments is achieved by the use of recombination proteins, including recombinases and associated co-factors and proteins. Various recombination proteins are described in the art. Examples of such recombinases include:

Cre: A protein from bacteriophage P1 (Abremski and Hoess, *J. Biol. Chem.* 259(3):1509-1514 (1984)) catalyzes the exchange (ie., causes recombination) between 34 bp DNA sequences called loxP (locus of crossover) sites (See Hoess et al., *Nucl. Acids Res.* 14(5)-2287 (1986)). Cre is available commercially (Novagen, Catalog No. 69247-1). Recombination mediated by Cre is freely reversible. From thermodynamic considerations it is not surprising that Cre-mediated integration (recombination between two molecules to form one molecule) is much less efficient than Cre-mediated excision (recombination between two loxP sites in the same molecule to form two daughter molecules). Cre works in simple buffers with either magnesium or spermidine as a cofactor, as is well known in the art The DNA substrates can be either linear or supercoiled. A number of mutant loxp sites have been described (Hoess et al., supra). One of these, loxP 511, recombines with another loxP 511 site, but will not recombine with a loxP site.

Integrase: A protein from bacteriophage lambda that mediates the integration of the lambda genome into the E. coli chromosome. The bacteriophage λ Int recombinational proteins promote irreversible recombination between its substrate att sites as part of the formation or induction of a lysogenic state. Reversibility of the recombination reactions results from two independent pathways for integrative and excisive recombination. Each pathway uses a unique, but overlapping, set of the 15 protein binding sites that comprise att site DNAs. Cooperative and competitive interactions involving four proteins (Int, Xis, IHF and FIS) determine the direction of recombination.

Integrative recombination involves the Int and IHF proteins and sites attP (240 bp) and aftB (25 bp). Recombination results in the formation of two new sites: attL and attR. Excisive recombination requires Int, IHF , and Xis, and sites attL and attR to generate attP and attB. Under certain conditions, FIS stimulates excisive recombination. In addition to these normal reactions, it should be appreciated that attP and attB, when placed on the same molecule, can promote excisive recombination to generate two excision products, one with attL and one with attR. Similarly, intermolecular recombination between molecules containing attL and attR, in the presence of Int, IHF and Xis, can result in integrative recombination and the generation attP and attB. Hence, by flanking DNA segments with appropriate combinations of engineered att sites, in the presence of the appropriate recombination proteins, one can direct excisive or integrative recombination, as reverse reactions of each other.

Each of the att sites contains a 15 bp core sequence; individual sequence elements of functional significance lie within, outside, and across the boundaries of this common core (Landy, A., *Ann. Rev. Biochem.* 58:913 (1989)). Efficient recombination between the various att sites requires that the sequence of the central common region be identical between the recombining partners, however, the exact sequence is now found to be modifiable. Consequently, derivatives of the att site with changes within the core are now discovered to recombine as least as efficiently as the native core sequences.

Integrase acts to recombine the attP site on bacteriophage lambda (about 240 bp) with the attB site on the E. coli genome (about 25 bp) (Weisberg, R. A. and Landy, A. in *Lambda II*, p. 211 (1983), Cold Spring Harbor Laboratory)), to produce the integrated lambda genome flanked by attL (about 100 bp) and attR (about 160 bp) sites. In the absence of Xis (see below), this reaction is essentially irreversible. The integration reaction mediated by integrase and IHF works in vitro, with simple buffer containing spermidine. Integrase can be obtained as described by Nash, H. A., *Methods of Enzymology* 100:210-216 (1983). IHF can be obtained as described by Filutowicz, M., et al., *Gene* 147: 149-150 (1994).

In the presence of the λ protein Xis (excise) integrase catalyzes the reaction of attR and attL to form attP and attB, i.e., it promotes the reverse of the reaction described above. This reaction can also be applied in the present invention.

Other Recombination Systems. Numerous recombination systems from various organisms can also be used, based on the teaching and guidance provided herein. See, e.g., Hoess et al., *Nucleic Acids Research* 14(6):2287 (1986); Abremski et al., *J. Biol. Chem.* 261(1):391 (1986); Campbell, *J. Bacteriol.* 174(23):7495 (1992); Qian et al., *J. Biol. Chem.* 267(11):7794 (1992); Araki et al., *J. Mol. Biol.* 225(1):25 (1992)). Many of these belong to the integrase family of recombinases (Argos et al. *EMBO J.* 5:433-440 (1986)). Perhaps the best studied of these are the Integrase/att system from bacteriophage λ (Landy, A. (1993) *Current Opinions in Genetics and Devel.* 3:699-707), the Cre/loxP system from bacteriophage P1 (Hoess and Abremski (1990) In *Nucleic Acids and Molecular Biology*, vol. 4. Eds.: Eckstein and Lilley, Berlin-Heidelberg: Springer-Verlag; pp. 90-109), and the FLP/FRT system from the *Saccharomyces cerevisiae* 2μ circle plasmid (Broach et al. *Cell* 29:227-234 (1982)).

Members of a second family of site-specific recombinases, the resolvase family (e.g., γδ, Tn3 resolvase, Hin, Gin, and Cin) are also known Members of this highly related family of recombinases are typically constrained to intramolecular reactions (e.g., inversions and excisions) and can require host-encoded factors. Mutants have been isolated that relieve some of the requirements for host factors (Maeser and Kahnmann (1991) *Mol. Gen. Genet.* 230:170-176), as well as some of the constraints of intramolecular recombination.

Other site-specific recombinases similar to λ Int and similar to P1 Cre can be substituted for Int and Cre. Such recombinases are known. In many cases the purification of such other recombinases has been described in the art. In cases when they are not known, cell extracts can be used or the enzymes can be partially purified using procedures described for Cre and Int.

While Cre and Int are described in detail for reasons of example, many related recombinase systems exist and their application to the described invention is also provided according to the present invention. The integrase family of site-specific recombinases can be used to provide alternative recombination proteins and recombination sites for the present invention, as site-specific recombination proteins encoded by bacteriophage lambda, phi 80, P22, P2, 186, P4 and P1. This group of proteins exhibits an unexpectedly large diversity of sequences. Despite this diversity, all of the recombinases can be aligned in their C-terminal halves.

A 40-residue region near the C terminus is particularly well conserved in all the proteins and is homologous to a region near the C terminus of the yeast 2 mu plasmid Flp protein. Three positions are perfectly conserved within this family: histidine, arginine and tyrosine are found at respective alignment positions 396, 399 and 433 within the well-conserved C-terminal region. These residues contribute to the active site of this family of recombinases, and suggest that tyrosine-433 forms a transient covalent linkage to DNA during strand cleavage and rejoining. See, e.g., Argos, P. et al., *EMBO J.* 5:433-40 (1986).

Alternatively, IS231 and other *Bacillus thuringiensis* transposable elements could be used as recombination proteins and recombination sites. *Bacillus thuringiensis* is an entomopathogenic bacterium whose toxicity is due to the presence in the sporangia of delta-endotoxin crystals active against agricultural pests and vectors of human and animal diseases. Most of the genes coding for these toxin proteins are plasmid-borne and are generally structurally associated with insertion sequences (IS231, IS232, IS240, ISBT1 and ISBT2) and transposons (Tn4430 and Tn5401). Several of these mobile elements have been shown to be active and participate in the crystal gene mobility, thereby contributing to the variation of bacterial toxicity.

Structural analysis of the iso-IS231 elements indicates that they are related to IS1151 from *Clostridium perfringens* and distantly related to IS4 and IS186 from *Escherichia coli*. Like the other IS4 family members, they contain a conserved transposase-integrase motif found in other IS families and retroviruses.

Moreover, functional data gathered from IS231A in *Escherichia coli* indicate a non-replicative mode of transposition; with a preference for specific targets. Similar results were also obtained in *Bacillus subtilis* and *B. thuringiensis*. See, e.g., Mahillon, J. et al., *Genetica* 93:13-26 (1994); Campbell, *J. Bacteriol.* 7495-7499 (1992).

The amount of recombinase which is added to drive the recombination reaction can be determined by using known assays. Specifically, titration assay is used to determine the appropriate amount of a purified recombinase enzyme, or the appropriate amount of an extract.

Engineered Recombination Sites. The above recombinases and corresponding recombinase sites are suitable for use in recombination cloning according to the present invention. However, wild-type recombination sites contain sequences that reduce the efficiency or specificity of recombination reactions as applied in methods of the present invention. For example, multiple stop codons in attB, attR, attP, attL and loxP recombination sites occur in multiple reading frames on both strands, so recombination efficiencies are reduced, e.g., where the coding sequence must cross the recombination sites, (only one reading frame is available on each strand of loxP and attB sites) or impossible (in attP, attR or attL).

Accordingly, the present invention also provides engineered recombination sites that overcome these problems. For example, att sites can be engineered to have one or multiple mutations to enhance specificity or efficiency of the recombination reaction and the properties of Product DNAs (e.g., att1, att2, and att3 sites); to decrease reverse reaction (e.g., removing P1 and H1 from attB). The testing of these mutants determines which mutants yield sufficient recombinational activity to be suitable for recombination subcloning according to the present invention.

Mutations can therefore be introduced into recombination sites for enhancing site specific recombination. Such mutations include, but are not limited to: recombination sites without translation stop codons that allow fusion proteins to be encoded; recombination sites recognized by the same proteins but differing in base sequence such that they react largely or exclusively with their homologous partners allow multiple reactions to be contemplated. Which particular reactions take place can be specified by which particular partners are present in the reaction mixture. For example, a tripartite protein fusion could be accomplished with parental plasmids containing recombination sites attR1 and attR2; attL1 and attL3; and/or attR3 and attL2.

There are well known procedures for introducing specific mutations into nucleic acid sequences. A number of these are described in Ausubel, F. M. et al., *Current Protocols in Molecular Biology*, Wiley Interscience, New York (1989-1996). Mutations can be designed into oligonucleotides, which can be used to modify existing cloned sequences, or in amplification reactions. Random mutagenesis can also be employed if appropriate selection methods are available to isolate the desired mutant DNA or RNA. The presence of the desired mutations can be confirmed by sequencing the nucleic acid by well known methods.

The following non-limiting methods can be used to engineer a core region of a given recombination site to provide mutated sites suitable for use in the present invention:
1. By recombination of two parental DNA sequences by site-specific (e.g. attL and attR to give attB) or other (e.g. homologous) recombination mechanisms. The DNA parental DNA segments containing one or more base alterations resulting in the final core sequence;
2. By mutation or mutagenesis (site-specific, PCR, random, spontaneous, etc) directly of the desired core sequence;
3. By mutagenesis (site-specific, PCR, random, spontanteous, etc) of parental DNA sequences, which are recombined to generate a desired core sequence; and
4. By reverse transcription of an RNA encoding the desired core sequence.

The functionality of the mutant recombination sites can be demonstrated in ways that depend on the particular characteristic that is desired. For example, the lack of translation stop codons in a recombination site can be demonstrated by expressing the appropriate fusion proteins. Specificity of recombination between homologous partners can be demonstrated by introducing the appropriate molecules into in vitro reactions, and assaying for recombination products as described herein or known in the art. Other desired mutations in recombination sites might include the presence or absence of restriction sites, translation or transcription start signals, protein binding sites, and other known functionalities of nucleic acid base sequences. Genetic selection schemes for particular functional attributes in the recombination sites can be used according to known method steps. For example, the modification of sites to provide (from a pair of sites that do not interact) partners that do interact could be achieved by requiring deletion, via recombination between the sites, of a DNA sequence encoding a toxic substance. Similarly, selection for sites that remove translation stop sequences, the presence or absence of protein binding sites, etc., can be easily devised by those skilled in the art.

Accordingly, the present invention provides a nucleic acid molecule, comprising at least one DNA segment having at least two engineered recombination sites flanking a Selectable marker and/or a desired DNA segment, wherein at least one of said recombination sites comprises a core region having at least one engineered mutation that enhances recombination in vitro in the formation of a Cointegrate DNA or a Product DNA.

The nucleic acid molecule can have at least one mutation that confers at least one enhancement of said recombination, said enhancement selected from the group consisting of substantially (i) favoring excisive integration; (ii) favoring excisive recombination; (ii) relieving the requirement for host factors; (iii) increasing the efficiency of said Cointegrate DNA or Product DNA formation; and (iv) increasing the specificity of said Cointegrate DNA or Product DNA formation.

The nucleic acid molecule preferably comprises at least one recombination site derived from attB, attP, attL or attR. More preferably the att site is selected from att1, att2, or att3, as described herein.

In a preferred embodiment, the core region comprises a DNA sequence selected from the group consisting of:

```
(a)
RKYCWGCTTTYKTRTACNAASTSGB  (m-att)      (SEQ ID NO:1);

(b)
AGCCWGCTTTYKTRTACNAACTSGB  (m-attB)     (SEQ ID NO:2);

(c)
GTTCAGCTTTCKTRTACNAACTSGB  (m-attR)     (SEQ ID NO:3);

(d)
AGCCWGCTTTCKTRTACNAAGTSGB  (m-attL)     (SEQ ID NO:4);

(e)
GTTCAGCTTTYKTRTACNAAGTSGB  (m-attP1)    (SEQ ID NO:5);
``` or a corresponding or complementary DNA or RNA sequence, wherein R=A or G; K=G or T/U; Y=C or T/U; W=A or T/U; N=A or C or G or T/U; S=C or G; and B=C or G or T/U, as presented in 37 C.F.R §1.822, which is entirely incorporated herein by reference, wherein the core region does not contain a stop codon in one or more reading frames.

The core region also preferably comprises a DNA sequence selected from the group consisting of:

```
(a)   AGCCTGCTTTTTTGTACAAACTTGT  (attB1)     (SEQ ID NO:6);

(b)   AGCCTGCTTTCTTGTACAAACTTGT  (attB2)     (SEQ ID NO:7);

(c)   ACCCAGCTTTCTTGTACAAACTTGT  (attB3)     (SEQ ID NO:8);

(d)   GTTCAGCTTTTTTGTACAAACTTGT  (attR1)     (SEQ ID NO:9);

(e)   GTTCAGCTTTCTTGTACAAACTTGT  (attR2)     (SEQ ID NO:10);

(f)   GTTCAGCTTTCTTGTACAAAGTTGG  (attR3)     (SEQ ID NO:11);

(g)   AGCCTGCTTTTTTGTACAAAGTTGG  (attL1)     (SEQ ID NO:12);

(h)   AGCCTGCTTTCTTGTACAAAGTTGG  (attL2)     (SEQ ID NO:13);

(i)   ACCCAGCTTTCTTGTACAAAGTTGG  (attL3)     (SEQ ID NO:14);

(j)   GTTCAGCTTTTTTGTACAAAGTTGG  (attP1)     (SEQ ID NO:15);

(k)   GTTCAGCTTTCTTGTACAAAGTTGG  (attP2, P3) (SEQ ID NO:16);
``` or a corresponding or complementary DNA or RNA sequence.

The present invention thus also provides a method for making a nucleic acid molecule, comprising providing a nucleic acid molecule having at least one engineered recombination site comprising at least one DNA sequence having at least 80-99% homology (or any range or value therein) to at least one of SEQ ID NOS:1-16, or any suitable recombination site, or which hybridizes under stringent conditions thereto, as known in the art.

Clearly, there are various types and permutations of such well-known in vitro and in vivo selection methods, each of which are not described herein for the sake of brevity. However, such variations and permutations are contemplated and considered to be the different embodiments of the present invention.

It is important to note that as a result of the preferred embodiment being in vitro recombination reactions, non-biological molecules such as PCR products can be manipulated via the present recombinational cloning method. In one example, it is possible to clone linear molecules into circular vectors.

There are a number of applications for the present invention. These uses include, but are not limited to, changing vectors, apposing promoters with genes, constructing genes for fusion proteins, changing copy number, changing replicons, cloning into phages, and cloning, e.g., PCR products (with an attB site at one end and a loxP site at the other end), genomic DNAs, and cDNAs.

The following examples are intended to further illustrate certain preferred embodiments of the invention and are not intended to be limiting in nature.

EXAMPLES

The present recombinational cloning method accomplishes the exchange of nucleic acid segments to render something useful to the user, such as a change of cloning vectors. These segments must be flanked on both sides by recombination signals that are in the proper orientation with respect to one another. In the examples below the two parental nucleic acid molecules (e.g., plasmids) are called the Insert Donor and the Vector Donor. The Insert Donor contains a segment that will become joined to a new vector contributed by the Vector Donor. The recombination intermediate(s) that contain(s) both starting molecules is called the Cointegrate(s). The second recombination event produces two daughter molecules, called the Product (the desired new clone) and the Byproduct.

Buffers

Various known buffers can be used in the reactions of the present invention. For restriction enzymes, it is advisable to use the buffers recommended by the manufacturer. Alternative buffers can be readily found in the literature or can be devised by those of ordinary skill in the art.

Examples 1-3. One exemplary buffer for lambda integrase is comprised of 50 mM Tris-HCl, at pH 7.5-7.8, 70 mM KCl, 5 mM spermidine, 0.5 mM EDTA, and 0.25 mg/ml bovine serum albumin, and optionally, 10% glycerol.

One preferred buffer for P1 Cre recombinase is comprised of 50 mM Tris-HCl at pH 7.5, 33 mM NaCl, 5 mM spermidine, and 0.5 mg/ml bovine serum albumin.

The buffer for other site-specific recombinases which are similar to lambda Int and P1 Cre are either known in the art or can be determined empirically by the skilled artisans, particularly in light of the above-described buffers.

Example 1

Recombinational Cloning Using Cre and Cre & Int

Two pairs of plasmids were constructed to do the in vitro recombinational cloning method in two different ways. One pair, pEZC705 and pEZC726 (FIG. 2A), was constructed with loxP and att sites, to be used with Cre and λ integrase. The other pair, pEZC602 and pEZC629 (FIG. 3A), contained the loxP (wild type) site for Cre, and a second mutant lox site, loxP 511, which differs from loxP in one base (out of 34 total). The minimum requirement for recombinational cloning of the present invention is two recombination sites in each plasmid, in general X and Y, and X' and Y'. Recombinational cloning takes place if either or both types of site can recombine to form a Cointegrate (e.g. X is and X'), and if either or both (but necessarily a site different from the type forming the Cointegrate) can recombine to excise the Product and Byproduct plasmids from the Cointegrate (e.g. Y and Y'). It is important that the recombination sites on the same plasmid do not recombine. It was found that the present recombinational cloning could be done with Cre alone.

Cre-only

Two plasmids were constructed to demonstrate this conception (see FIG. 3A). pEZC629 was the Vector Donor plasmid. It contained a constitutive drug marker (chloramphenicol resistance), an origin of replication, loxP and loxP 511 sites, a conditional drug marker (kanamycin resistance whose expression is controlled by the operator/promoter of the tetracycline resistance operon of transposon Tn10), and a constitutively expressed gene for the tet repressor protein, tetR. E. coli cells containing pEZC629 were resistant to chloramphenicol at 30 µg/ml, but sensitive to kanamycin at 100 µg/ml. pEZC602 was the Insert Donor plasmid, which contained a different drug marker (ampicillin resistance), an origin, and loxP and loxP 511 sites flanking a multiple cloning site.

This experiment was comprised of two parts as follows:

Part I: About 75 ng each of pEZC602 and pEZC629 were mixed in a total volume of 30 µl of Cre buffer (50 mM Tris-HCl pH 7.5, 33 mM NaCl, 5 mM spermidine-HCl, 500 µg/ml bovine serum albumin). Two 10 µl aliquots were transferred to new tubes. One tube received 0.5 µl of Cre protein (approx. 4 units per µl; partially purified according to Abremski and Hoess, *J. Biol. Chem.* 259:1509(1984)). Both tubes were incubated at 37° C. for 30 minutes, then 70° C. for 10 minutes. Aliquots of each reaction were diluted and transformed into DH5α. Following expression, aliquots were plated on 30 µg/ml chloramphenicol; 100 µg/ml ampicillin plus 200 µg/ml methicillin; or 100 µg/ml kanamycin. Results: See Table 1. The reaction without Cre gave $1.11 \times 10^6$ ampicillin resistant colonies (from the Insert Donor plasmid pEZC602); $7.8 \times 10^5$ chloramphenicol resistant colonies (from the Vector Donor plasmid pEZC629); and 140 kanamycin resistant colonies (background). The reaction with added Cre gave $7.5 \times 10^5$ ampicillin resistant colonies (from the Insert Donor plasmid pEZC602); $6.1 \times 10^5$ chloramphenicol resistant colonies (from the Vector Donor plasmid pEZC629); and 760 kanamycin resistant colonies (mixture of background colonies and colonies from the recombinational cloning Product plasmid). Analysis: Because the number of colonies on the kanamycin plates was much higher in the presence of Cre, many or most of them were predicted to contain the desired Product plasmid.

TABLE 1

| Enzyme | Ampicillin | Chloramphenicol | Kanamycin | Efficiency |
|---|---|---|---|---|
| None | $1.1 \times 10^6$ | $7.8 \times 10^5$ | 140 | $140/7.8 \times 10^5 = 0.02\%$ |
| Cre | $7.5 \times 10^5$ | $6.1 \times 10^5$ | 760 | $760/6.1 \times 10^5 = 0.12\%$ |

Part II: Twenty four colonies from the "+Cre" kanamycin plates were picked and inoculated into medium containing 100 μg/ml kanamycin. Minipreps were done, and the miniprep DNAs, uncut or cut with SmaI or, HindIII, were electrophoresed. Results: 19 of the 24 minipreps showed supercoiled plasmid of the size predicted for the Product plasmid. All 19 showed the predicted SmaI and HindIII restriction fragments. Analysis: The Cre only scheme was demonstrated Specifically, it was determined to have yielded about 70% (19 of 24) Product clones. The efficiency was about 0.1% (760 kanamycin resistant clones resulted from $6.1 \times 10^5$ chloramphenicol resistant colonies).

Cre Plus Integrase

Figure 2A:
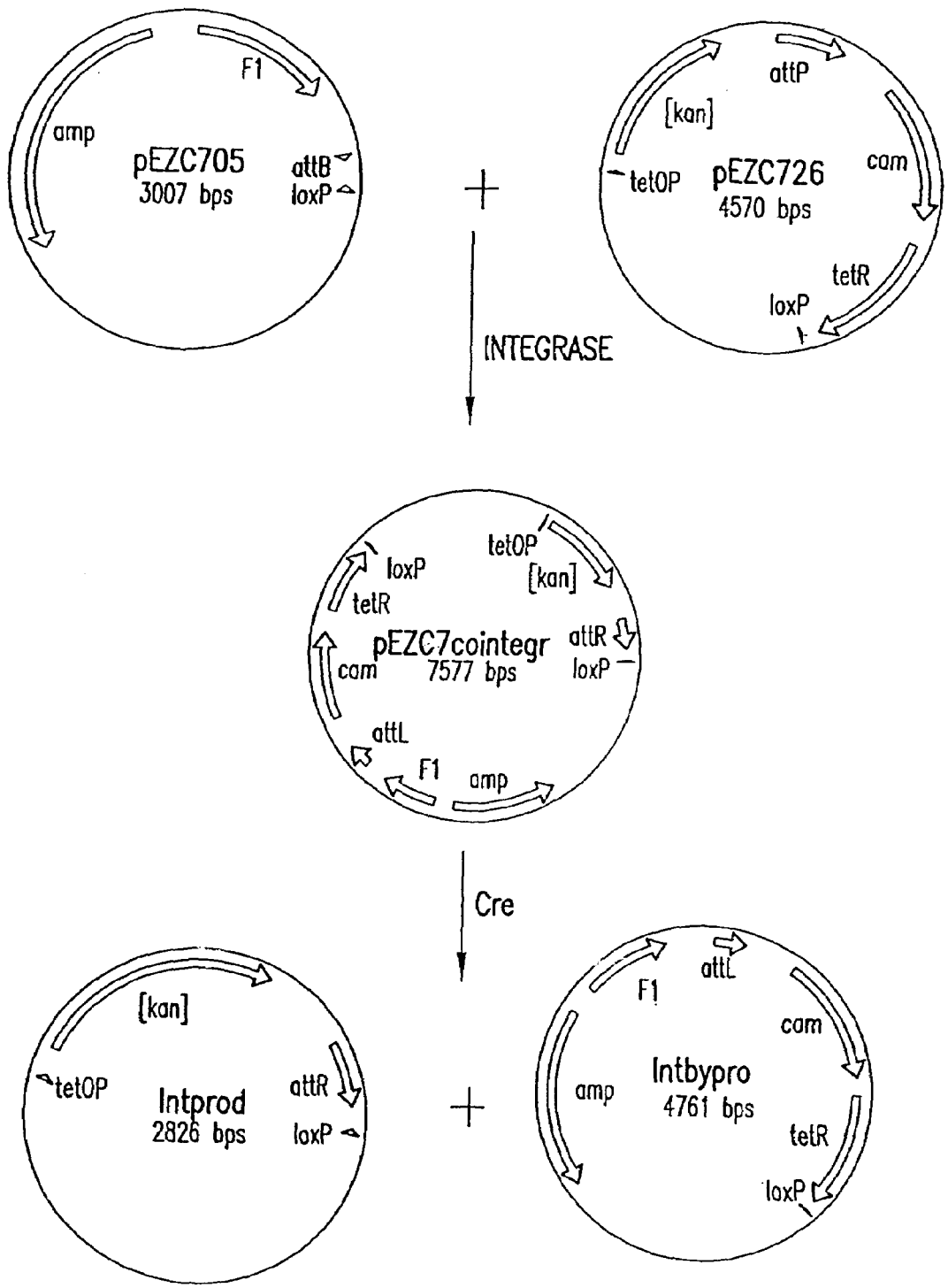
FIG. 2A depicts an in vitro method of recombining an Insert Donor plasmid (here, pEZC705) with a Vector Donor plasmid (here, pEZC726), and obtaining Product DNA and Byproduct daughter molecules. The two recombination sites are attP and loxP on the Vector Donor. On one segment defined by these sites is a kanamycin resistance gene whose promoter has been replaced by the tetOP operator/promoter from transposon Tn10. See Sizemore et al., Nucl. Acids Res. 18(10):2875 (1990). In the absence of tet repressor protein, E. coli RNA polymerase transcribes the kanamycin resistance gene from the tetOP. If tet repressor is present, it binds to tetOP and blocks transcription of the kanamycin resistance gene. The other segment of pEZC726 has the tet repressor gene expressed by a constitutive promoter. Thus cells transformed by pEZC726 are resistant to chloramphenicol, because of the chloramphenicol acetyl transferase gene on the same segment as tetR, but are sensitive to kanamycin. The recombinase-mediated reactions result in separation of the tetR gene from the regulated kanamycin resistance gene. This separation results in kanamycin resistance in cells receiving only the desired recombination products. The first recombination reaction is driven by the addition of the recombinase called Integrase. The second recombination reaction is driven by adding the recombinase Cre to the Cointegrate (here, pEZC7 Cointegrate).
Figure 2B:
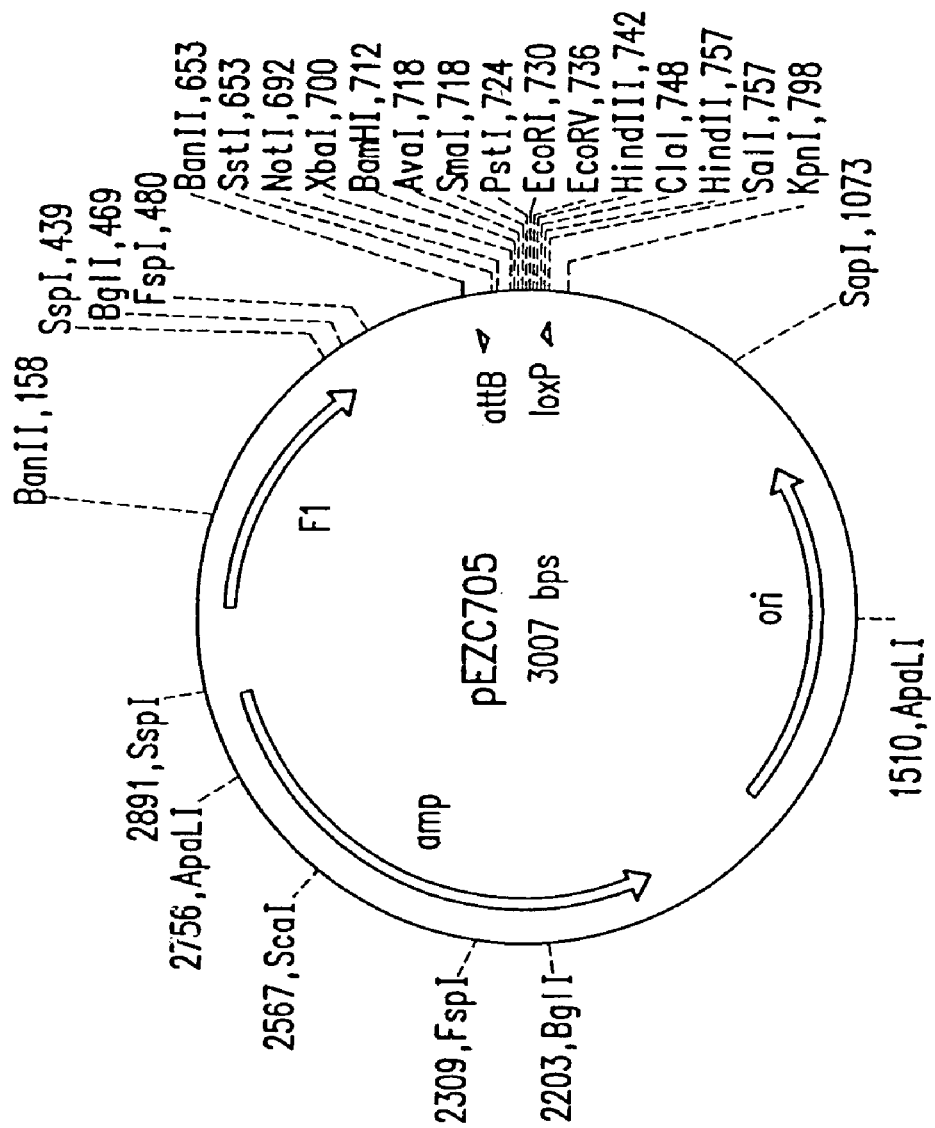
FIG. 2B depicts a restriction map of pEZC705.
Figure 2C:
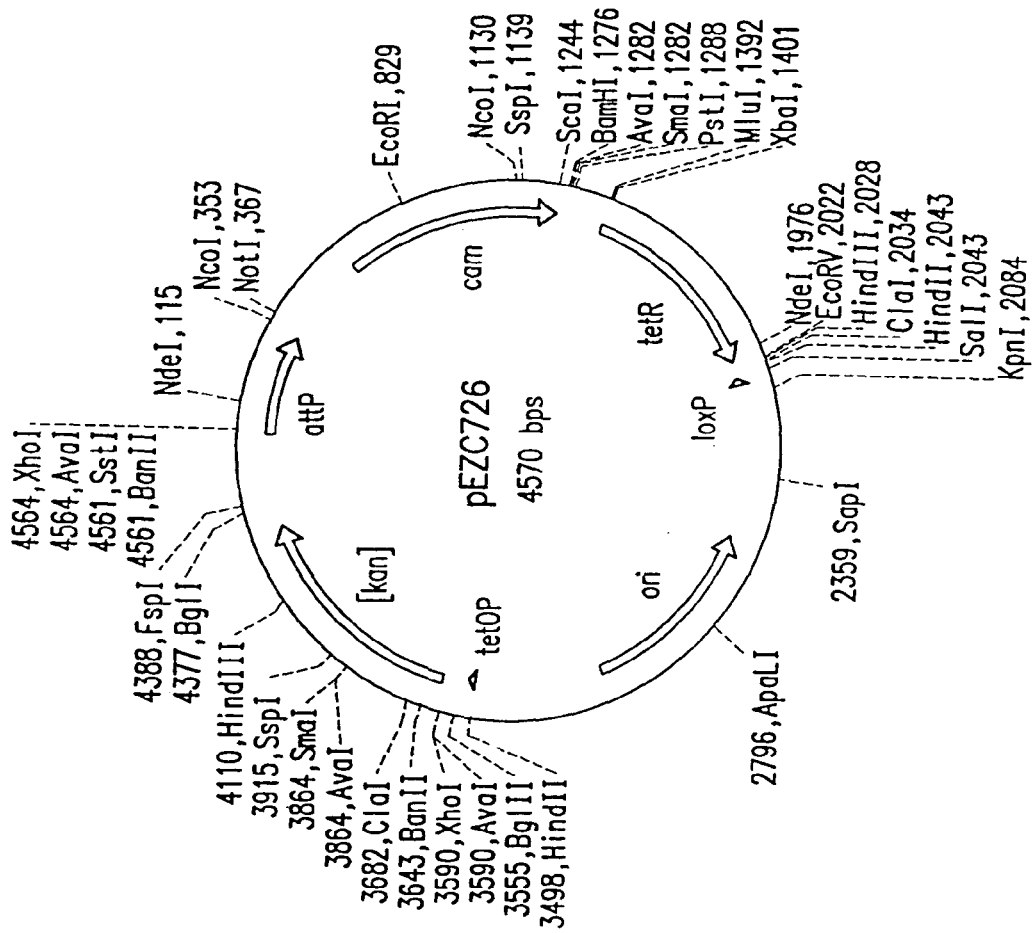
FIG. 2C depicts a restriction map of pEZC726.
Figure 2D:
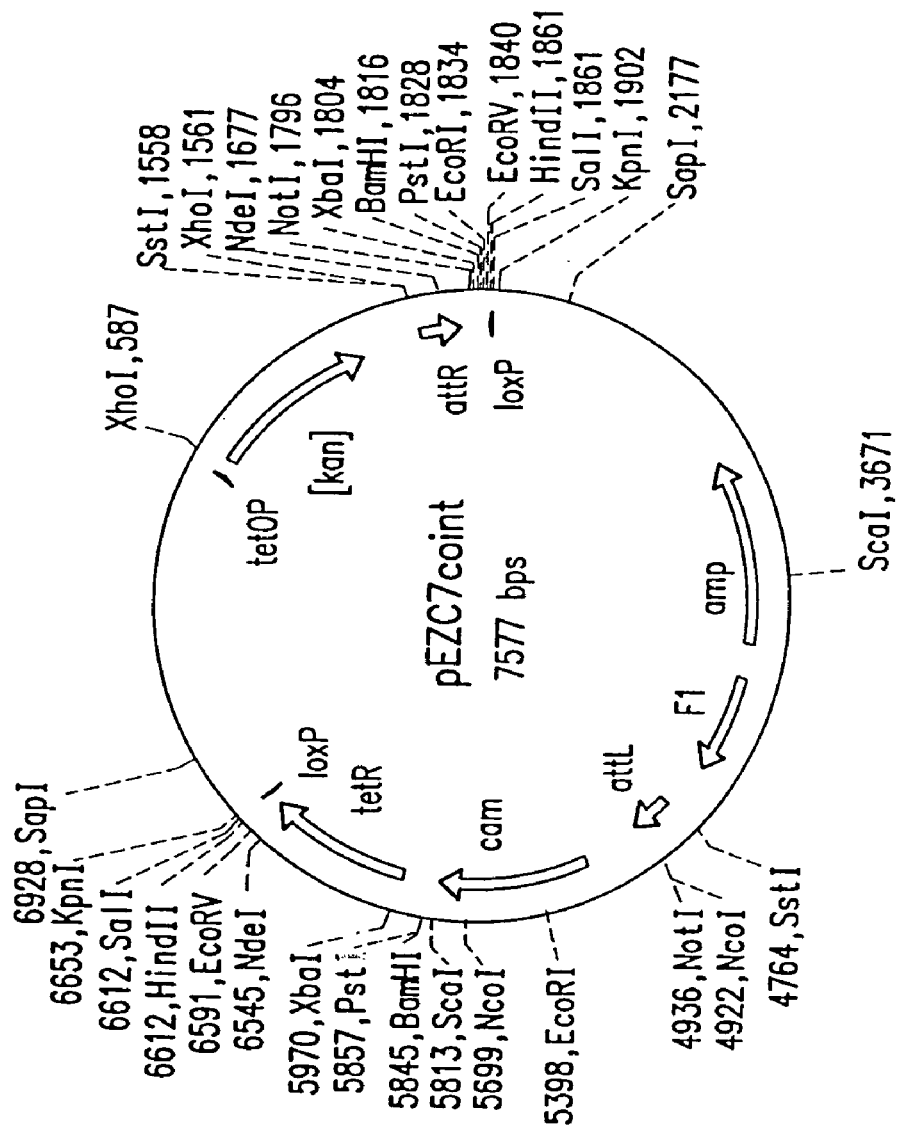
FIG. 2D depicts a restriction map of pEZC7 Cointegrate.
Figure 2E:
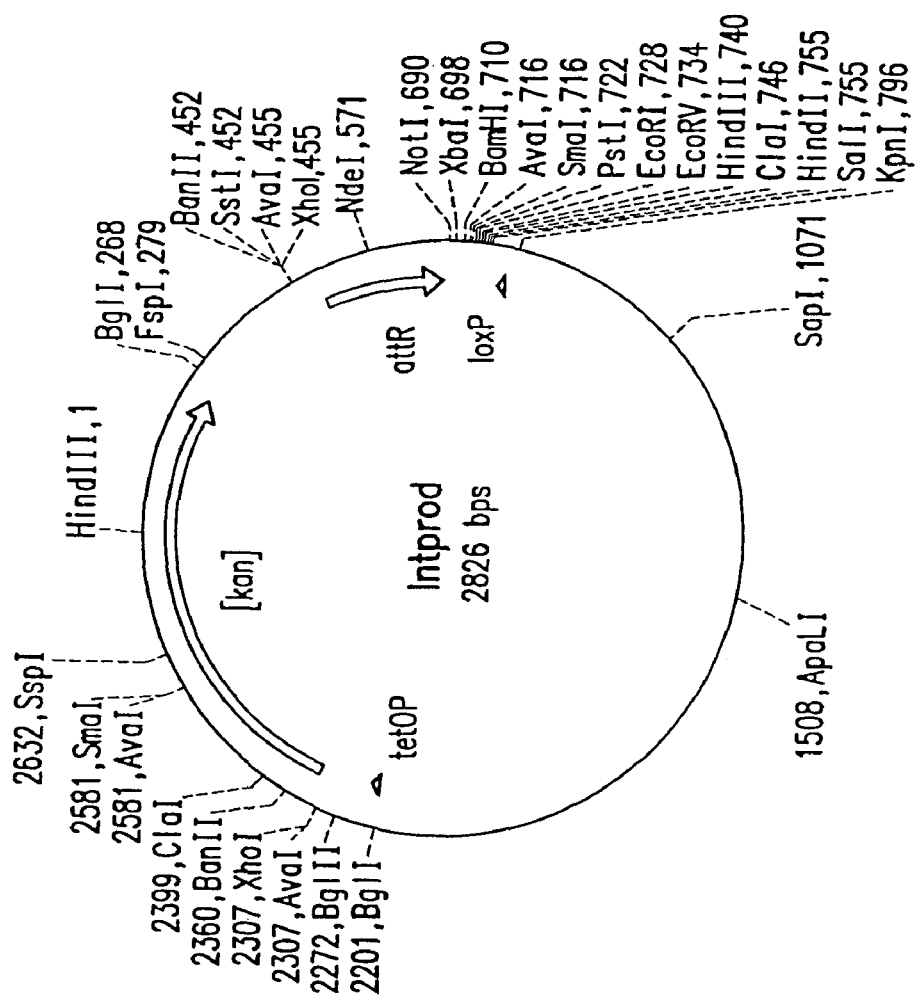
FIG. 2E depicts a restriction map of Intprod.
Figure 2F:
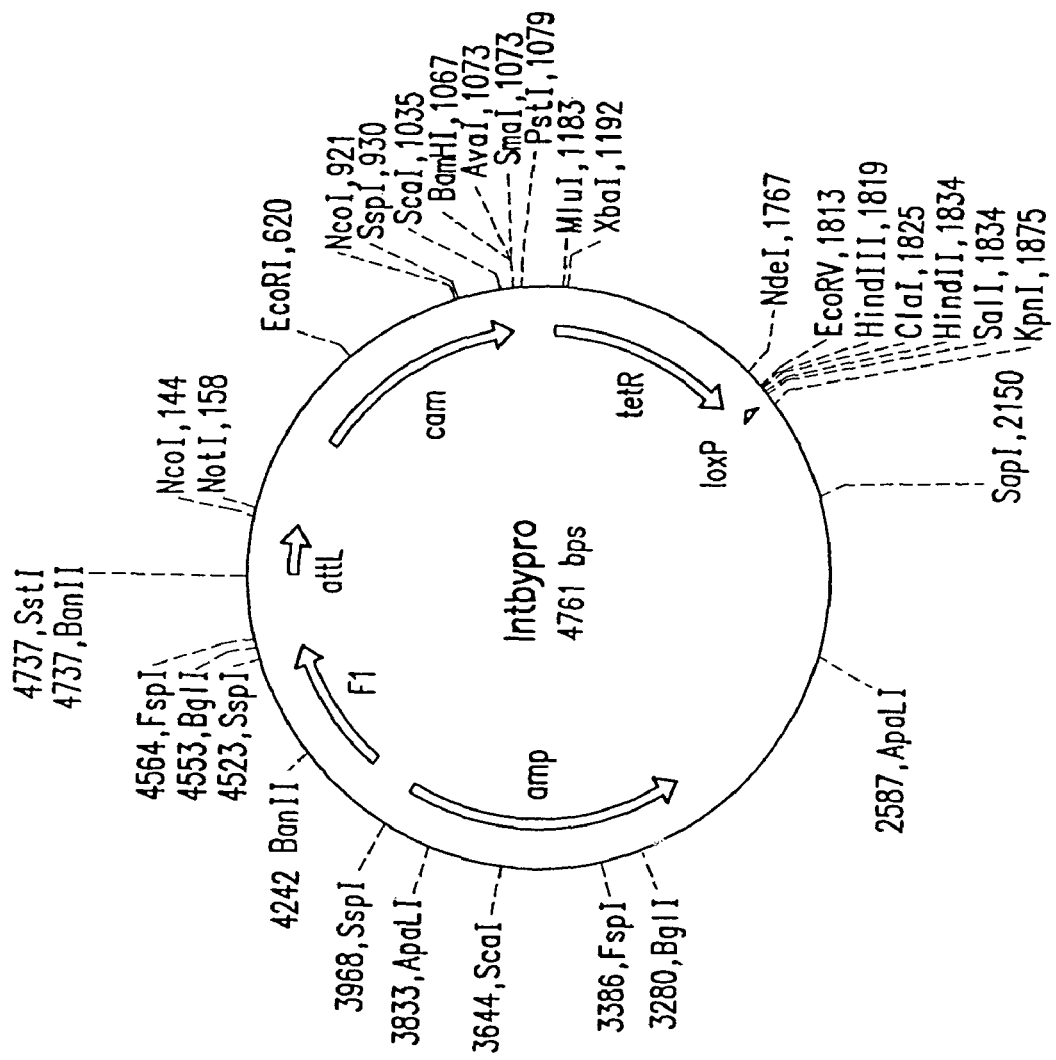
FIG. 2F depicts a restriction map of Intbypro.
Figure 3A:
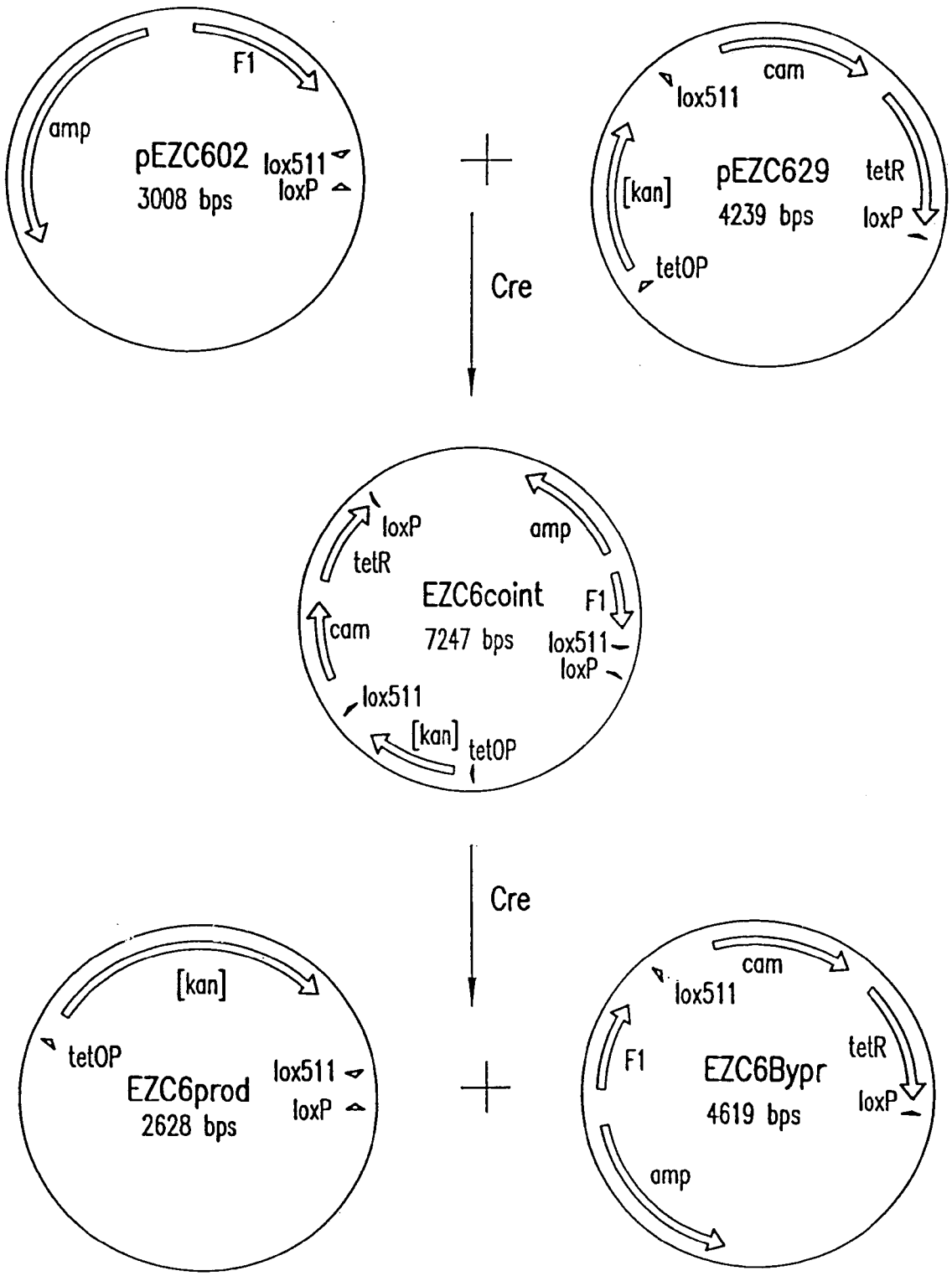
FIG. 3A depicts an in vitro method of recombining an Insert Donor plasmid (here, pEZC602) with a Vector Donor plasmid (here, pEZC629), and obtaining Product (here, EZC6prod) and Byproduct (here, EZC6Bypr) daughter molecules. The two recombination sites are loxP and loxP 511. One segment of pEZC629 defined by these sites is a kanamycin resistance gene whose promoter has been replaced by the tetOP operator/promoter from transposon Tn10. In the absence of tet repressor protein, E. coli RNA polymerase transcribes the kanamycin resistance gene from the tetOP. If tet repressor is present, it binds to tetOP and blocks transcription of the kanamycin resistance gene. The other segment of pEZC629 has the tet repressor gene expressed by a constitutive promoter. Thus cells transformed by pEZC629 are resistant to chloramphenicol, because of the chloramphenicol acetyl transferase gene on the same segment as tetR, but are sensitive to kanamycin. The reactions result in separation of the tetR gene from the regulated kanamycin resistance gene. This separation results in kanamycin resistance in cells receiving the desired recombination product. The first and the second recombination events are driven by the addition of the same recombinase, Cre.
Figure 3B:
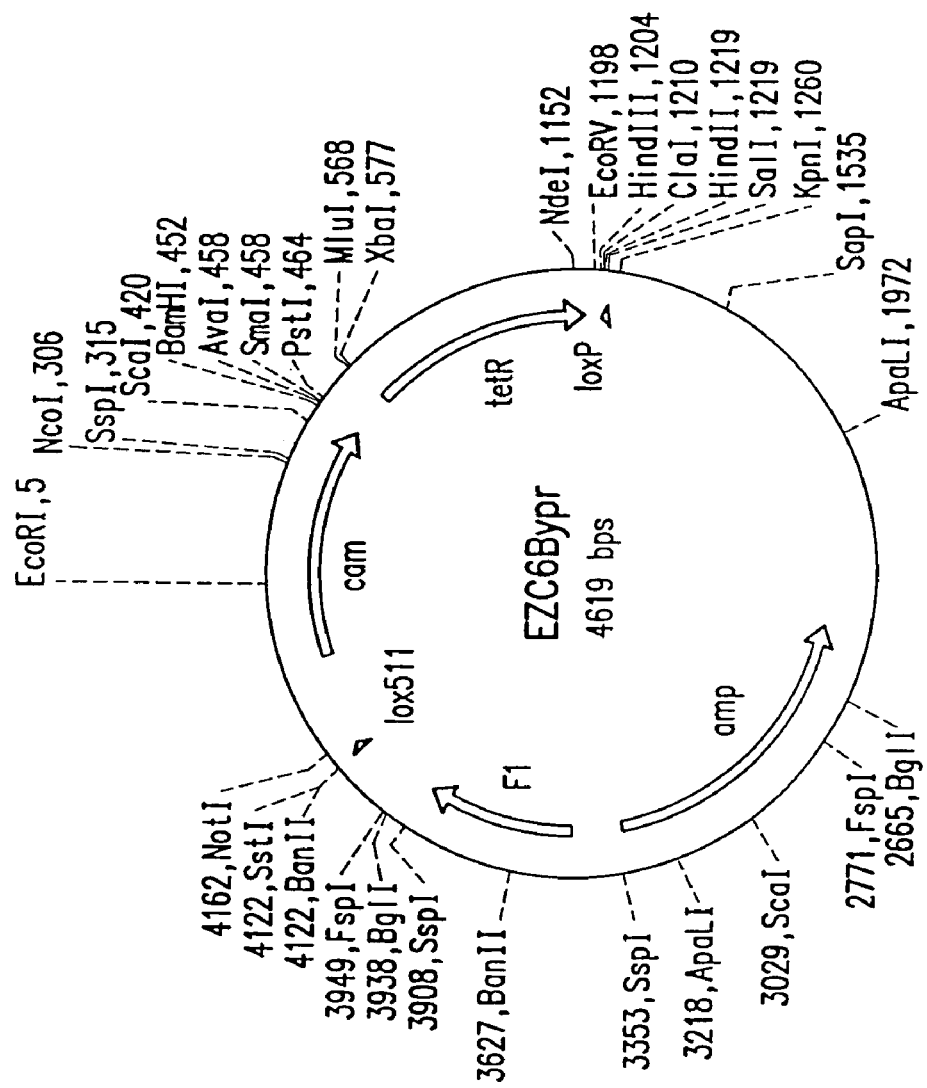
FIG. 3B depicts a restriction map of EZC6Bypr.
Figure 3C:
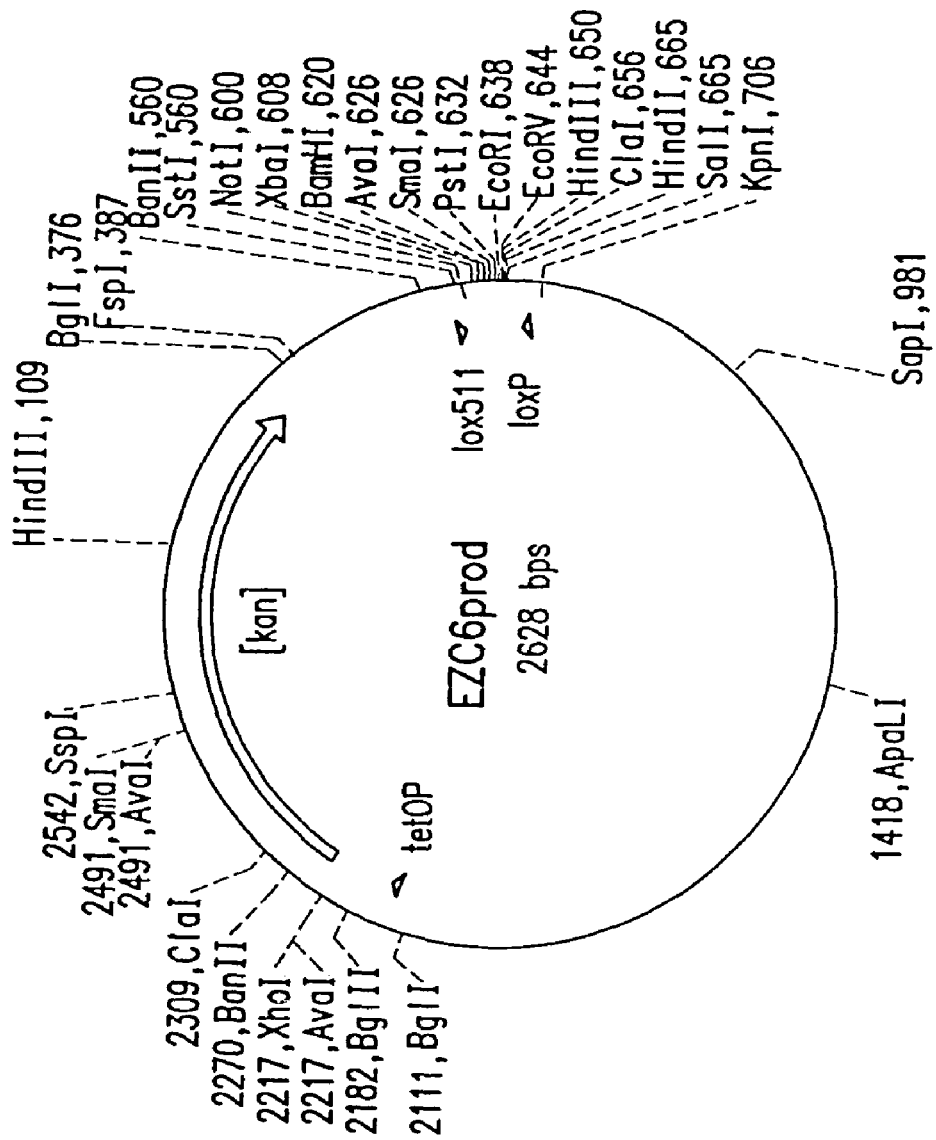
FIG. 3C depicts a restriction map of EZC6prod.
Figure 3D:
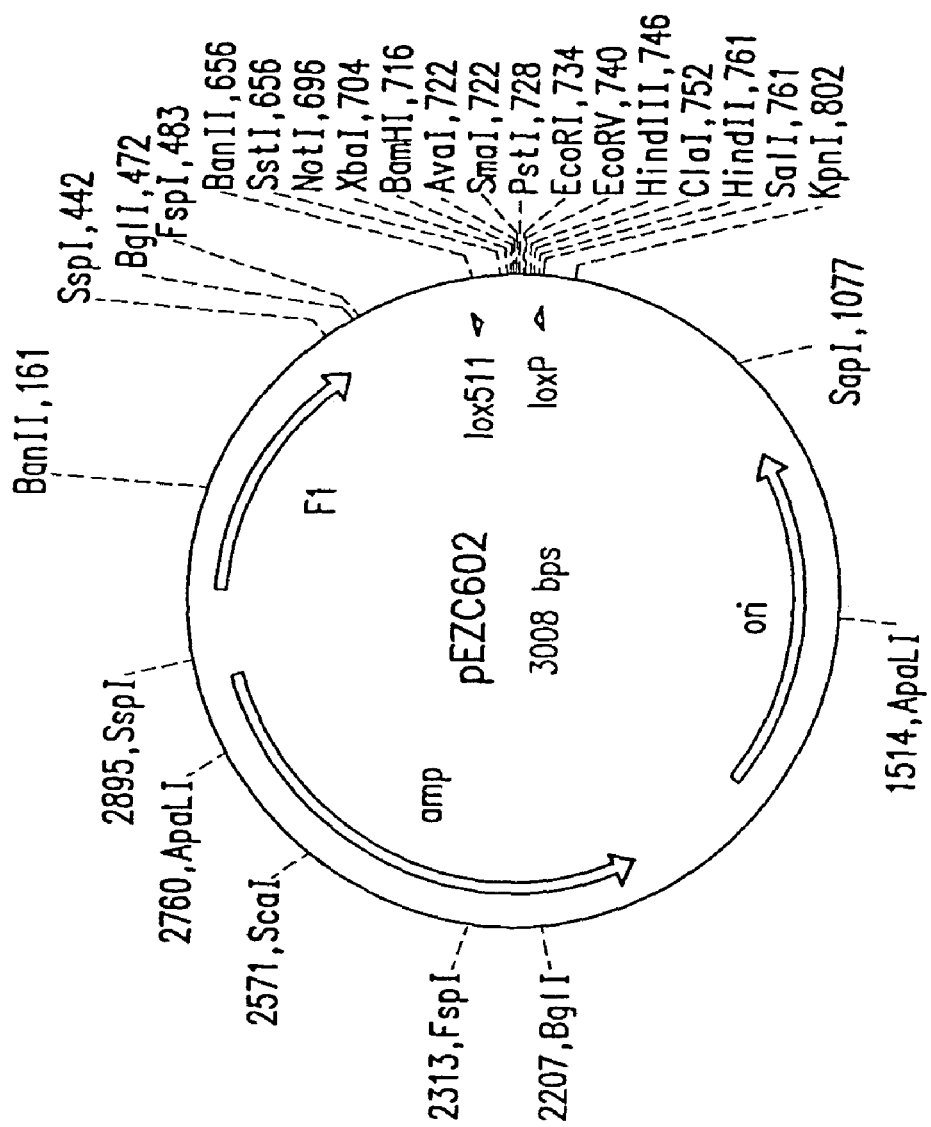
FIG. 3D depicts a restriction map of pEZC602.
Figure 3E:
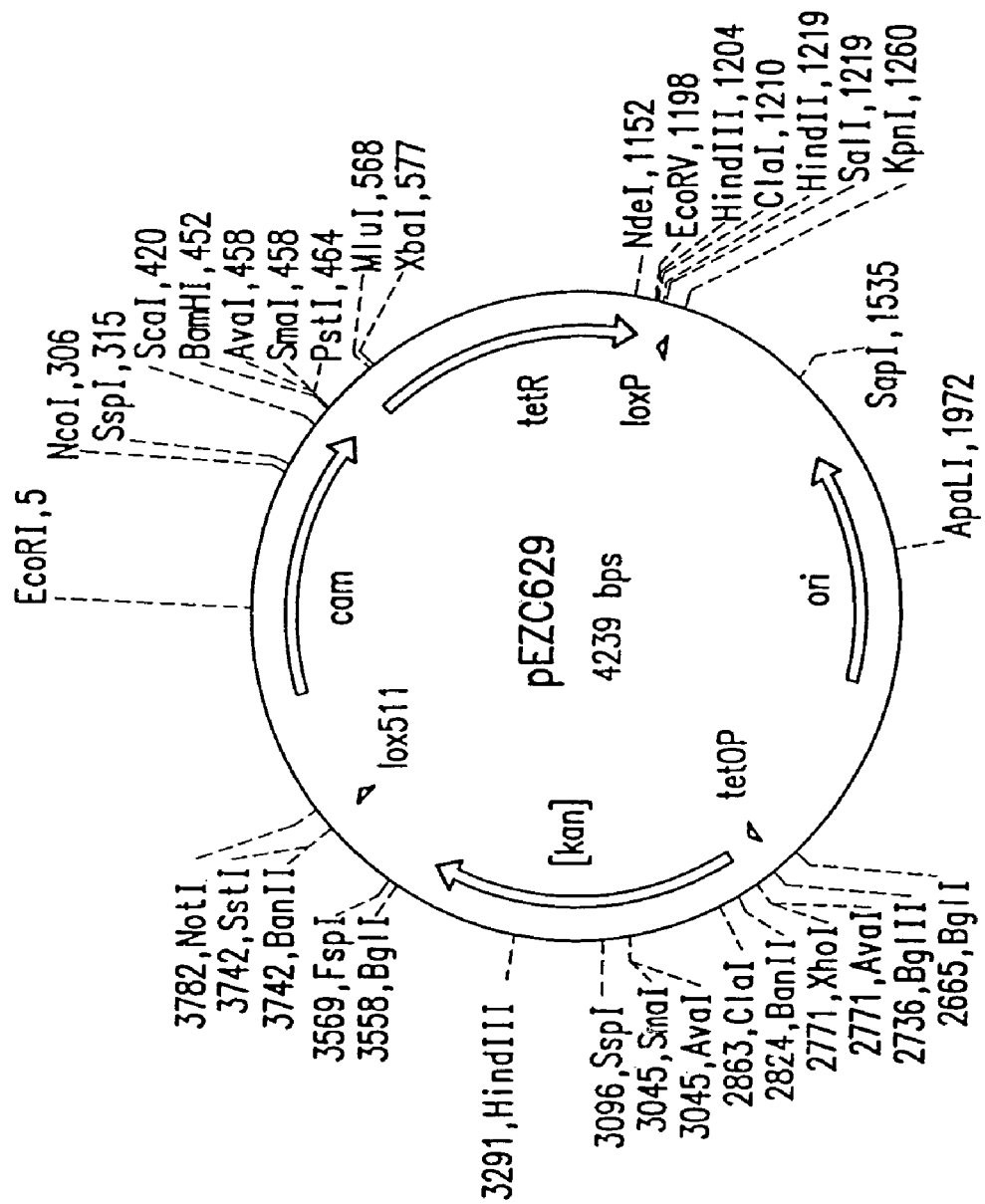
FIG. 3E depicts a restriction map of pEZC629.
Figure 3F:
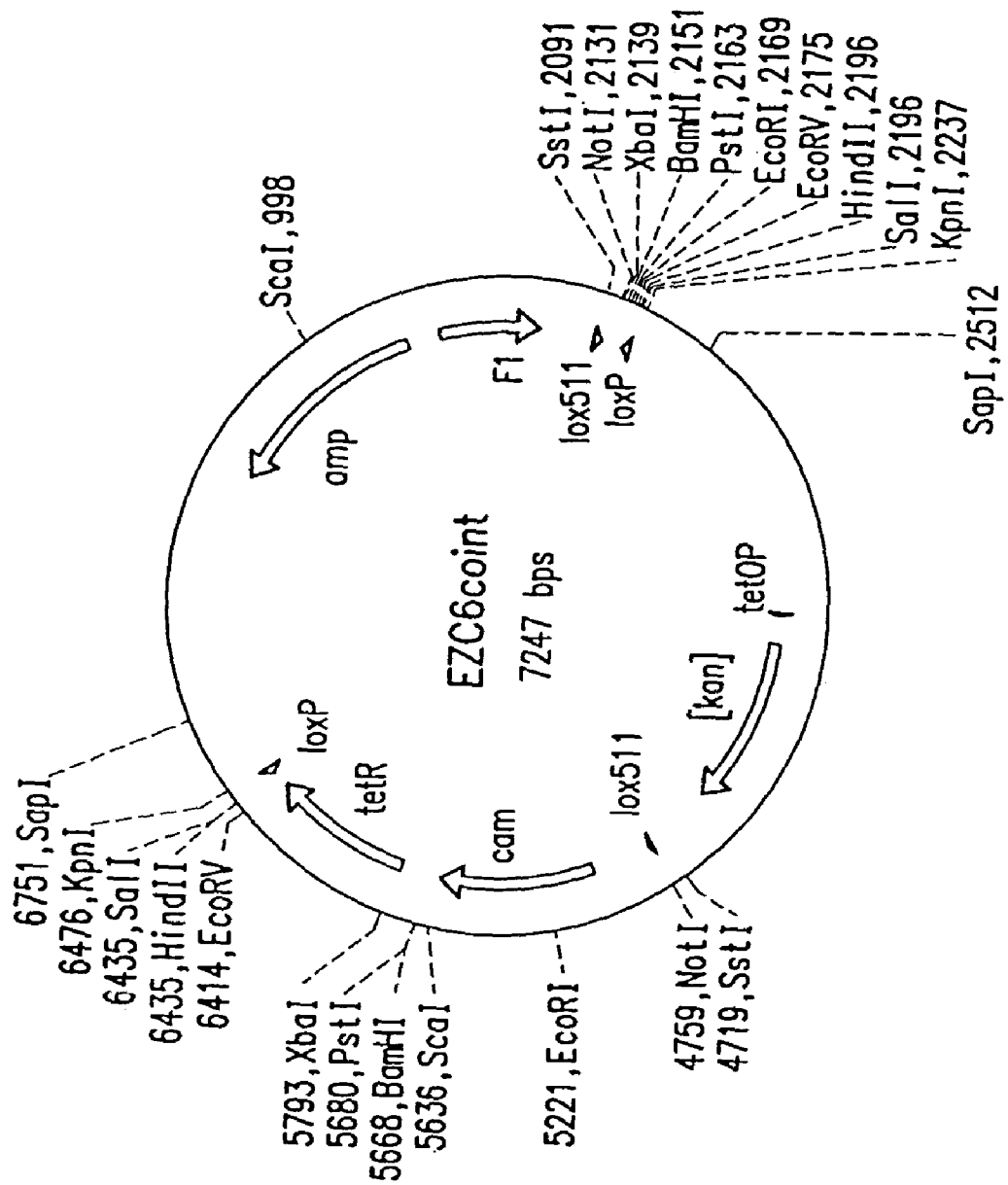
FIG. 3F depicts a restriction map of EZC6coint.

The plasmids used to demonstrate this method are exactly analogous to those used above, except that pEZC726, the Vector Donor plasmid, contained an attP site in place of loxP 511, and pEZC705, the Insert Donor plasmid, contained an attB site in place of loxP 511 (FIG. 2A).

This experiment was comprised of three parts as follows:

Part I: About 500 ng of pEZC705 (the Insert Donor plasmid) was cut with ScaI, which linearized the plasmid within the ampicillin resistance gene. (This was done because the λ integrase reaction has been historically done with the attB plasmid in a linear state (H. Nash, personal communication). However, it was found later that the integrase reaction proceeds well with both plasmids supercoiled.) Then, the linear plasmid was ethanol precipitated and dissolved in 20 μl of λ integrase buffer (50 mM Tris-HCl, about pH 7.8, 70 mM KCl, 5 mM spermidine-HCl, 0.5 mM EDTA, 250 μg/ml bovine serum albumin). Also, about 500 ng of the Vector Donor plasmid pEZC726 was ethanol precipitated and dissolved in 20 μl λ integrase buffer. Just before use, λ integrase (2 μl, 393 μg/ml) was thawed and diluted by adding 18 μl cold λ integrase buffer. One μl IHF (integration host factor, 2.4 mg/ml, an accessory protein) was diluted into 150 μl cold λ integrase buffer. Aliquots (2 μl) of each DNA were mixed with λ integrase buffer, with or without 1 μl each λ integrase and IHF, in a total of 10 μl. The mixture was incubated at 25° C. for 45 minutes, then at 70° C. for 10 minutes. Half of each reaction was applied to an agarose gel. Results: In the presence of integrase and IHF, about 5% of the total DNA was converted to a linear Cointegrate form Analysis: Activity of integrase and IHF was confirmed.

Part II: Three microliters of each reaction (i.e., with or without integrase and IHF) were diluted into 27 μl of Cre buffer (above), then each reaction was split into two 10 μl aliquots (four altogether). To two of these reactions, 0.5 μl of Cre protein (above) were added, and all reactions were incubated at 37° C. for 30 minutes, then at 70° C. for 10 minutes. TE buffer (90 μl; TE: 10 mM Tris-HCl, pH 7.5, 1 mM EDTA) was added to each reaction, and 1 μl each was transformed into E. coli DH5α. The transformation mixtures were plated on 100 μg/ml ampicillin plus 200 μg/ml methicillin; 30 μg/ml chloramphenicol; or 100 μg/ml kanamycin. Results: See Table 2.

TABLE 2

| Enzyme | Ampicillin | Chloramphenicol | Kanamycin | Efficiency |
|---|---|---|---|---|
| None | 990 | 20000 | 4 | $4/2 \times 10^4 = 0.02\%$ |
| Cre only | 280 | 3640 | 0 | 0 |
| Integrase* only | 1040 | 27000 | 9 | $9/2.7 \times 10^4 = 0.03\%$ |
| Integrase* + Cre | 110 | 1110 | 76 | $76/1.1 \times 10^3 = 6.9\%$ |

*Integrase reactions also contained IHF.

Analysis: The Cre protein impaired transformation. When adjusted for this effect, the number of kanamycin resistant colonies, compared to the control reactions, increased more than 100 fold when both Cre and Integrase were used. This suggests a specificity of greater than 99%.

Part III: 38 colonies were picked from the Integrase plus Cre plates, miniprep DNAs were made and cut with HindIII to give diagnostic mapping information. Result: All 38 had precisely the expected fragment sizes. Analysis: The Cre plus λ integrase method was observed to have much higher specificity than Cre-alone. Conclusion: The Cre plus λ integrase method was demonstrated. Efficiency and specificity were much higher than for Cre only.

Example 2

Figure 4A:
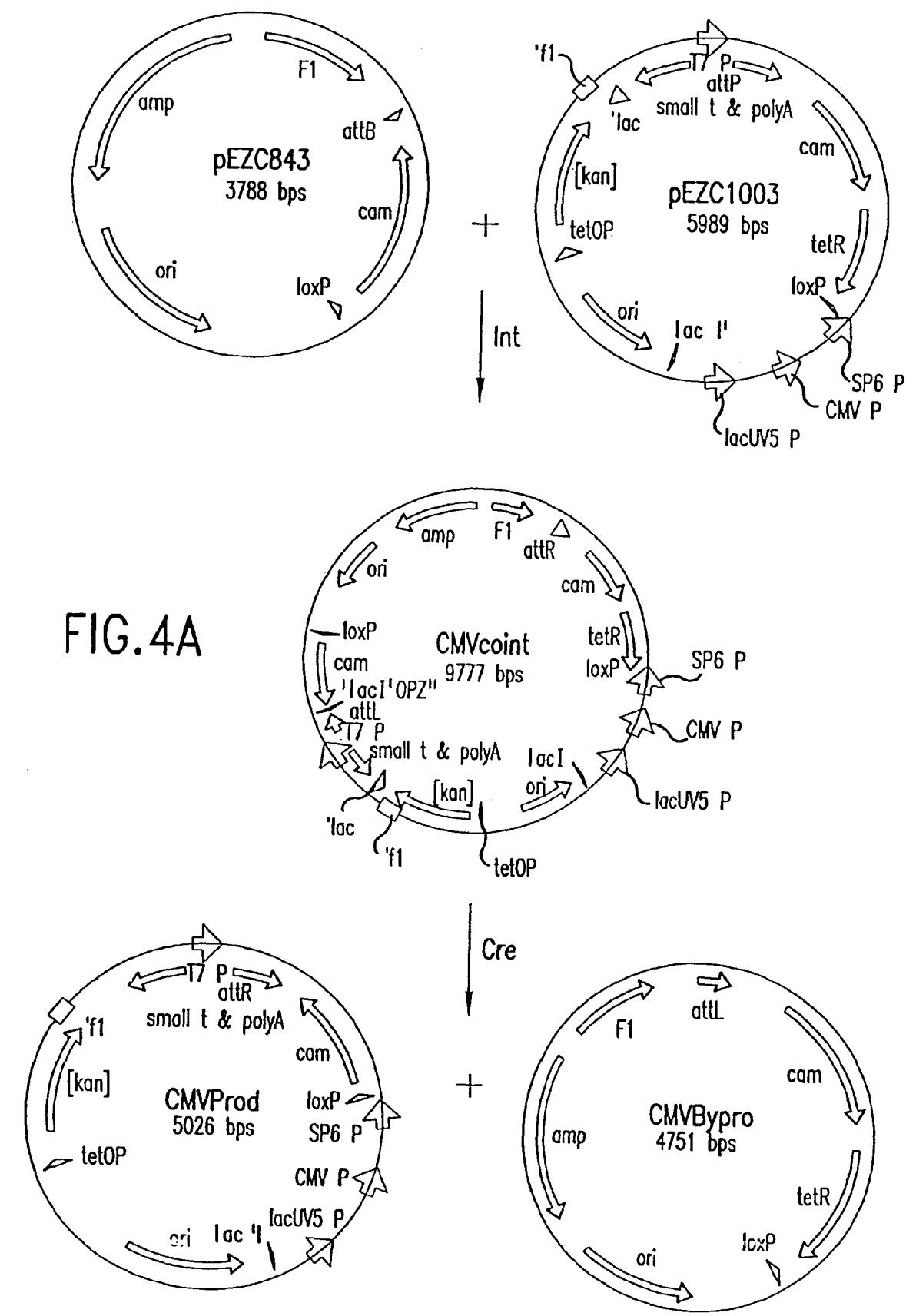
FIG. 4A depicts an application of the in vitro method of recombinational cloning to subclone the chloramphenicol acetyl transferase gene into a vector for expression in eukaryotic cells. The Insert Donor plasmid, pEZC843, is comprised of the chloramphenicol acetyl transferase gene of E. coli, cloned between loxP and attb sites such that the loxP site is positioned at the 5'-end of the gene. The Vector Donor plasmid, pEZC1003, contains the cytomegalovirus eukaryotic promoter apposed to a loxP site. The supercoiled plasmids were combined with lambda Integrase and Cre recombinase in vitro. After incubation, competent E. coli cells were transformed with the recombinational reaction solution. Aliquots of transformations were spread on agar plates containing kanamycin to select for the Product molecule (here CMVProd).

Using In vitro Recombinational Cloning to Subclone the Chloramphenicol Acetyl Transferase Gene into a Vector for Expression in Eukaryotic Cells (FIG. 4A)

Figure 4B:
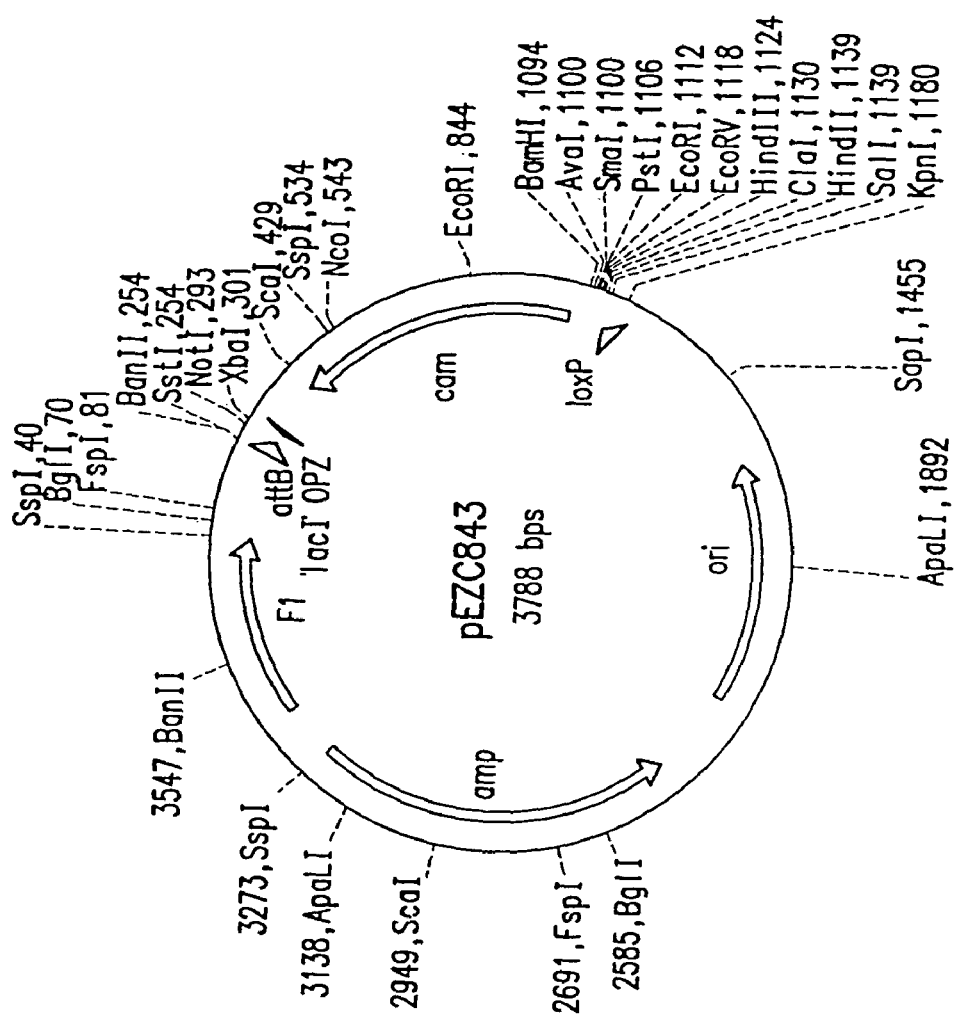
FIG. 4B depicts a restriction map of pEZC843.
Figure 4C:
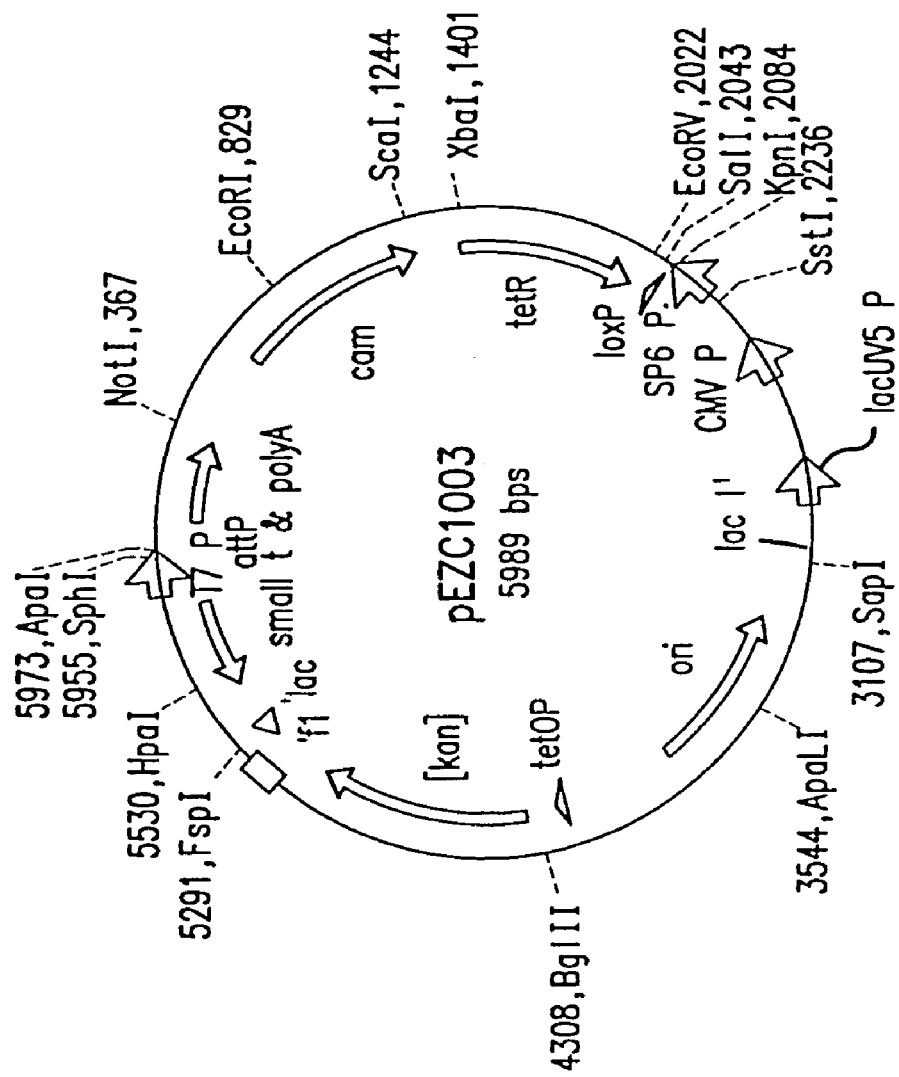
FIG. 4C depicts a restriction map of pEZC1003.
Figure 4D:
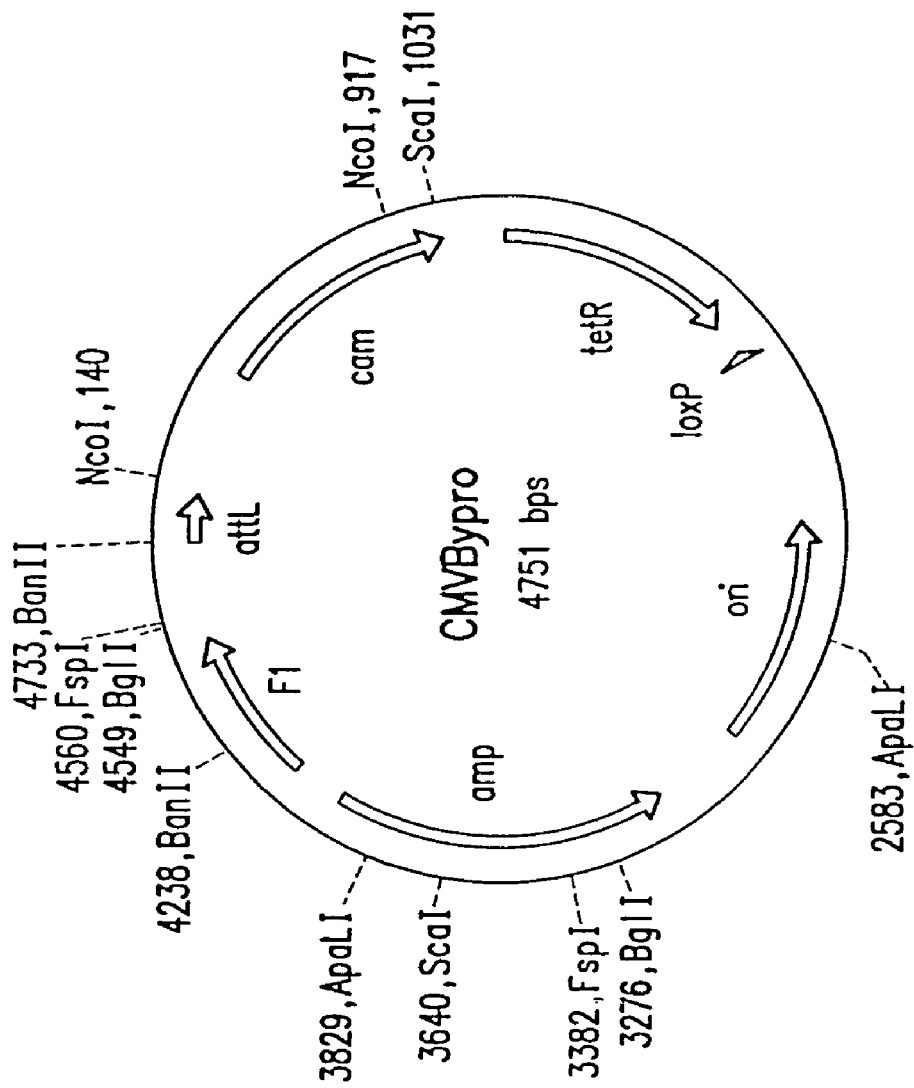
FIG. 4D depicts a restriction map of CMVBypro.
Figure 4E:
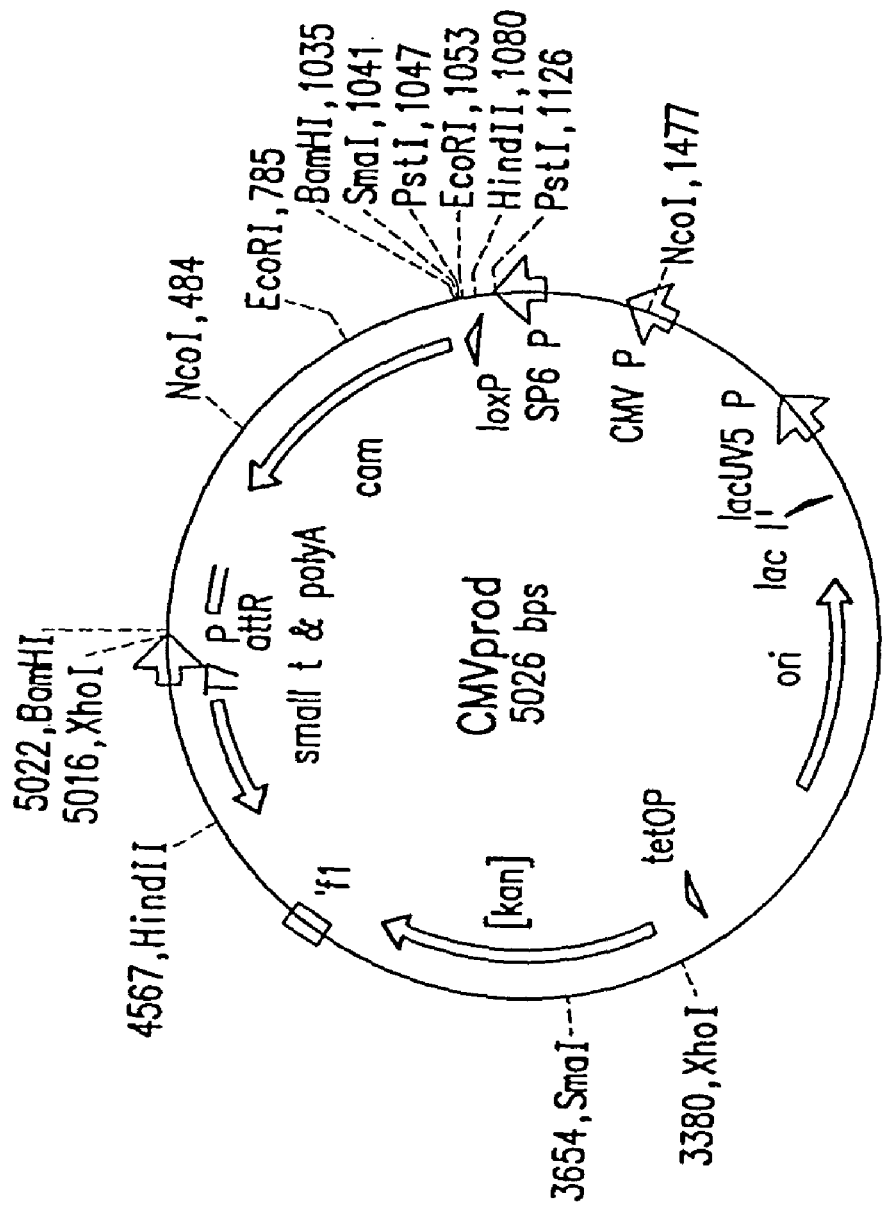
FIG. 4E depicts a restriction map of CMVProd.
Figure 4F:
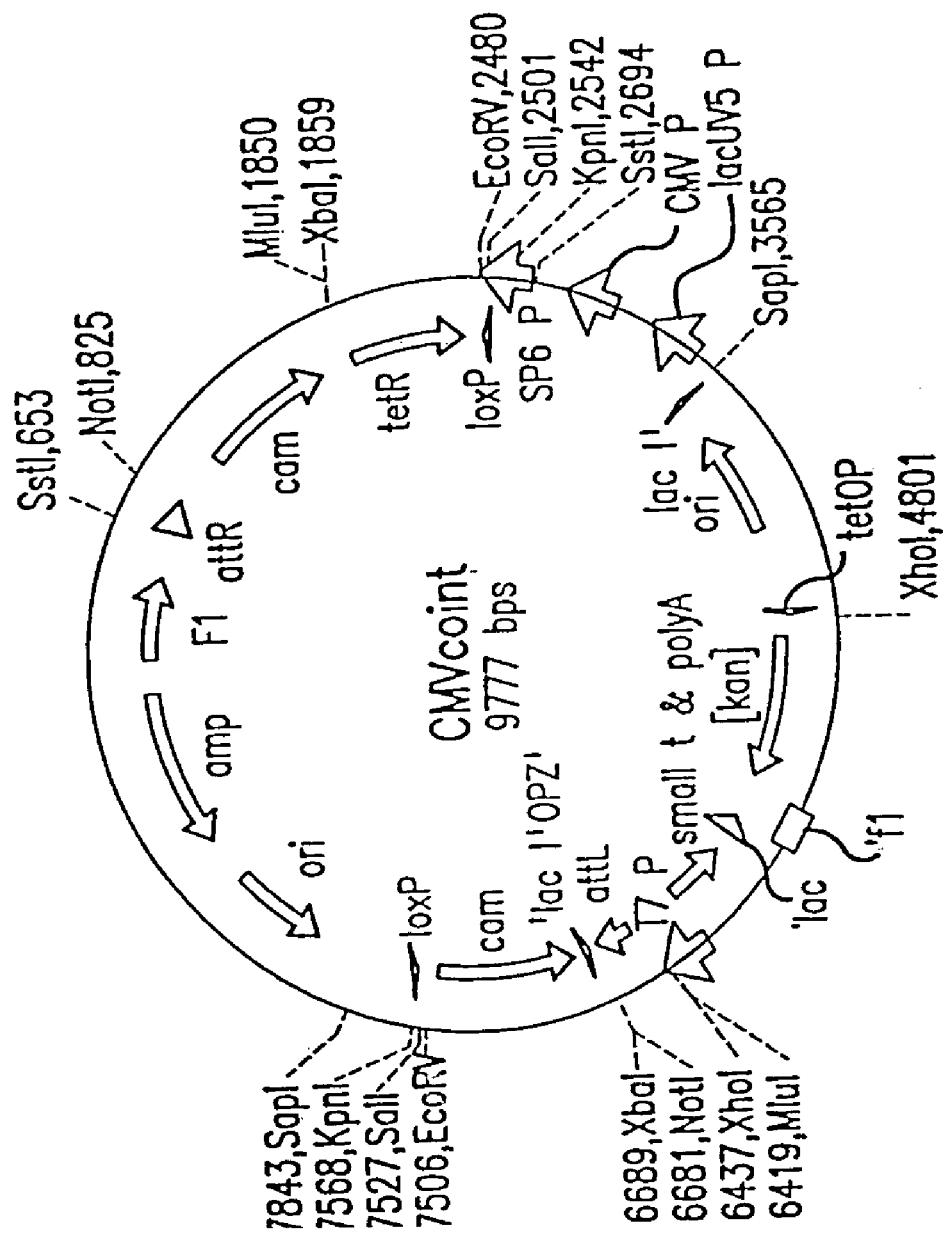
FIG. 4F depicts a restriction map of CMVcoint.

An Insert Donor plasmid, pEZC843, was constructed, comprising the chloramphenicol acetyl transferase gene of E. coli, cloned between loxP and attB sites such that the loxP site was positioned at the 5'-end of the gene (FIG. 4B). A Vector Donor plasmid, pEZC1003, was constructed, which contained the cytomegalovirus eukaryotic promoter apposed to a loxP site (FIG. 4C). One microliter aliquots of each supercoiled plasmid (about 50 ng crude miniprep DNA) were combined in a ten microliter reaction containing equal parts of lambda integrase buffer (50 mM Tris-HCl, pH 7.8, 70 mM KCl, 5 mM spermidine, 0.5 mM EDTA, 0.25 mg/ml bovine serum albumin) and Cre recombinase buffer (50 mM Tris-HCl, pH 7.5, 33 mM NaCl, 5 mM spermidine, 0.5 mg/ml bovine serum albumin), two units of Cre recombinase, 16 ng integration host factor, and 32 ng lambda integrase. After incubation at 30° C. for 30 minutes and 75° C. for 10 minutes, one microliter was transformed into competent E. coli strain DH5α (Life Technologies, Inc.). Aliquots of transformations were spread on agar plates containing 200 μg/ml kanamycin and incubated at 37° C.

overnight. An otherwise identical control reaction contained the Vector Donor plasmid only. The plate receiving 10% of the control reaction transformation gave one colony; the plate receiving 10% of the recombinational cloning reaction gave 144 colonies. These numbers suggested that greater than 99% of the recombinational cloning colonies contained the desired product plasmid. Miniprep DNA made from six recombinational cloning colonies gave the predicted size plasmid (5026 base pairs), CMVProd. Restriction digestion with NcoI gave the fragments predicted for the chloramphenicol acetyl transferase cloned downstream of the CMV promoter for all six plasmids.

Example 3

Subcloned DNA Segments Flanked by attB Sites without Stop Codons

Part I: Background

The above examples are suitable for transcriptional fusions, in which transcription crosses recombination sites. However, both attR and loxP sites contain multiple stop codons on both strands, so translational fusions can be difficult, where the coding sequence must cross the recombination sites, (only one reading frame is available on each strand of loxP sites) or impossible (in attR or attL).

A principal reason for subcloning is to fuse protein domains. For example, fusion of the glutathione S-transferase (GST) domain to a protein of interest allows the fusion protein to be purified by affinity chromatography on glutathione agarose (Pharmacia, Inc., 1995 catalog). If the protein of interest is fused to runs of consecutive histidines (for example His6), the fusion protein can be purified by affinity chromatography on chelating resins containing metal ions (Qiagen, Inc.). It is often desirable to compare amino terminal and carboxy terminal fusions for activity, solubility, stability, and the like.

The attB sites of the bacteriophage λ integration system were examined as an alternative to loxP sites, because they are small (25 bp) and have some sequence flexibility (Nash, H. A. et al., *Proc. Natl. Acad Sci.* USA 84:4049-4053 (1987). It was not previously suggested that multiple mutations to remove all stop codes would result in useful recombination sites for recombinational subcloning.

Using standard nomenclature for site specific recombination in lambda bacteriophage (Weisber, in *Lambda III*, Hendrix, et al., eds., Cold Spring Harbor Laboratory, Cold Spring Harbor, N.Y. (1989)), the nucleotide regions that participate in the recombination reaction in an *E. coli* host cell are represented as follows:

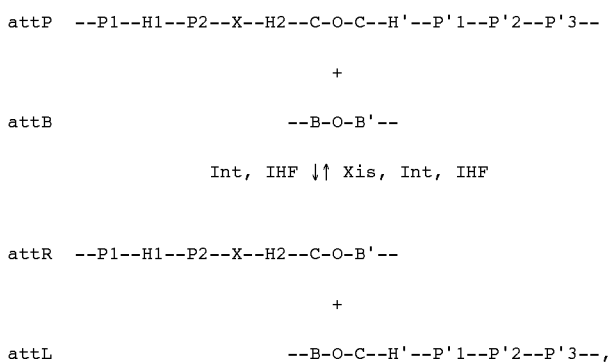

where: O represents the 15 bp core DNA sequence found in both the phage and *E. coli* genomes; B and B' represent approximately 5 bases adjacent to the core in the *E. coli* genome; and P1, H1, P2, X, H2, C, C', H', P'1, P'2, and P'3 represent known DNA sequences encoding protein binding domains in the bacteriophage λ genome.

The reaction is reversible in the presence of the protein Xis (excisionase); recombination between attL and attR precisely excise the λ genome from its integrated state, regenerating the circular λ genome containing attP and the linear *E. coli* genome containing attB.

Part II: Construction and Testing of Plasmids Containing Mutant att Sites

Mutant attL and attR sites were constructed. Importantly, Landy et al. (*Ann. Rev. Biochem.* 58:913 (1989)) observed that deletion of the P1 and H1 domains of attP facilitated the excision reaction and elimninated the integration reaction, thereby making the excision reaction irreversible. Therefore, as mutations were introduced in attR, the P1 and H1 domains were also deleted. attR sites in the present example lack the P1 and H1 regions and have the NdeI site removed (base 27630 changed from C to G), and contain sequences corresponding to bacteriophage λ coordinates 27619-27738 (GenBank release 92.0, bg:LAMCG, "Complete Sequence of Bacteriophage Lambda").

The sequence of attB produced by recombination of wild type attL and attR sites is:

```
                    B            O           B'
attBwt:  5' AGCCT GCTTTTTTATACTAA CTTGA 3'   (SEQ. ID NO:31)

3' TCGGA CGAAAAAATATGATT GAACT 5'
```

The stop codons are italicized and underlined. Note that sequences of attL, attR, and attP can be derived from the attB sequence and the boundaries of bacteriophage λ contained within attL and attR (coordinates 27619 to 27818).

When mutant attR1 and attL1 sites were recombined the sequence attB1 was produced (mutations in bold, large font):

```
          B            O           B'
attB1:  5' AGCCT GCTTTTTTGTACAAA CTTGT 3'    (SEQ. ID NO:6)

3' TCGGA CGAAAAAACATGTTT GAACA 5'
```

Note that the four stop codons are gone.

When an additional mutation was introduced in the attR1 and attL1 sequences (bold), attR2 and attL2 sites resulted. Recombination of attR2 and attL2 produced the attB2 site:

```
          B            O           B'
attB2:  5' AGCCT GCTTTCTTGTACAAA CTTGT 3'    (SEQ. ID NO:7)

3' TCGGA CGAAAGAACATGTTT GAACA 5'
```

The recombination activities of the above attL and attR sites were assayed as follows. The attB site of plasmid pEZC705 (FIG. 2B) was replaced with attLwt, attL1, or attL2. The attP site of plasmid pEZC726 (FIG. 2C) was replaced with attRwt (lacking regions P1 and H1), attR1, or attR2. Thus, the resulting plasmids could recombine via their loxP sites, mediated by Cre, and via their attR and attL sites, mediated by Int, Xis, and IHF. Pairs of plasmids were mixed and reacted with Cre, Int, Xis, and IHF, transformed into *E. coli* competent cells, and plated on agar containing kanamycin. The results are presented in Table 3:

TABLE 3

| Vector donor att site | Gene donor att site | # of kanamycin resistant colonies* |
|---|---|---|
| attRwt (pEZC1301) | None | 1 (background) |
| attRwt (pEZC1301) | attLwt (pEZC1313) | 147 |
| attRwt (pEZC1301) | attL1 (pEZC1317) | 47 |
| attRwt (pEZC1301) | attL2 (pEZC1321) | 0 |
| attR1 (pEZC1305) | None | 1 (background) |
| attR1 (pEZC1305) | attLwt (pEZC1313) | 4 |
| attR1 (pEZC1305) | attL1 (pEZC1317) | 128 |
| attR1 (pEZC1305) | attL2 (pEZC1321) | 0 |
| attR2 (pEZC1309) | None | 9 (background) |
| attR2 (pEZC1309) | attLwt (pEZC1313) | 0 |
| attR2 (pEZC1309) | attL2 (pEZC1317) | 0 |
| attR2 (pEZC1309) | attL2 (pEZC1321) | 209 |

(*1% of each transformation was spread on a kanamycin plate.)

The above data show that whereas the wild type att and att1 sites recombine to a small extent, the att1 and att2 sites do not recombine detectably with each other.

Part III. Recombination was demonstrated when the core region of both attB sites flanking the DNA segment of interest did not contain stop codons. The physical state of the participating plasmnids was discovered to influence recombination efficiency.

Figure 5A:
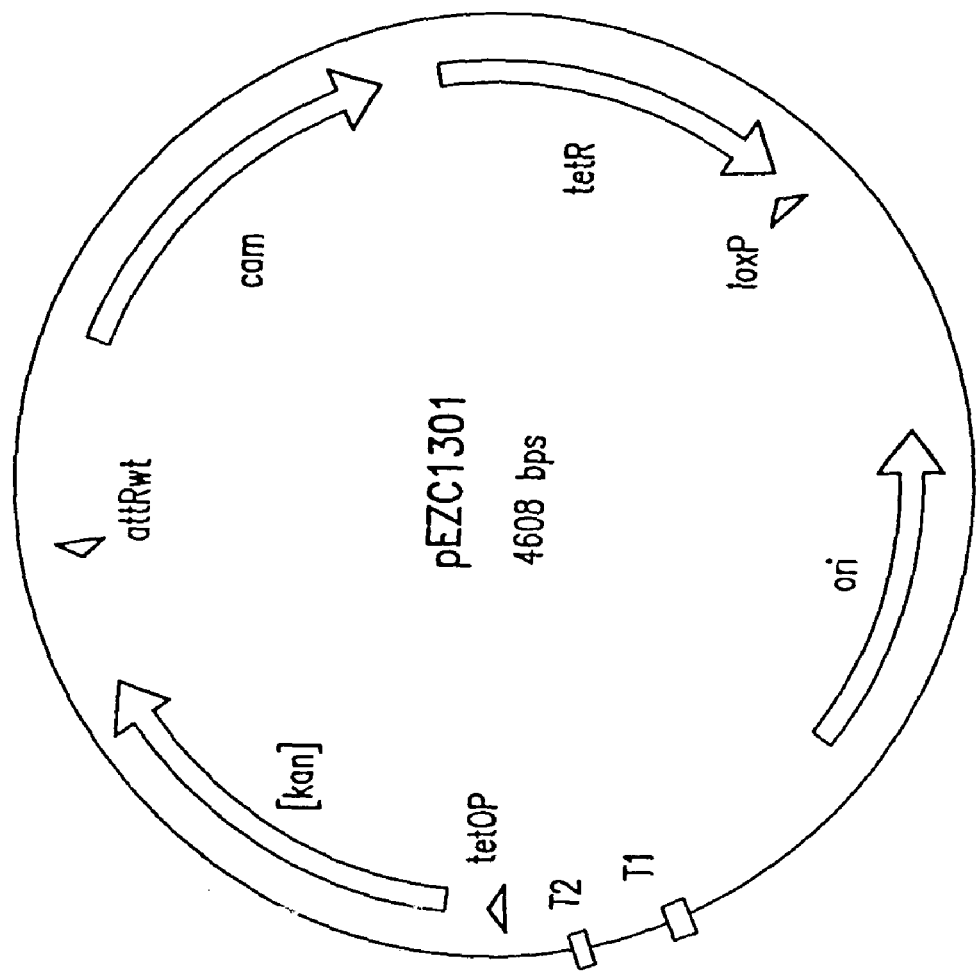
FIG. 5A depicts a vector diagram of pEZC1301.
Figure 5B:
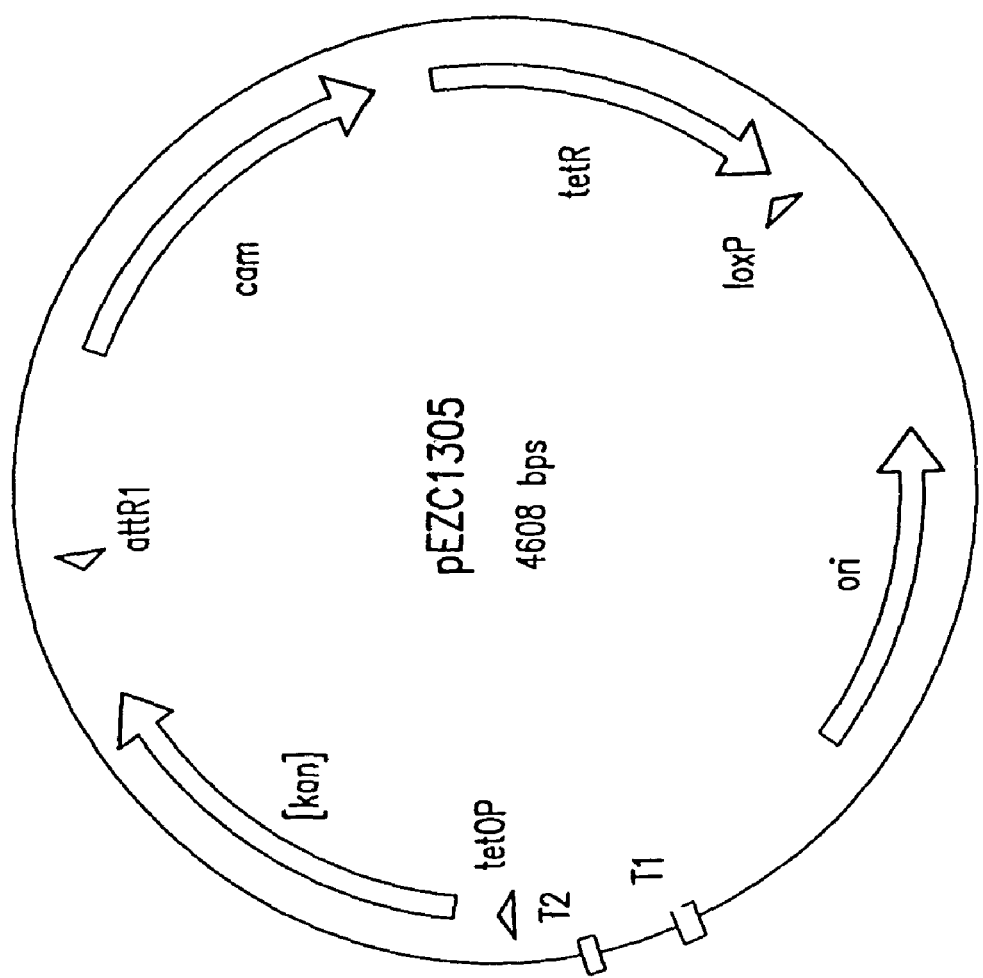
FIG. 5B depicts a vector diagram of pEZC1305.
Figure 5C:
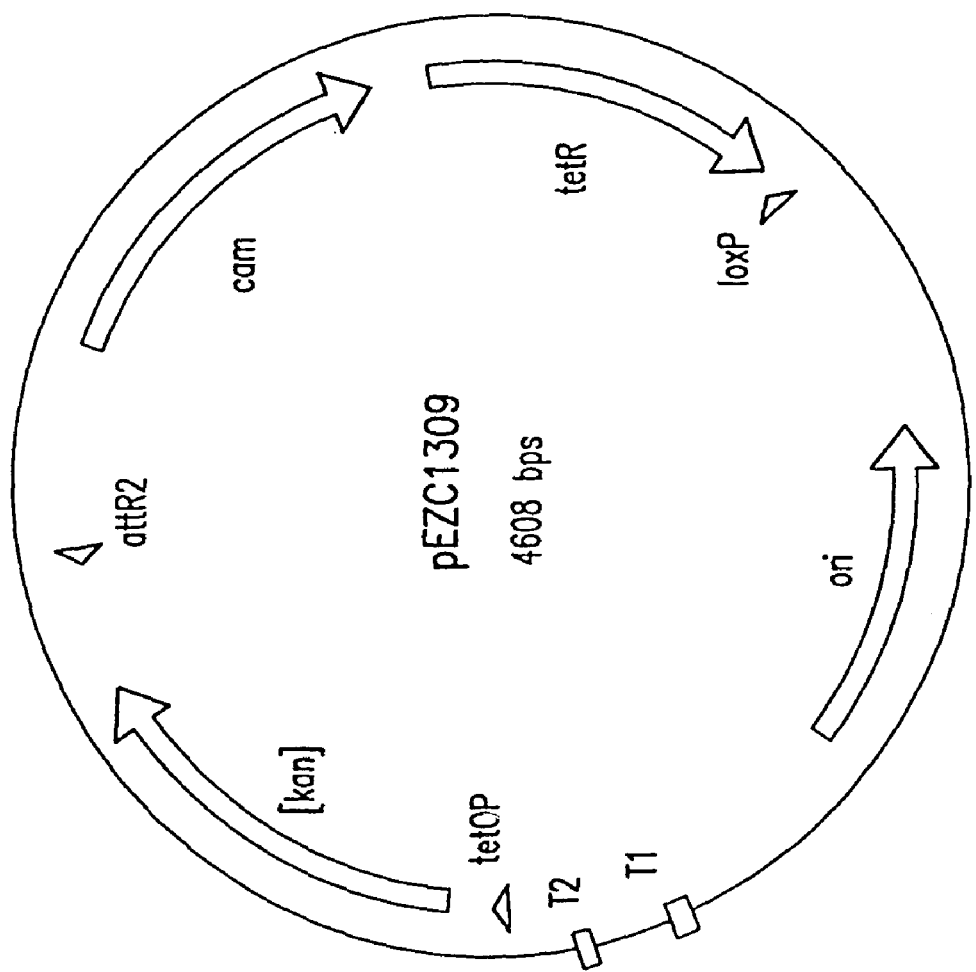
FIG. 5C depicts a vector diagram of pEZC1309.
Figure 5D:
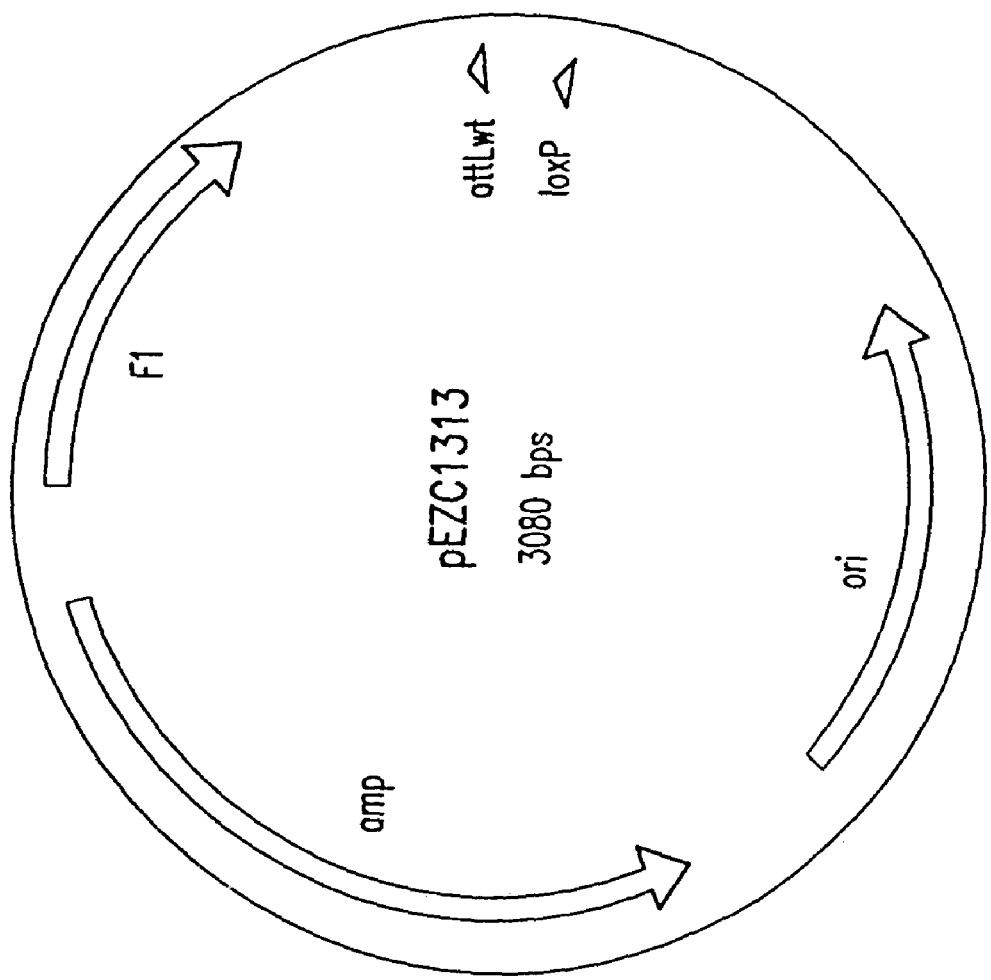
FIG. 5D depicts a vector diagram of pEZC1313.
Figure 5E:
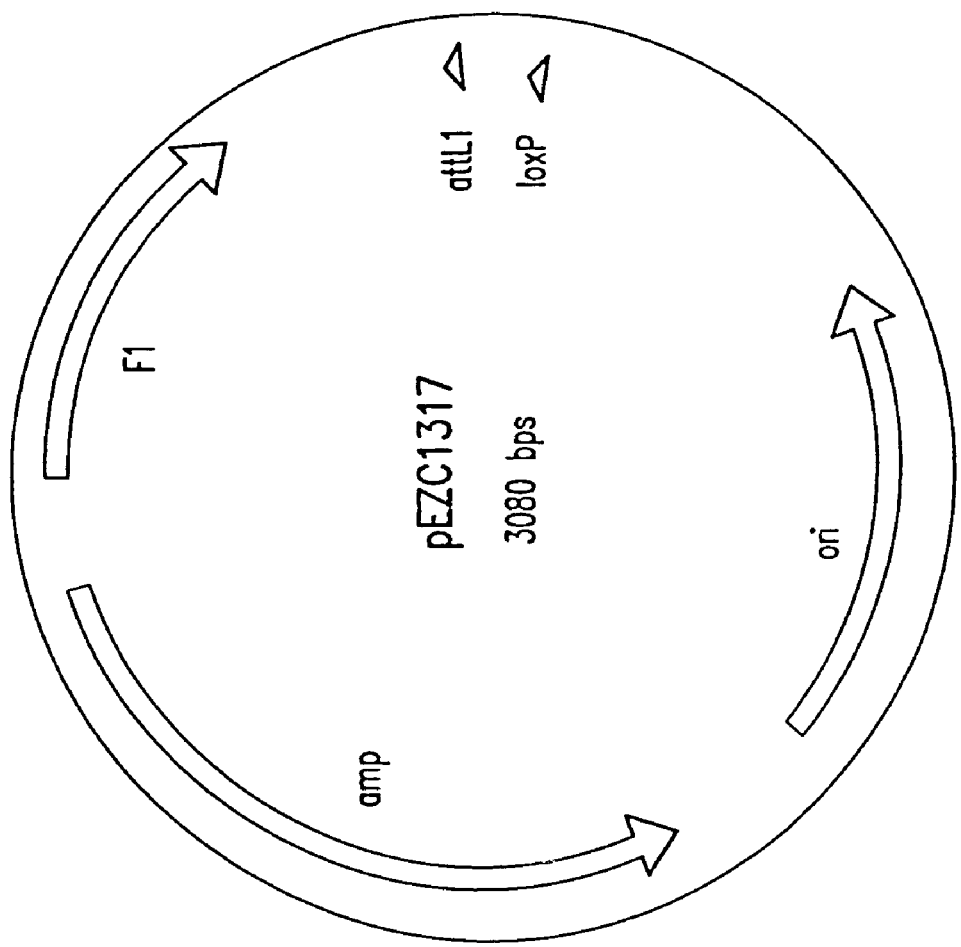
FIG. 5E depicts a vector diagram of pEZC1317.
Figure 5F:
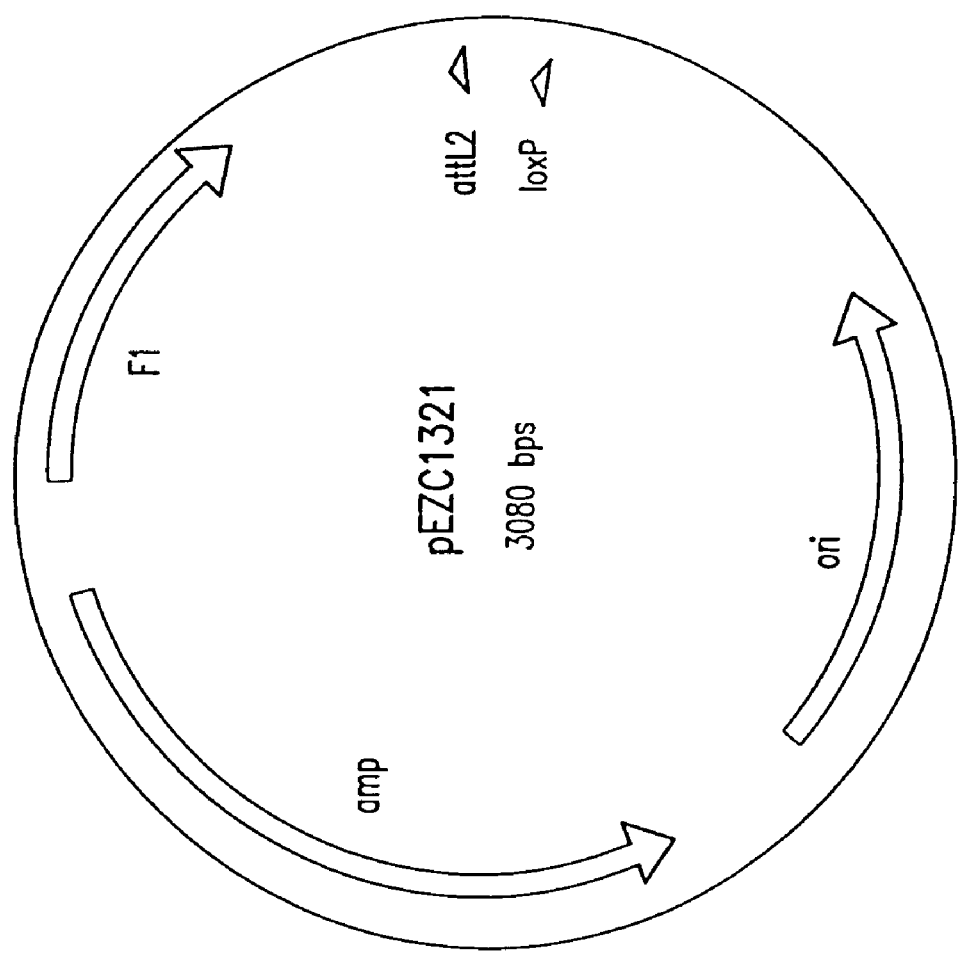
FIG. 5F depicts a vector diagram of pEZC1321.
Figure 5G:
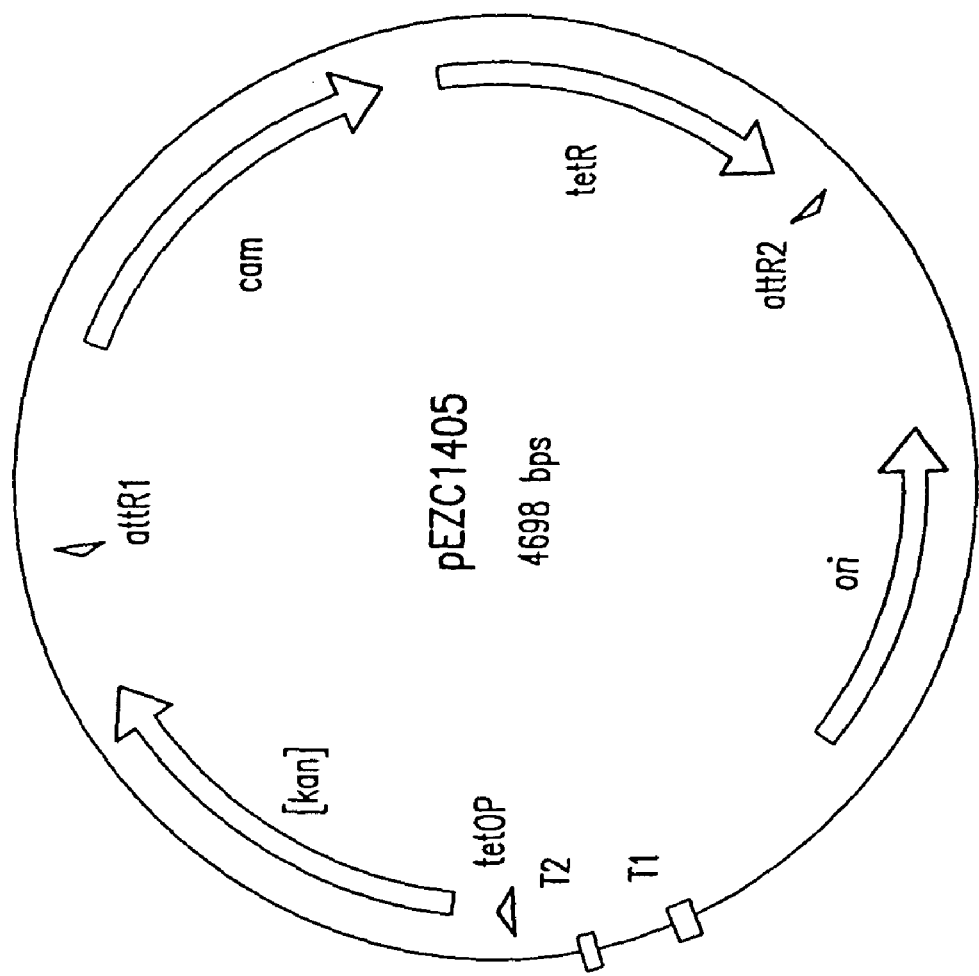
FIG. 5G depicts a vector diagram of pEZC1405.

The appropriate att sites were moved into pFZC705 and pEZC726 to make the plasmids pEZC1405 (FIG. 5G) (attR1 and attR2) and pEZC1502 (FIG. 5H) (attL1 and attL2). The desired DNA segment in this experiment was a copy of the chloramphenicol resistance gene cloned between the two attL sites of pEZC1502. Pairs of plasmids were recombined in vitro using Int, Xis, and IHF (no Cre because no loxP sites were present). The yield of desired kanamycin resistant colonies was determined when both parental plasmids were circular, or when one plasmid was circular and the other linear as presented in Table 4:

TABLE 4

| Vector donor[1] | Gene donor[1] | Kanamycin resistant colonies[2] |
|---|---|---|
| Circular pEZC1405 | None | 30 |
| Circular pEZC1405 | Circular pEZC1502 | 2680 |
| Linear pEZC1405 | None | 90 |
| Linear pEZC1405 | Circular pEZC1502 | 172000 |
| Circular pEZC1405 | Linear pEZC1502 | 73000 |

[1]DNAs were purified with Qiagen columns, concentrations determined by A260, and linearized with Xba I (pEZC1405) or AlwN I (pEZC1502). Each reaction contained 100 ng of the indicated DNA. All reactions (10 μl total) contained 3 μl of enzyme mix (Xis, Int, and IHF). After incubation (45 minutes at 25°, 10 minutes at 65°), one μl was used to transform *E. coli* DH5α cells.
[2]Number of colonies expected if the entire transformation reaction (1 ml) had been plated. Either 100 μl or 1 μl of the transformations were actually plated.

Analysis: Recombinational cloning using mutant attR and attL sites was confirmed. The desired DNA segment is subcloned between attB sites that do not contain any stop codons in either strand. The enhanced yield of Product DNA (when one parent was linear) was unexpected because of earlier observations that the excision reaction was more efficient when both participating molecules were supercoiled and proteins were limiting (Nunes-Duby et al., *Cell* 50:779-788 (1987).

Example 4

Demonstration of Recombinational Cloning without Inverted Repeats

Part I: Rationale

The above Example 3 showed that plasmids containing inverted repeats of the appropriate recombination sites (for example, attL1 and attL2 in plasmid pEZC1502) (FIG. 5H) could recombine to give the desired DNA segment flanked by attB sites without stop codons, also in inverted orientation. A concern was the in vivo and in vitro influence of the inverted repeats. For example, transcription of a desired DNA segment flanked by attB sites in inverted orientation could yield a single stranded RNA molecule that might form a hairpin structure, thereby inhibiting translation.

Inverted orientation of similar recombination sites can be avoided by placing the sites in direct repeat arrangement att sites. If parental plasmids each have a wild type attL and wild type attR site, in direct repeat the Int, Xis, and IHF proteins will simply remove the DNA segment flanked by those sites in an intramolecular reaction. However, the mutant sites described in the above Example 3 suggested that it might be possible to inhibit the intramolecular reaction while allowing the intermolecular recombination to proceed as desired.

Figure 5H:
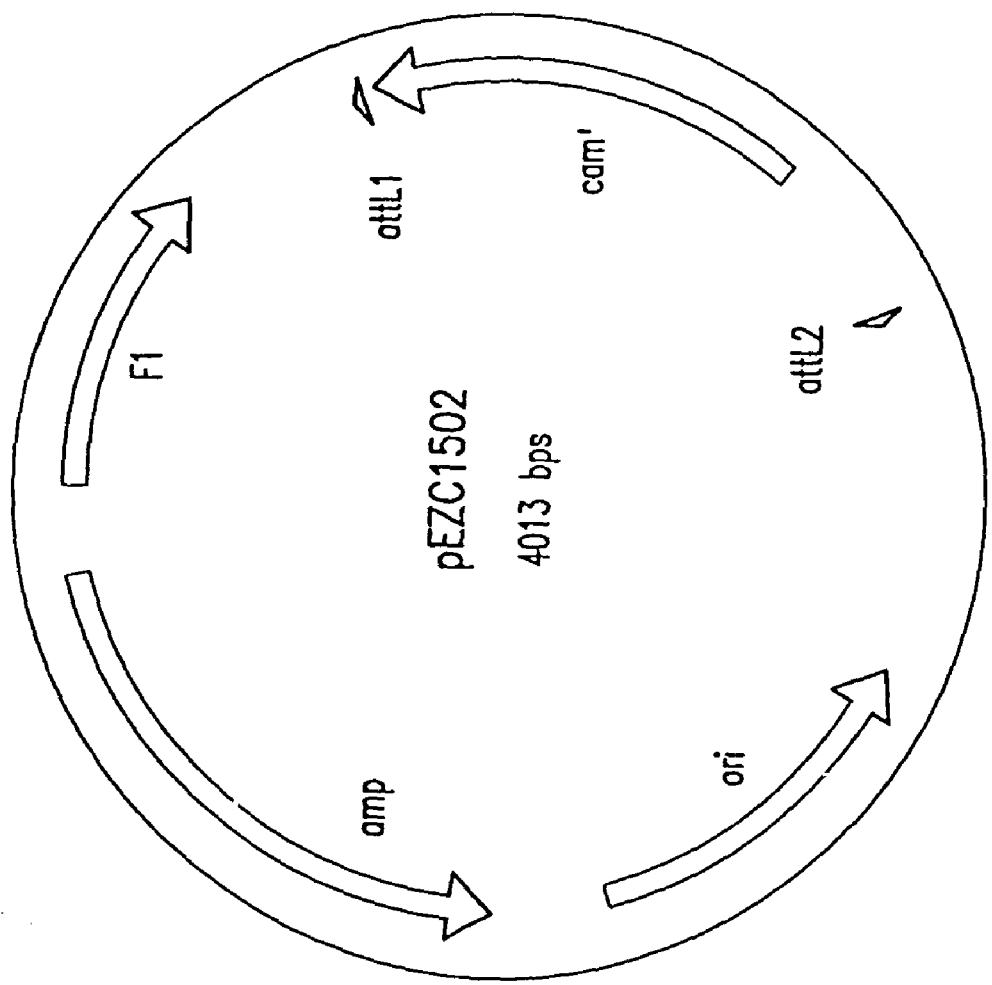
FIG. 5H depicts a vector diagram of pEZC1502.
Figure 6A:
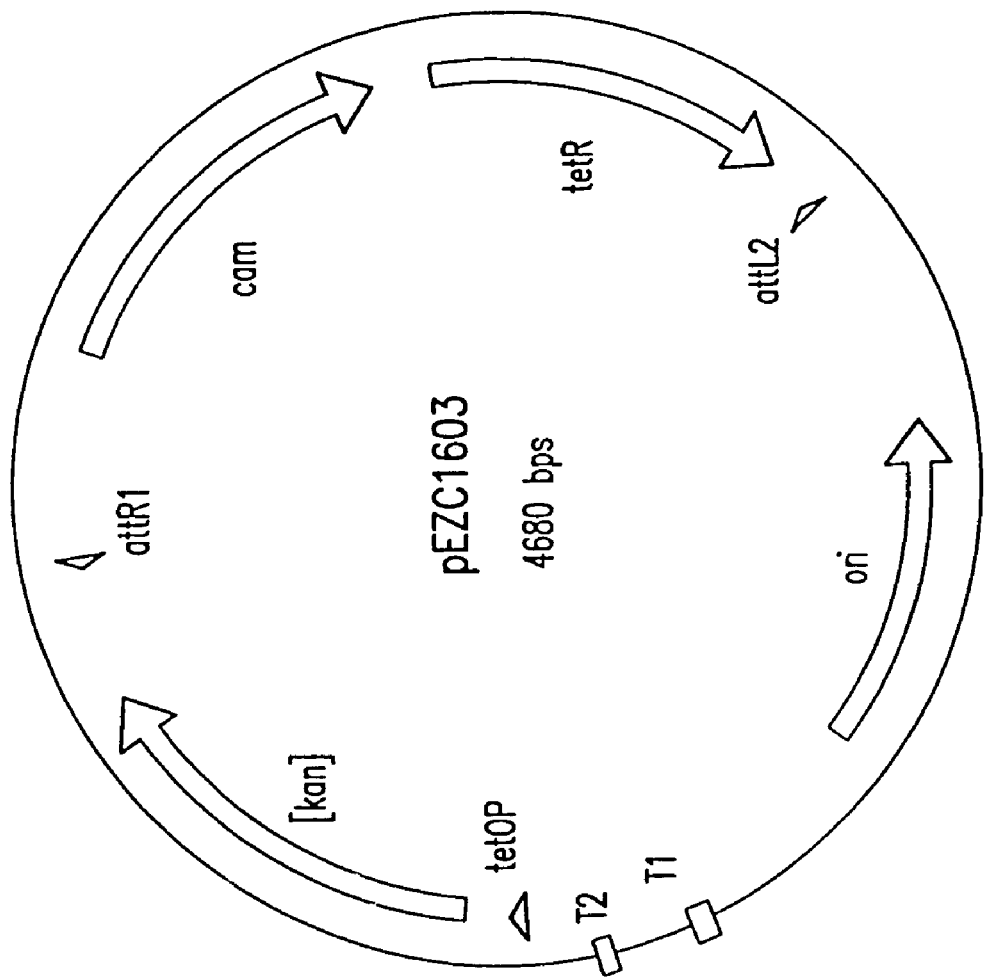
FIG. 6A depicts a vector diagram of pEZC1603.

Part II: Structure of Plasmids without Inverted Repeats for Recombinational Cloning The attR2 sequence in plasmid pEZC1405 (FIG. 5G) was replaced with attL2, in the opposite orientation, to make pEZC1603 (FIG. 6A). The attL2 sequence of pEZC1502 (FIG. 5H) was replaced with attR2, in the opposite orientation, to make pEZC1706 (FIG. 6B). Each of these plasmids contained mutations in the core region that make intramolecular reactions between att1 and att2 cores very inefficient (see Example 3, above).

Plasmids pEZC1405, pEZC1502, pEZC1603 and pEZC1706 were purified on Qiagen columns (Qiagen, Inc.). Aliquots of plasmids pEZC1405 and pEZC1603 were linearized with Xba I. Aliquots of plasmids pEZC1502 and pEZC1706 were linearized with AlwN I. One hundred ng of plasmids were mixed in buffer (equal volumes of 50 mM Tris HCl pH 7.5, 25 mM Tris HCl pH 8.0, 70 mM KCl, 5 mM spermidine, 0.5 mM EDTA, 250 μg/ml BSA, 10% glycerol) containing Int (43.5 ng), Xis (4.3 ng) and IHF (8.1 ng) in a final volume of 10 μl. Reactions were incubated for 45 minutes at 25° C., 10 minutes at 65° C., and 1 μl was transformed into $E.\ coli$ DH5α. After expression, aliquots were spread on agar plates containing 200 μg/ml kanamycin and incubated at 37° C.

Results, expressed as the number of colonies per 1 μl of recombination reaction are presented in Table 5:

TABLE 5

| Vector Donor | Gene Donor | Colonies | Predicted % product |
|---|---|---|---|
| Circular 1405 | — | 100 | — |
| Circular 1405 | Circular 1502 | 3740 | 3640/3740 = 97% |
| Linear 1405 | — | 90 | — |
| Linear 1405 | Circular 1502 | 172,000 | 171,910/172,000 = 99.9% |
| Circular 1405 | Linear 1502 | 73,000 | 72,900/73,000 = 99.9% |
| Circular 1603 | — | 80 | — |
| Circular 1603 | Circular 1706 | 410 | 330/410 = 80% |
| Linear 1603 | — | 270 | — |
| Linear 1603 | Circular 1706 | 7000 | 6730/7000 = 96% |
| Circular 1603 | Linear 1706 | 10,800 | 10,530/10,800 = 97% |

Analysis. In all configurations, i.e., circular or linear, the pEZC1405×pEZC1502 pair (with att sites in inverted repeat configuration) was more efficient than pEZC1603× pEZC1706 pair (with att sites mutated to avoid hairpin formation). The pEZC1603×pEZC1706 pair gave higher backgrounds and lower efficiencies than the pEZC1405× pEZC1502 pair. While less efficient, 80% or more of the colonies from the pEZC160333 pEZC1706 reactions were expected to contain the desired plasmid product. Making one partner linear stimulated the reactions in all cases.

Part III: Confirmation of Product Plasmids' Structure

Six colonies each from the linear pEZC1405 (FIG. 5G)× circular pEZC1502 (FIG. 5H), circular pEZC1405×linear pEZC1502, linear pEZC1603 (FIG. 6A)×circular pEZC1706 (FIG. 6B), and circular pEZC1603×linear pEZC1706 reactions were picked into rich medium and miniprep DNAs were prepared. Diagnostic cuts with Ssp I gave the predicted restriction fragments for all 24 colonies.

Analysis. Recombination reactions between plasmids with mutant attL and attR sites on the same molecules gave the desired plasmid products with a high degree of specificity.

Example 5

Recombinational Cloning with a Toxic Gene

Part I: Background

Restriction enzyme Dpn I recognizes the sequence GATC and cuts that sequence only if the A is methylated by the dam methylase. Most commonly used $E.\ coli$ strains are dam$^+$. Expression of Dpn I in dam$^+$ strains of $E.\ coli$ is lethal because the chromosome of the cell is chopped into many pieces. However, in dam$^-$ cells expression of Dpn I is innocuous because the chromosome is immune to Dpn I cutting.

In the general recombinational cloning scheme, in which the vector donor contains two segments C and D separated by recombination sites, selection for the desired product depends upon selection for the presence of segment D, and the absence of segment C. In the original Example segment D contained a drug resistance gene (Km) that was negatively controlled by a repressor gene found on segment C. When C was present, cells containing D were not resistant to kanamycin because the resistance gene was turned off.

The Dpn I gene is an example of a toxic gene that can replace the repressor gene of te above embodiment. If segment C expresses the Dpn I gene product, transforming plasmid CD into a dam$^+$ host kills the cell. If segment D is transferred to a new plasmid, for example by recombinational cloning, then selecting for the drug marker will be successful because the toxic gene is no longer present.

Part II: Construction of a Vector Donor Using Dpn I as a Toxic Gene

The gene encoding Dpn I endonuclease was amplified by PCR using

5'CCA CCA CAA ACG CGT CCA TGG AAT TAC ACT TTA ATT TAG3' (SEQ. ID NO:17) and

5'CCA CCA CAA GTC GAC GCA TGC CGA CAG CCT TCC AAA TGT3' (SEQ. ID NO:18)

and a plasmid containing the Dpn I gene (derived from plasmids obtained from Sanford A. Lacks, Brookhaven National Laboratory, Upton, N.Y., also available from American Type Culture Collection as ATCC 67494) as the template.

Additional mutations were introduced into the B and B' regions of attL and attR, respectively, by amplifying existing attL and attR domains with primers containing the desired base changes. Recombination of the mutant attL3 (made with oligo Xis115) and attR3 (made with oligo Xis112) yielded attB3 with the following sequence (differences from attB1 in bold):

```
    B         O         B'
ACCCA GCTTTCTTGTACAAA GTGGT    (SEQ. ID NO:8)

TGGGT CGAAAGAACATGTTT CACCA
```

Figure 7A:
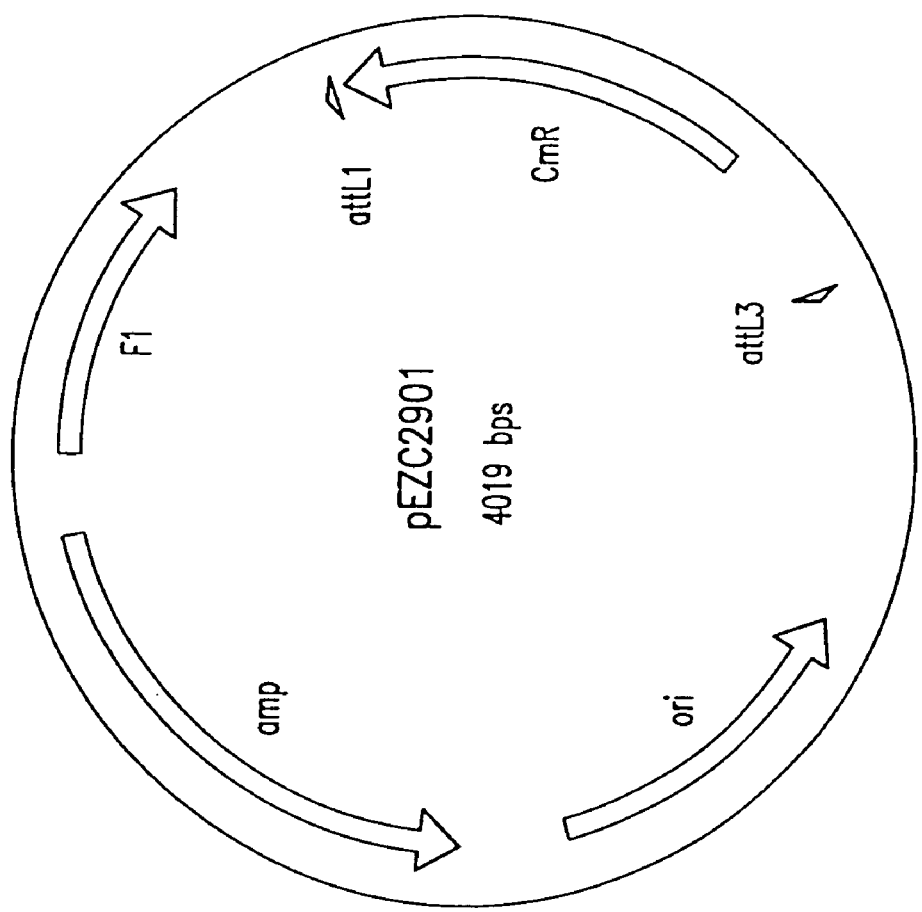
FIG. 7A depicts a vector diagram of pEZC2901.
Figure 7B:
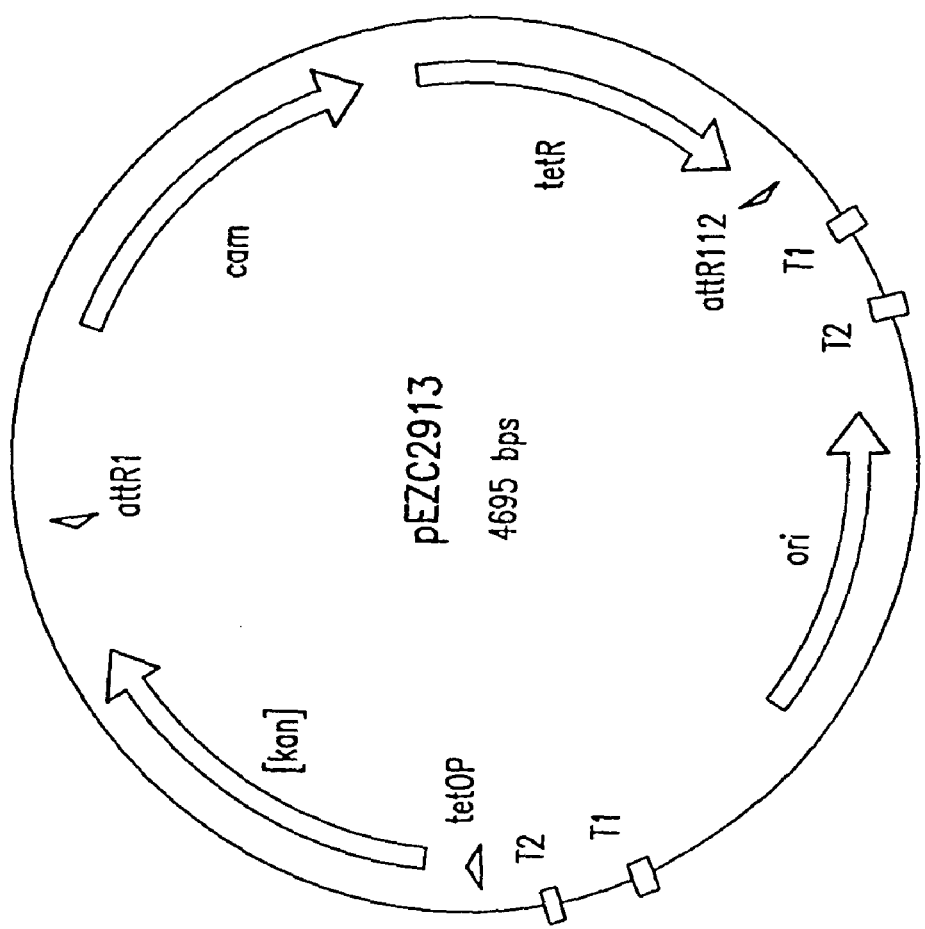
FIG. 7B depicts a vector diagram of pEZC2913.
Figure 7C:
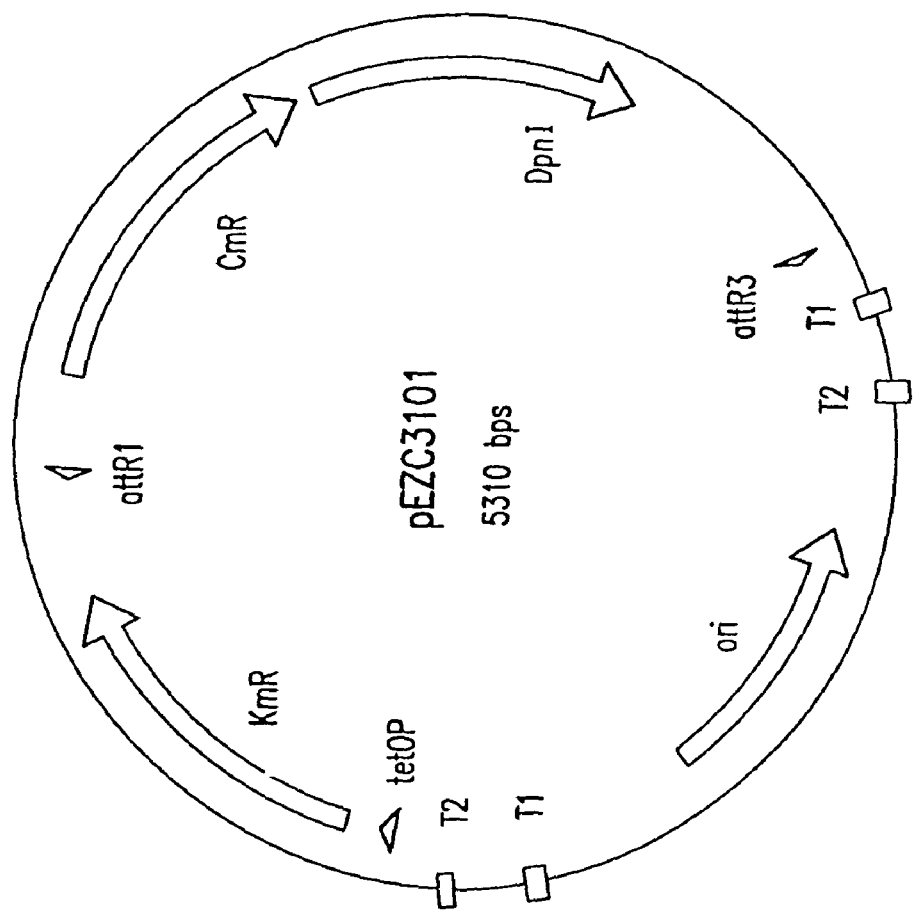
FIG. 7C depicts a vector diagram of pEZC3101.

The attL3 sequence was cloned in place of attL2 of an existing Gene Donor plasmid to give the plasmid pEZC2901 (FIG. 7A). The attR3 sequence was cloned in place of attR2 in an existing Vector Donor plasmid to give plasmid pEZC2913 (FIG. 7B) Dpn I gene was cloned into plasmid pEZC2913 to replace the tet repressor gene. The resulting Vector Donor plasmid was named pEZC3101 (FIG. 7C). When pEZC3101 was transformed into the dam⁻ strain SCS110 (Stratagene), hundreds of colonies resulted. When the same plasmid was transformed into the dam+ strain DH5α, only one colony was produced, even though the DH5α cells were about 20 fold more competent than the SCS110 cells. When a related plasmid that did not contain the Dpn I gene was transformed into the same two cell lines, 28 colonies were produced from the SCS110 cells, while 448 colonies resulted from the DH5α cells. This is evidence that the Dpn I gene is being expressed on plasmid pEZC3101 (FIG. 7C), and that it is killing the dam⁺ DH5α cells but not the dam⁻ SCS110 cells.

Part III: Demonstration of Recombinational Cloning Using Dpn I Selection

Figure 7D:
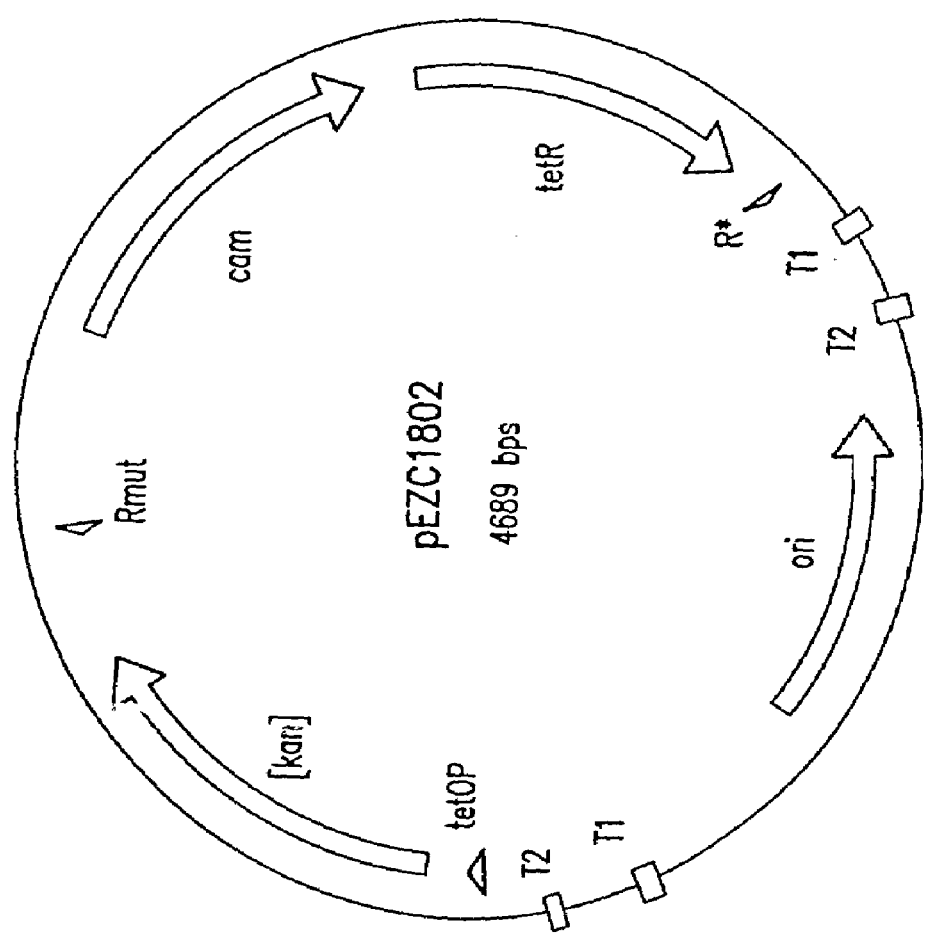
FIG. 7D depicts a vector diagram of pEZC1802.

A pair of plasmids was used to demonstrate recombinational cloning with selection for product dependent upon the toxic gene Dpn I. Plasmid pEZC3101 (FIG. 7C) was linearized with Mlu I and reacted with circular plasmid pEZC2901 (FIG. 7A). A second pair of plasmids using selection based on control of drug resistance by a repressor gene was used as a control: plasmid pEZC1802 (FIG. 7D) was linearized with Xba I and reacted with circular plasmid pEZC1502 (FIG. 5H). Eight microliter reactions containing the same buffer and proteins Xis, Int, and IHF as in previous examples were incubated for 45 minutes at 25° C., then 10 minutes at 75° C., and 1 µl aliquots were transformed into DH5α (i.e., dam+) competent cells, as presented in Table 6.

TABLE 6

| Reaction # | Vector donor | Basis of selection | Gene donor | Colonies |
|---|---|---|---|---|
| 1 | pEZC3101/Mlu | Dpn I toxicity | — | 3 |
| 2 | pEZC3101/Mlu | Dpn I toxicity | Circular pEZC2901 | 4000 |
| 3 | pEZC1802/Xba | Tet repressor | — | 0 |
| 4 | pEZC1802/Xba | Tet repressor | Circular pEZC1502 | 12100 |

Miniprep DNAs were prepared from four colonies from reaction #2, and cut with restriction enzyme Ssp I. All gave the predicted fragments.

Analysis: Subcloning using selection with a toxic gene was demonstrated. Plasmids of the predicted structure were produced.

Example 6

Cloning of Genes with Uracil DNA Glycosylase and Subcloning of the Genes with Recombinational Cloning to make Fusion Proteins Part I: Converting an Existing Expression Vector to a Vector Donor for Recombinational Cloning A cassette useful for converting existing vectors into functional Vector Donors was made as follows. Plasmid pEZC3101 (FIG. 7C) was digested with Apa I and Kpn I, treated with T4 DNA polymerase and dNTPs to render the ends blunt, further digested with Sma I, Hpa I, and AlwN I to render the undesirable DNA fragments small, and the 2.6 kb cassette containing the attR1-Cm$^R$-Dpn I-attR-3 domains was gel purified. The concentration of the purified cassette was estimated to be about 75 ng DNA/µl.

Figure 8A:
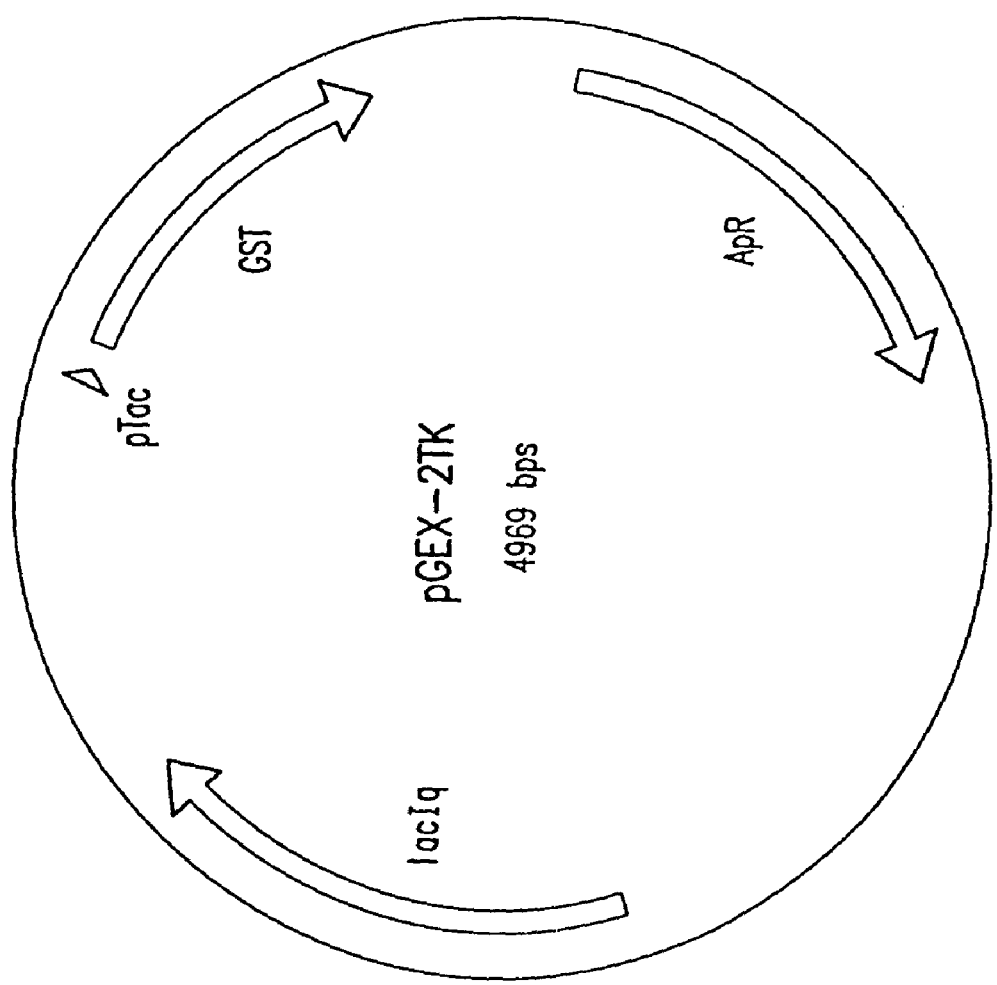
FIG. 8A depicts a vector diagram of pGEX-2TK.
Figure 8B:
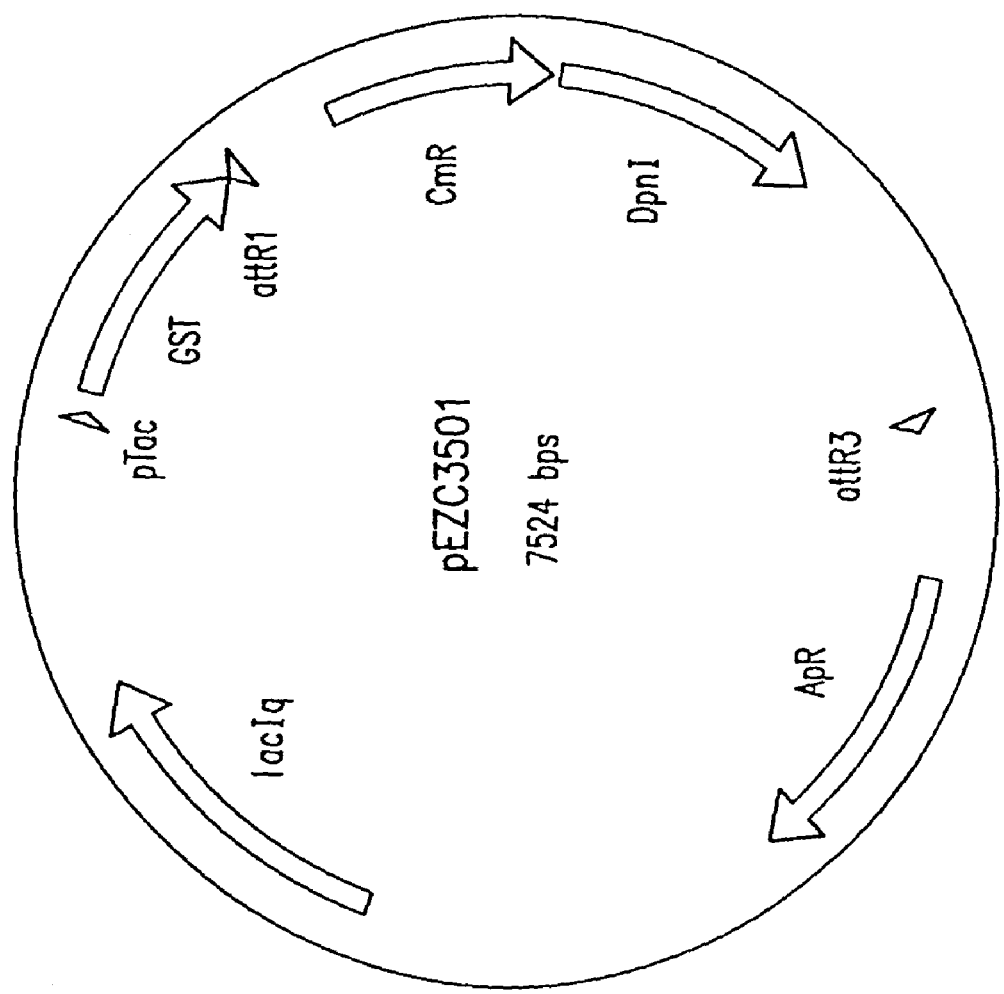
FIG. 8B depicts a vector diagram of pEZC3501.

Plasmid pGEX-2TK (FIG. 8A) (Pharmacia) allows fusions between the protein glutathione S transferase and any second coding sequence that can be inserted in its multiple cloning site. pGEX-2TK DNA was digested with Sma I and treated with alkaline phosphatase. About 75 ng of the above purified DNA cassette was ligated with about 100 ng of the pGEX-2TK vector for 2.5 hours in a 5 µl ligation, then 1 µl was transformed into competent BRL 3056 cells (a dam⁻ derivative of DH10B; dam⁻ strains commercially available include DM1 from Life Technologies, Inc., and SCS 110 from Stratagene). Aliquots of the transformation mixture were plated on LB agar containing 100 µg/ml ampicillin (resistance gene present on pGEX-2TK) and 30 µg/ml chloramphenicol (resistance gene present on the DNA cassette). Colonies were picked and miniprep DNAs were made. The orientation of the cassette in pGEX-2TK was determined by diagnostic cuts with EcoR I. A plasmid with the desired orientation was named pEZC3501 (FIG. 8B).

Part II: Cloning Reporter Genes into an Recombinational Cloning Gene Donor Plasmid in Three Reading Frames Uracil DNA glycosylase (UDG) cloning is a method for cloning PCR amplification products into cloning vectors (U.S. Pat. No. 5,334,515, entirely incorporated herein by reference). Briefly, PCR amplification of the desired DNA segment is performed with primers that contain uracil bases in place of thymidine bases in their 5' ends. When such PCR products are incubated with the enzyme UDG, the uracil bases are specifically removed. The loss of these bases weakens base pairing in the ends of the PCR product DNA, and when incubated at a suitable temperature (e.g., 37° C.), the ends of such products are largely single stranded. If such incubations are done in the presence of linear cloning vectors containing protruding 3' tails that are complementary to the 3' ends of the PCR products, base pairing efficiently anneals the PCR products to the cloning vector. When the annealed product is introduced into E. coli cells by transformation, in vivo processes efficiently convert it into a recombinant plasmid.

Figure 8C:
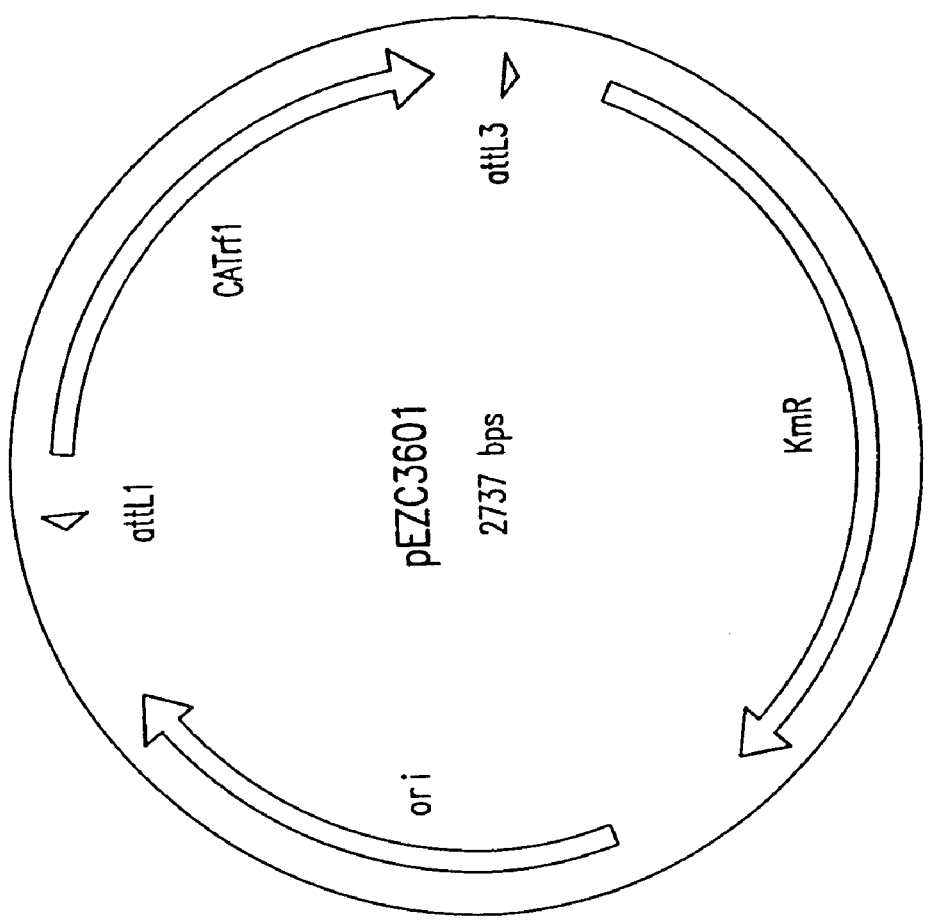
FIG. 8C depicts a vector diagram of pEZC3601.
Figure 8D:
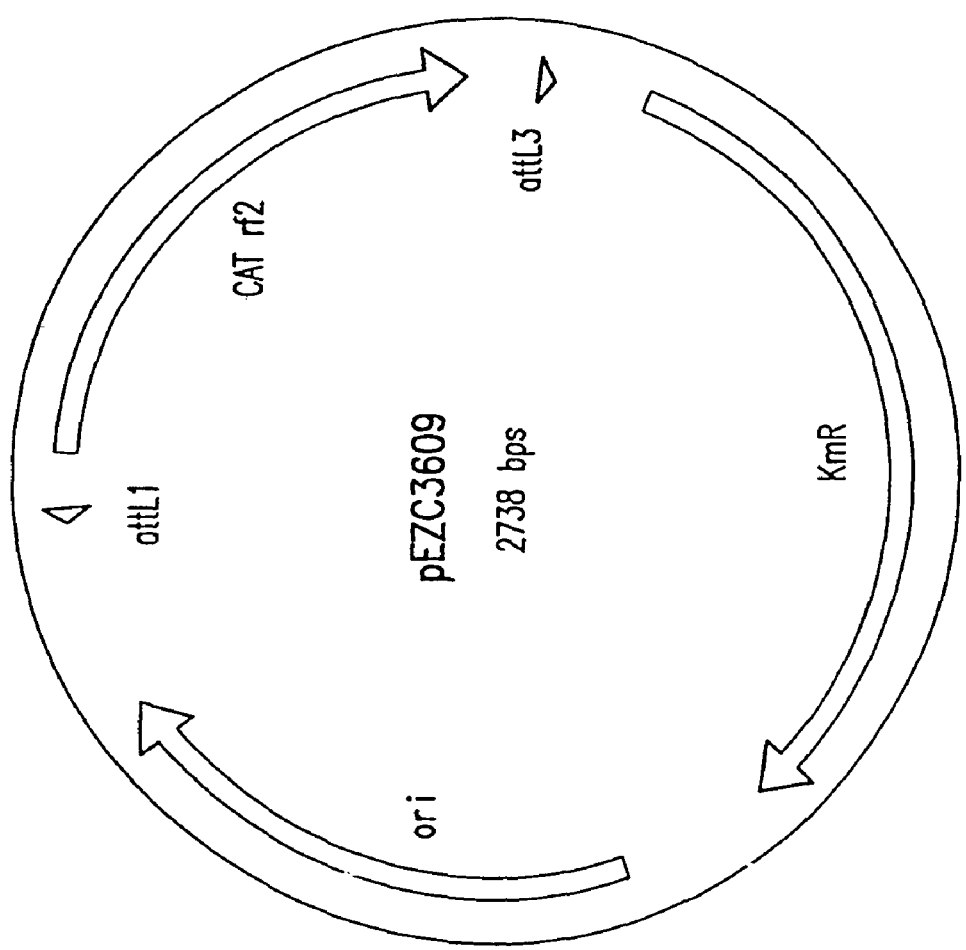
FIG. 8D depicts a vector diagram of pEZC3609.
Figure 8E:
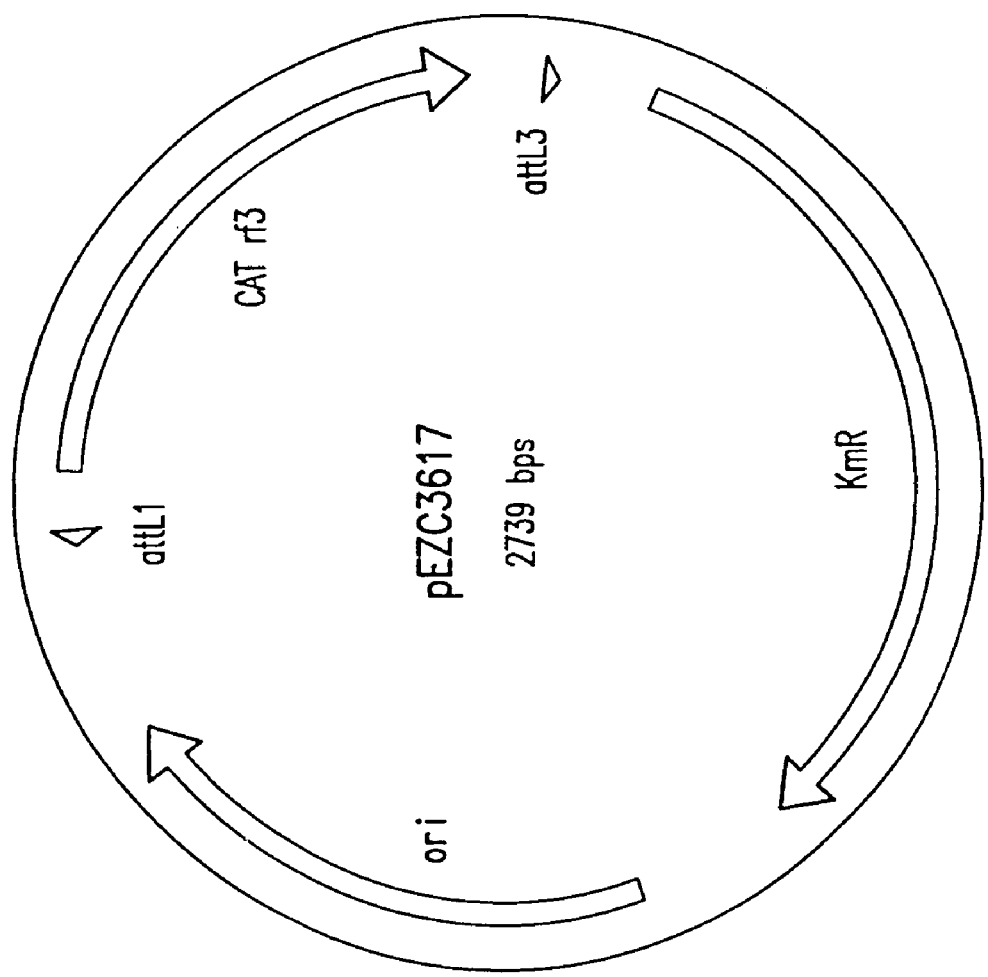
FIG. 8E depicts a vector diagram of pEZC3617.
Figure 8F:
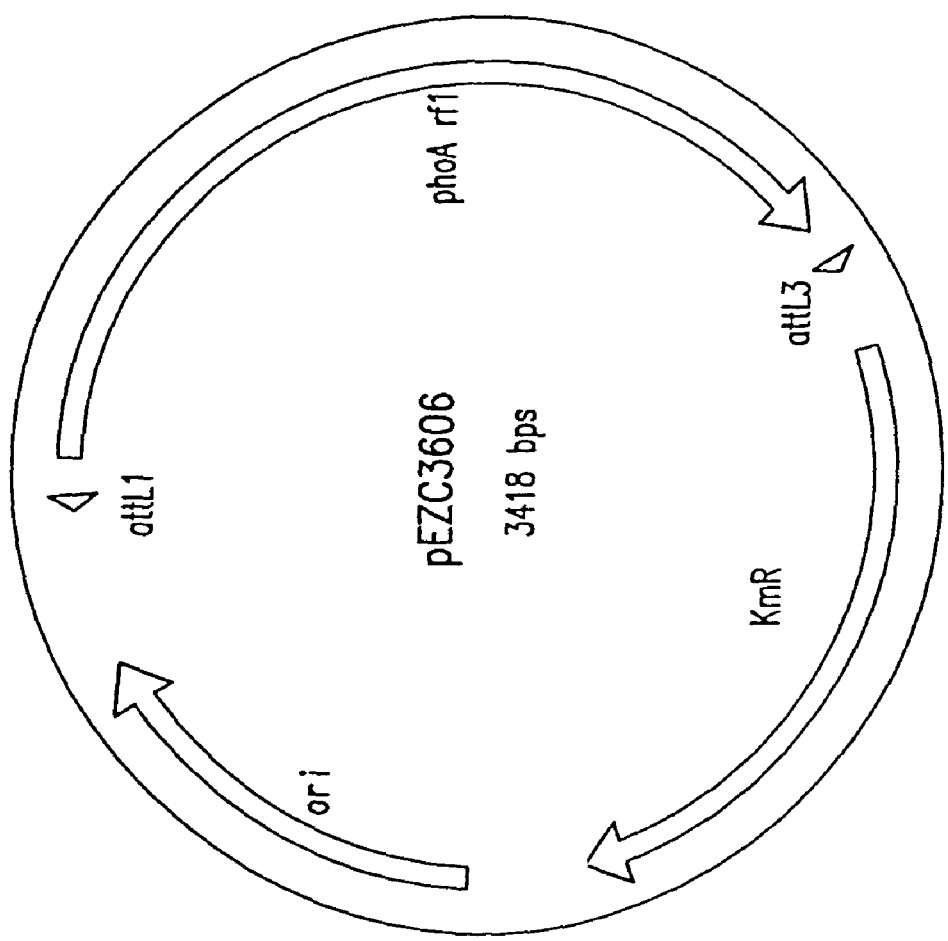
FIG. 8F depicts a vector diagram of pEZC3606.
Figure 8G:
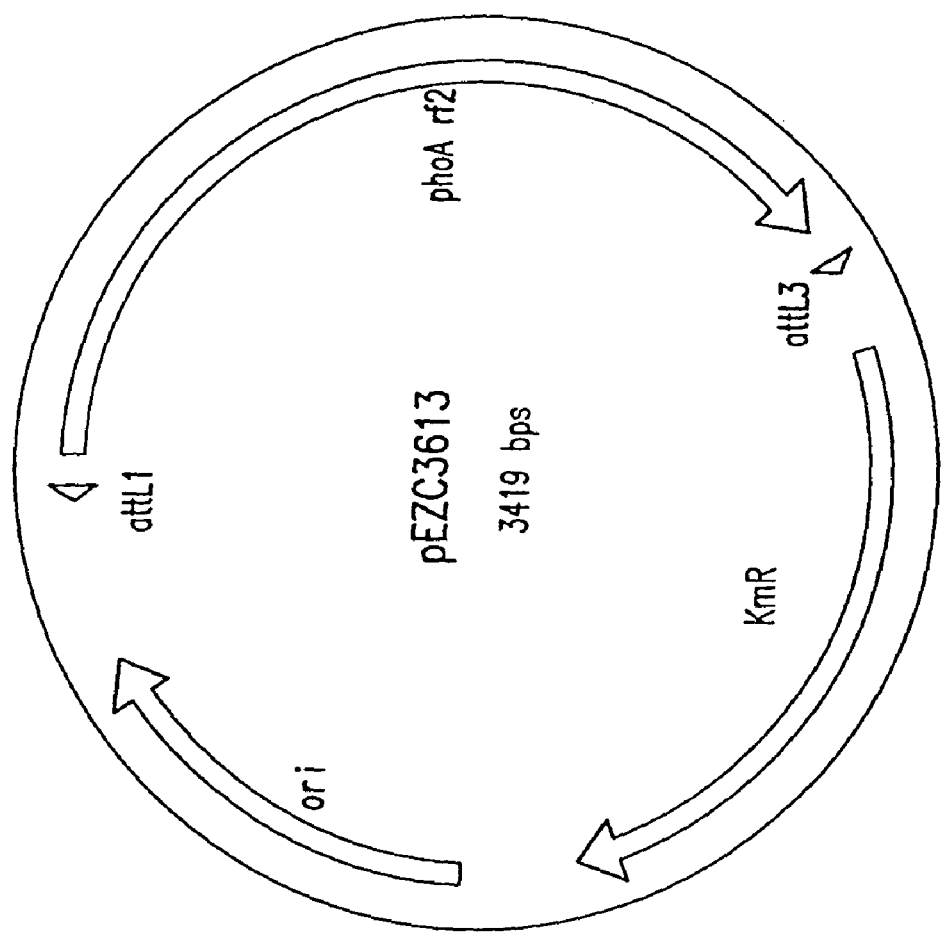
FIG. 8G depicts a vector diagram of pEZC3613.

UDG cloning vectors that enable cloning of any PCR product in all three reading frames were prepared from pEZC3201 (FIG. 8K) as follows. Eight oligonucleotides were obtained from Life Technologies, Inc. (all written 5'→3': rf1 top

```
rf1 top         (GGCC GAT TAC GAT ATC CCA ACG ACC GAA AAC CTG.TAT TTT CAG GGT)    (SEQ. ID NO:19), rf1 bottom      (CAG GTT TTC GGT CGT TGG GAT ATC GTA ATC)                          (SEQ. ID NO:20), rf2 top         (GGCCA GAT TAC GAT ATC CCA ACG ACC GAA AAC CTG TAT TTT CAG GGT)    (SEQ. ID NO:21), rf2 bottom      (CAG GTT TTC GGT CGT TGG GAT ATC GTA ATC T)                        (SEQ. ID NO:22), rf3 top         (GGCCAA GAT TAC GAT ATC CCA ACG ACC GAA AAC CTG TAT TTT CAG GGT)   (SEQ. ID NO:23), rf3 bottom      (CAG GTT TTC GGT CGT TGG GAT ATC GTA ATC TT)                       (SEQ. ID NO:24), carboxy top     (ACC GTT TAC GTG GAC)                                              (SEQ. ID NO:25) and carboxy bottom  (TCGA GTC CAC GTA AAC GGT TCC CAC TTA TTA)                         (SEQ. ID NO:26).
```

The rf1, 2, and 3 top strands and the carboxy bottom strand were phosphorylated on their 5' ends with T4 polynucleotide kinase, and then the complementary strands of each pair were hybridized. Plasmid pEZC3201 (FIG. 8K) was cut with Not I and Sal I, and aliquots of cut plasmid were mixed with the carboxy-oligo duplex (Sal I end) and either the rf1, rf2, or rf3 duplexes (Not I ends) (10 µg cut plasmid (about 5 pmol) mixed with 250 pmol carboxy oligo duplex, split into three 20 µl volumes, added 5 µl (250 pmol) of rf1, rf2, or rf3 duplex and 2 µl=2 units T4 DNA ligase to each reaction). After 90 minutes of ligation at room temperature, each reaction was applied to a preparative agarose gel and the 2.1 kb vector bands were eluted and dissolved in 50 µl of TE.

Part II: PCR of CAT and phoA Genes

Figure 8H:
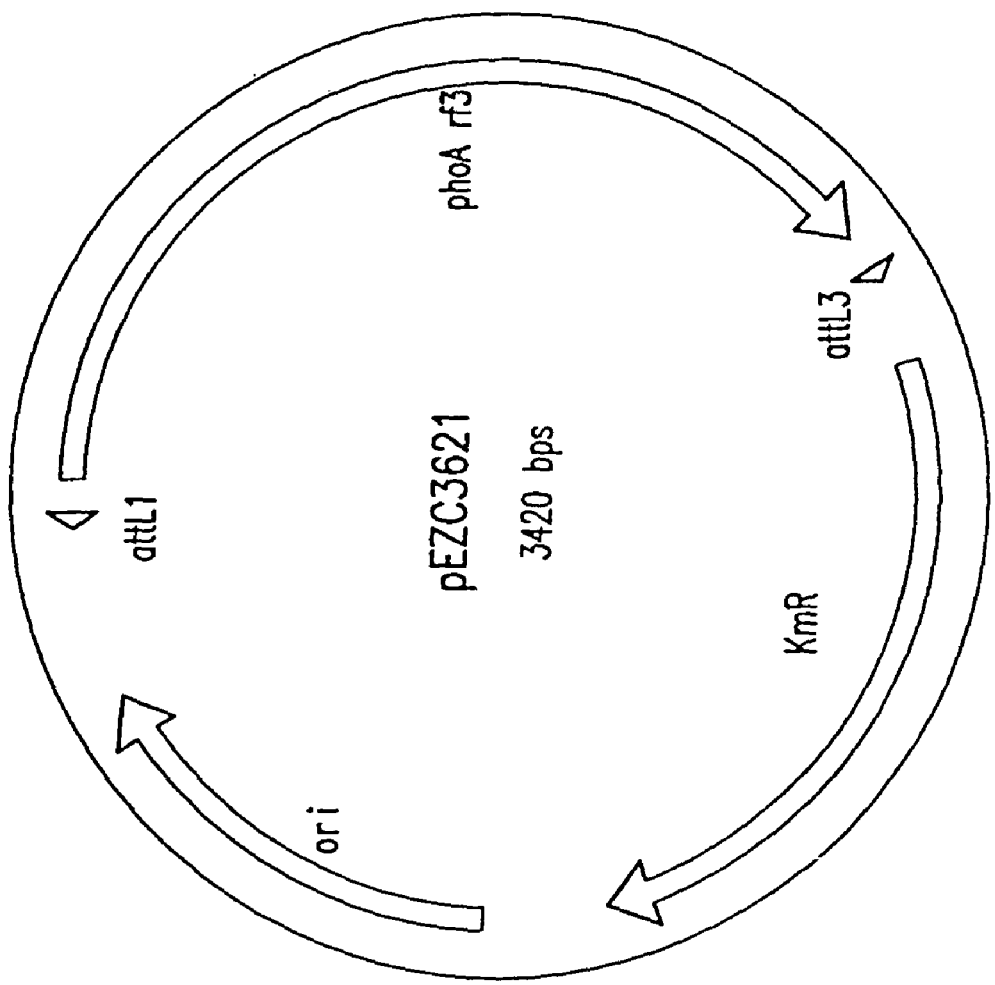
FIG. 8H depicts a vector diagram of pEZC3621.
Figure 8I:
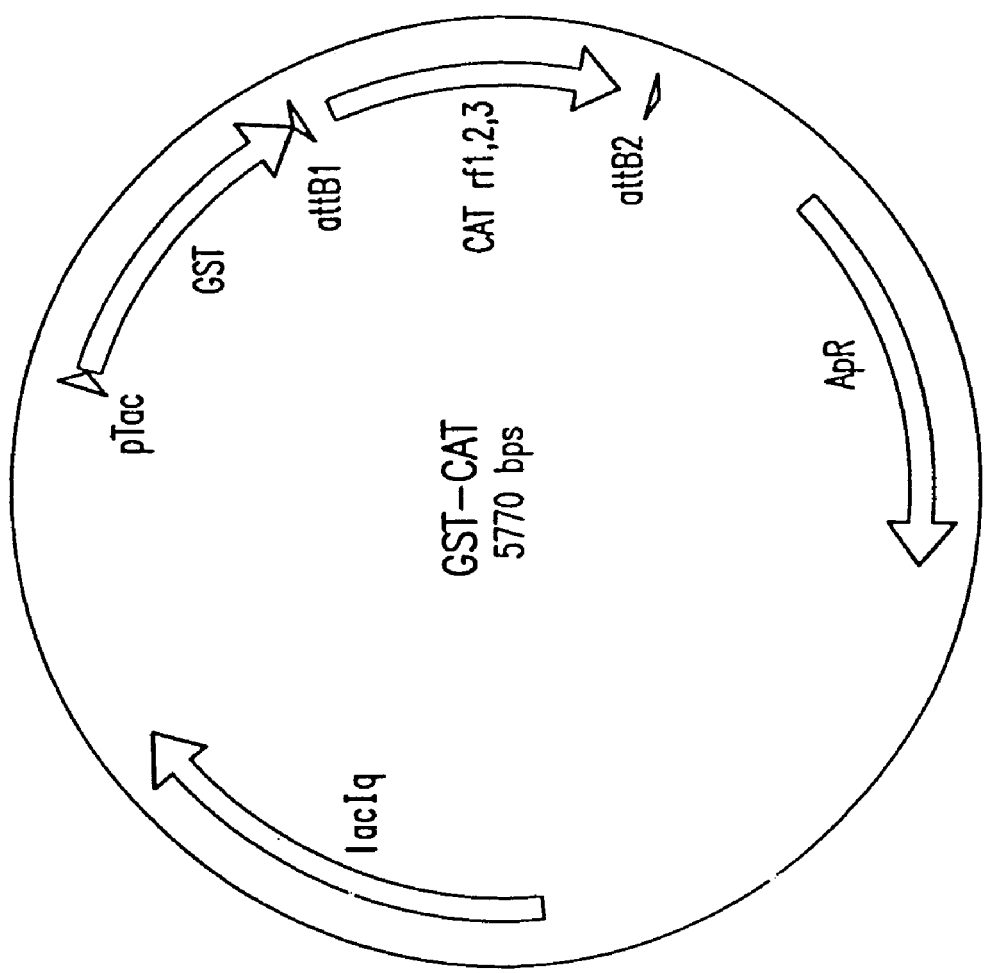
FIG. 8I depicts a vector diagram of GST-CAT.
Figure 8J:
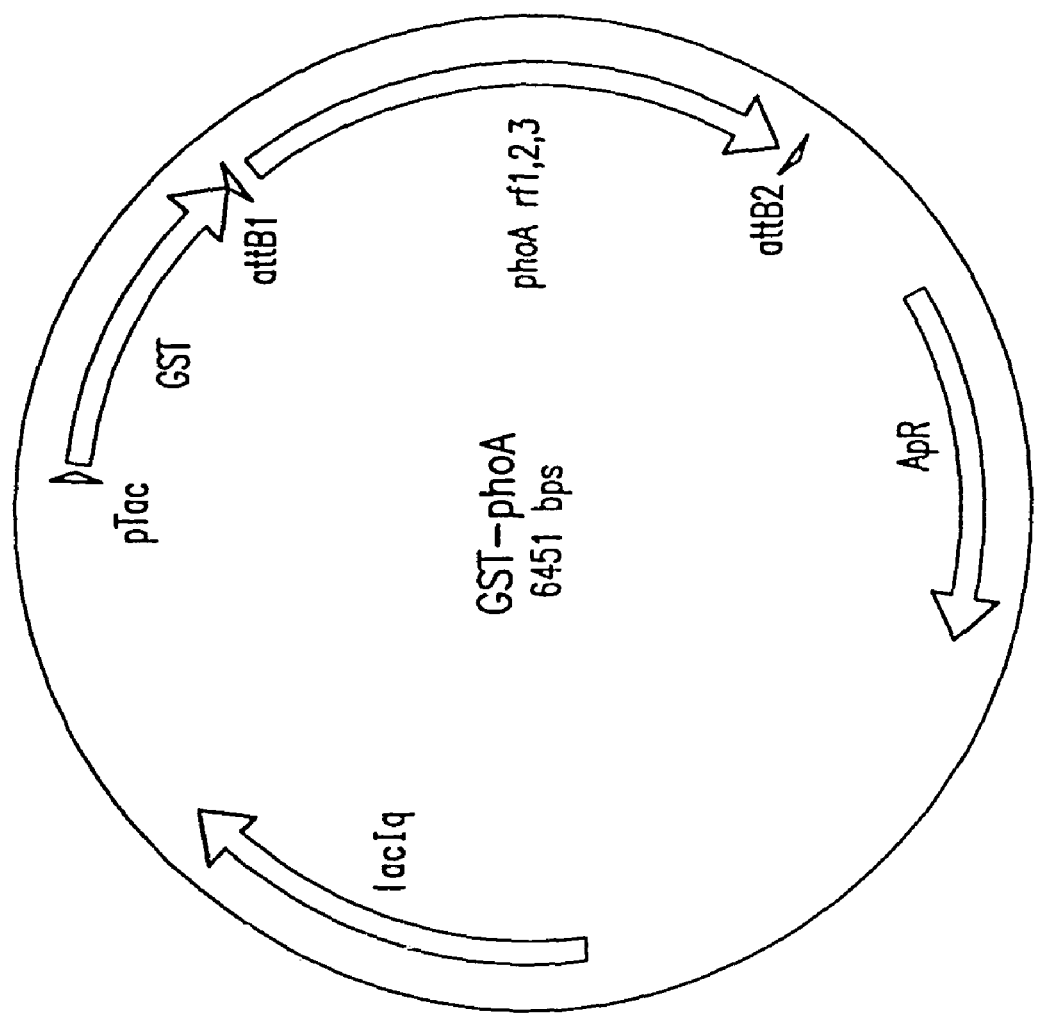
FIG. 8J depicts a vector diagram of GST-phoA.
Figure 8K:
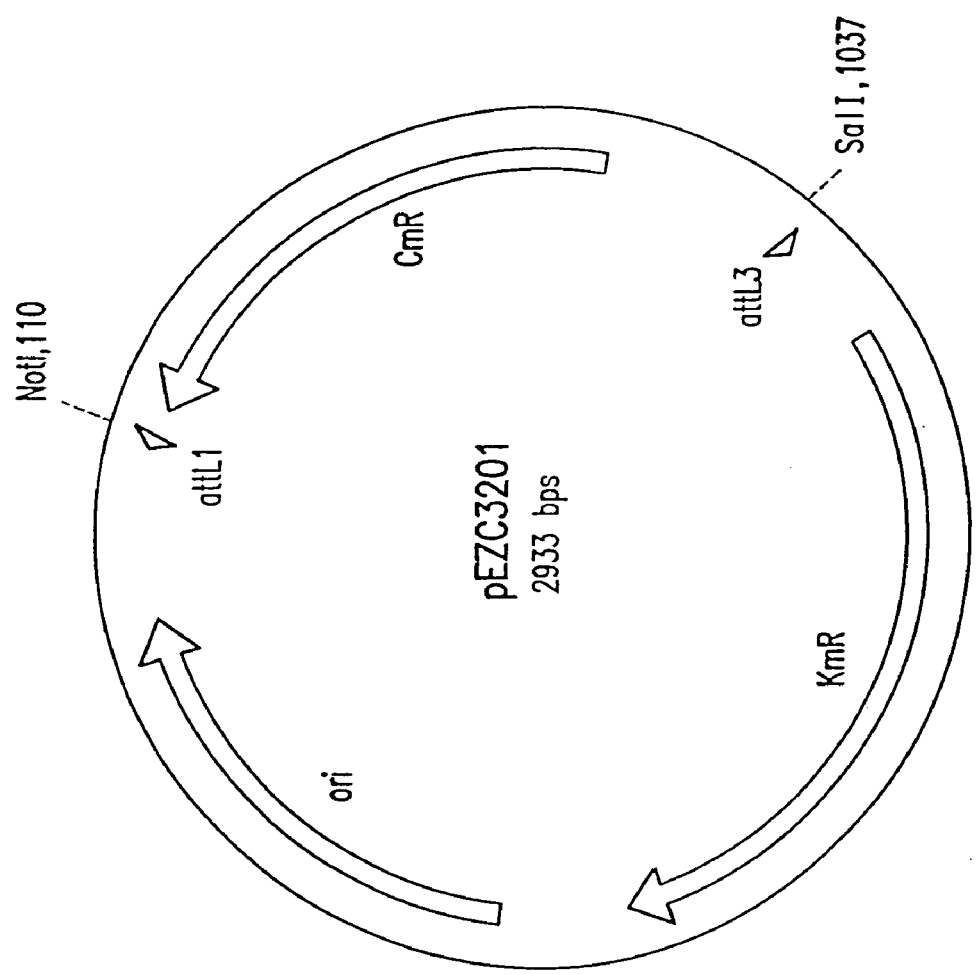
FIG. 8K depicts a vector diagram of pEZC3201.

Primers were obtained from Life Technologies, Inc., to amplify the chloramphenicol acetyl transferase (CAT) gene from plasmid pACYC184, and phoA, the alkaline phosphatase gene from E. coli. The primers had 12-base 5' extensions containing uracil bases, so that treatment of PCR products with uracil DNA glycosylase (UDG) would weaken base pairing at each end of the DNAs and allow the 3' strands to anneal with the protruding 3' ends of the rf1, 2, and 3 vectors described above. The sequences of the primers (all written 5'→3') were:

coli DH5α cells (LTI) and plated on agar containing 50 µg/ml kanamycin. Colonies were picked and analysis of miniprep DNA showed that the CAT gene had been cloned in reading frame 1 (pEZC3601)(FIG. 8C), reading frame 2 (pEZC3609)(FIG. 8D) and reading frame 3 (pEZC3617) (FIG. 8E), and that the phoA gene had been cloned in reading frame 1 (pEZC3606)(FIG. 8F), reading frame 2 (pEZC3613)(FIG. 8G) and reading frame 3 (pEZC3621) (FIG. 8H).

Part IV: Subcloning of CAT or phoA from UDG Cloning Vectors into a GST Fusion Vector Plasmids encoding fusions between GST and either CAT or phoA in all three reading frames were constructed by recombinational cloning as follows. Miniprep DNA of GST vector donor pEZC3501(FIG. 8B) (derived from Pharmacia plasmid pGEX-2TK as described above) was linearized with Cla I. About 5 ng of vector donor were mixed with about 10 ng each of the appropriate circular gene donor vectors containing CAT or phoA in 8 µl reactions containing buffer and recombination proteins Int, Xis, and IHF (above). After incubation, 1 µl of each reaction was transformed into E. coli strain DH5α and plated on ampicillin, as presented in Table 7.

```
CAT left,   UAU UUU CAG GGU ATG GAG AAA AAA ATC ACT GGA TAT ACC   (SEQ. ID NO:27);

CAT right,  UCC CAC UUA UUA CGC CCC GCC CTG CCA CTC ATC           (SEQ. ID NO:28);

phoA left,  UAU UUU CAG GGU ATG CCT GTT CTG GAA AAC CGG           (SEQ. ID NO:29); and phoA right, UCC CAC UUA UUA TTT CAG CCC CAG GGC GGC TTT C         (SEQ. ID NO:30).
```

The primers were then used for PCR reactions using known method steps (see, e.g., U.S. Pat. No. 5,334,515, entirely incorporated herein by reference), and the polymerase chain reaction amplification products obtained with these primers comprised the CAT or phoA genes with the initiating ATGs but without any transcriptional signals. In addition, the uracil-containing sequences on the amino termini encoded the cleavage site for TEV protease (Life Technologies, Inc, and those on the carboxy terminal encoded consecutive TAA nonsense codons.

Unpurified PCR products (about 30 ng) were mixed with the gel purified, linear rf1, rf2, or rf3 cloning vectors (about 50 ng) in a 10 µl reaction containing 1×REact 4 buffer (LTI) and 1 unit UDG (LTI). After 30 minutes at 37° C., 1 µl aliquots of each reaction were transformed into competent E.

TABLE 7

| DNA | Colonies (10% of each transformation) |
|---|---|
| Linear vector donor (pEZC3501/Cla) | 0 |
| Vector donor + CAT rf1 | 110 |
| Vector donor + CAT rf2 | 71 |
| Vector donor + CAT rf3 | 148 |
| Vector donor + phoA rf1 | 121 |
| Vector donor + phoA rf2 | 128 |
| Vector donor + phoA rf3 | 31 |

Part V: Expression of Fusion Proteins

Two colonies from each transformation were picked into 2 ml of rich medium (CIRCLEGROW® brand culture medium, Bio101 Inc.) in 17×100 mm plastic tubes (FAL-CON® brand plasticware, Cat. No. 2059, Becton Dickinson) containing 100 µg/ml ampicillin and shaken vigorously for about 4 hours at 37° C., at which time the cultures were visibly turbid. One ml of each culture was transferred to a new tube containing 10 µl of 10% (w/v) IPTG to induce expression of GST. After 2 hours additional incubation, all cultures had about the same turbidity; the A600 of one culture was 1.5. Cells from 0.35 ml each culture were harvested and treated with sample buffer (containing SDS and β-mercaptoethanol) and aliquots equivalent to about 0.15 A600 units of cells were applied to a Novex 4-20% gradient polyacrylamide gel. Following electrophoresis the gel was stained with Coomassie blue.

Results: Enhanced expression of single protein bands was seen for all 12 cultures. The observed sizes of these proteins correlated well with the sizes predicted for GST being fused (through attB recombination sites without stop codons) to CAT or phoA in three reading frames: CAT rf1=269 amino acids; CAT rf2=303 amino acids; CAT rf3=478 amino acids; phoA rf1=282 amino acids; phoA rf2=280 amino acids; and phoA rf3=705 amino acids.

Analysis: Both CAT and phoA genes were subcloned into a GST fusion vector in all three reading frames, and expression of the six fusion proteins was demonstrated.

While the foregoing invention has been described in some detail for purposes of clarity and understanding, it will be appreciated by one skilled in the art from a reading of this disclosure that various changes in form and detail can be made without departing from the true scope of the invention and appended claims. All patents and publications cited herein are entirely incorporated herein by reference.

What is claimed is:

1. A method of producing a nucleic acid molecule comprising:
   (a) providing a first nucleic acid molecule comprising at least a first promoter, a first positive selectable marker and at least a first recombination site;
   (b) providing a second nucleic acid molecule comprising
      (i) a second positive selectable marker, or portion thereof, which is not functional,
      (ii) a negative selection marker, and
      (iii) a second and a third recombination sites at least one of which will recombine with the first recombination site;
   (c) forming a mixture in vitro between the first and second nucleic acid molecules and at least one site specific recombination protein, under conditions sufficient to cause recombination in vitro between the first and second nucleic acid molecules, thereby producing a third nucleic acid molecule in which the first promoter and the second positive selectable marker, or portion thereof, are operably linked to form a functional second positive selectable marker; and
   (d) selecting for the nucleic acid molecules generated in step (c) which contain
      (i) either the first or second positive selection marker, and
      (ii) do not contain the negative selection marker.

2. The method of claim 1, wherein the first nucleic acid molecule further comprises an origin of replication.

3. The method of claim 1, wherein the second nucleic acid molecule further comprises one or more functional antibiotic resistance genes.

4. The method of claim 1, wherein the negative selection marker is a toxic gene.

5. The method of claim 1, wherein the first positive selectable marker is an antibiotic resistance gene.

6. The method of claim 1, wherein the second positive selectable marker, or portion thereof, is an antibiotic resistance gene selected from the group consisting of a chloramphenicol resistance gene, or a portion thereof; an ampicillin resistance gene, or a portion thereof; a methicillin resistance gene, or a portion thereof; a tetracycline resistance gene, or a portion thereof and a kanamycin resistance gene, or a portion thereof.

7. The method of claim 1, wherein the second positive selectable marker, or portion thereof, is a chloramphenicol resistance gene, or a portion thereof.

8. The method of claim 1, wherein the first and second and third recombination sites are selected from the group consisting of lox sites, att sites, and mutants thereof.

9. The method of claim 1, wherein the first and second and third recombination sites are selected from the group consisting of lox sites and att sites.

10. The method of claim 1, wherein the first and second and third recombination sites are lox sites.

11. The method of claim 10, wherein the lox sites are loxP sites.

12. The method of claim 1, wherein the first promoter is located immediately adjacent to the first recombination site.

13. The method of claim 1, wherein the second positive selectable marker, or portion thereof, is located immediately adjacent to the second recombination site.

14. The method of claim 1, wherein the at least one site-specific recombination protein is selected from the group consisting of Cre, Int, IHF, Xis, FLP, γδ, Tn3 resolvase, Hin, Gin, Cin and combinations thereof.

15. The method of claim 1, wherein the at least one site-specific recombination protein is Cre.

16. The method of claim 1, wherein the at least one site-specific recombination protein is selected from the group consisting of Int, IHF and Xis.

17. The method of claim 1, wherein the first nucleic acid molecule or the second nucleic acid molecule or the third nucleic acid molecule is a vector.

18. The method of claim 1, wherein the first nucleic acid molecule or the second nucleic acid molecule is linear.

19. The method of claim 1, further comprising contacting at least one host cell with the mixture, and selecting for a host cell comprising the third nucleic acid molecule.

20. The method of claim 1, further comprising introducing the third nucleic acid molecule into a host cell.

21. The method of claim 1, further comprising introducing the third nucleic acid molecule into a host cell and expressing the second positive selectable marker, or portion thereof.

22. The method of claim 4, wherein the toxic gene is a restriction enzyme.

23. The method of claim 22, wherein the restriction enzyme is DpnI.

24. The method of claim 1, wherein the first and second recombination sites are att sites.

25. The method of claim 11, wherein the att sites are selected from the group consisting of attB sites, attP sites, attL sites and attR sites.

26. The method of claim 17, wherein the vector is an expression vector.

27. The method of claim 19, further comprising selecting against a host cell comprising the first or the second nucleic acid molecule.

28. The method of claim 19, further comprising selecting against a host cell comprising the first and the second nucleic acid molecule.

29. The method of claim 19, wherein the host cell is a prokaryotic cell.

30. The method of claim 19, wherein the host cell is a bacterial cell.

31. The method of claim 19, wherein the host cell is an *Escherichia coli* cell.

32. The method of claim 21, wherein the host cell is an *Escherichia coli* cell.

* * * * *

SEQUENCE LISTING

```
(1) GENERAL INFORMATION:

(iii) NUMBER OF SEQUENCES: 35

(2) INFORMATION FOR SEQ ID NO: 1:

(i) SEQUENCE CHARACTERISTICS:
       (A) LENGTH: 25 base pairs
       (B) TYPE: nucleic acid
       (C) STRANDEDNESS: both
       (D) TOPOLOGY: both (ii) MOLECULE TYPE: cDNA (xi) SEQUENCE DESCRIPTION: SEQ ID NO: 1:

RKYCWGCTTT YKTRTACNAA STSGB                                              25

(2) INFORMATION FOR SEQ ID NO: 2:

(i) SEQUENCE CHARACTERISTICS:
       (A) LENGTH: 25 base pairs
       (B) TYPE: nucleic acid
       (C) STRANDEDNESS: both
       (D) TOPOLOGY: both (ii) MOLECULE TYPE: cDNA (xi) SEQUENCE DESCRIPTION: SEQ ID NO: 2:

AGCCWGCTTT YKTRTACNAA CTSGB                                              25

(2) INFORMATION FOR SEQ ID NO: 3:

(i) SEQUENCE CHARACTERISTICS:
       (A) LENGTH: 25 base pairs
       (B) TYPE: nucleic acid
       (C) STRANDEDNESS: both
       (D) TOPOLOGY: both (ii) MOLECULE TYPE: cDNA (xi) SEQUENCE DESCRIPTION: SEQ ID NO: 3:

GTTCAGCTTT CKTRTACNAA CTSGB                                              25

(2) INFORMATION FOR SEQ ID NO: 4:

(i) SEQUENCE CHARACTERISTICS:
       (A) LENGTH: 25 base pairs
       (B) TYPE: nucleic acid
```

(C) STRANDEDNESS: both
        (D) TOPOLOGY: both (ii) MOLECULE TYPE: cDNA (xi) SEQUENCE DESCRIPTION: SEQ ID NO: 4:

AGCCWGCTTT CKTRTACNAA GTSGB                                              25

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 5:

GTTCAGCTTT YKTRTACNAA GTSGB                                              25

(2) INFORMATION FOR SEQ ID NO: 6:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 6:

AGCCTGCTTT TTTGTACAAA CTTGT                                              25

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 7:

AGCCTGCTTT CTTGTACAAA CTTGT                                              25

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 8:

ACCCAGCTTT CTTGTACAAA CTTGT                                              25

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 9:

GTTCAGCTTT TTTGTACAAA CTTGT                                      25

(2) INFORMATION FOR SEQ ID NO: 10:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 10:

GTTCAGCTTT CTTGTACAAA CTTGT                                      25

(2) INFORMATION FOR SEQ ID NO: 11:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 11:

GTTCAGCTTT CTTGTACAAA GTTGG                                      25

(2) INFORMATION FOR SEQ ID NO: 12:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 12:

AGCCTGCTTT TTTGTACAAA GTTGG                                      25

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 13:

AGCCTGCTTT CTTGTACAAA GTTGG                                      25

(2) INFORMATION FOR SEQ ID NO: 14:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 14:

ACCCAGCTTT CTTGTACAAA GTTGG                                      25

-continued (2) INFORMATION FOR SEQ ID NO: 15:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 15:

GTTCAGCTTT TTTGTACAAA GTTGG                                25

(2) INFORMATION FOR SEQ ID NO: 16:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 16:

GTTCAGCTTT CTTGTACAAA GTTGG                                25

(2) INFORMATION FOR SEQ ID NO: 17:

(i) SEQUENCE CHARACTERISTICS:
        (A) LENGTH: 39 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 17:

CCACCACAAA CGCGTCCATG GAATTACACT TTAATTTAG                    39

(2) INFORMATION FOR SEQ ID NO: 18:

(i) SEQUENCE CHARACTERISTICS:
        (A) LENGTH: 39 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 18:

CCACCACAAG TCGACGCATG CCGACAGCCT TCCAAATGT                    39

(2) INFORMATION FOR SEQ ID NO: 19:

(i) SEQUENCE CHARACTERISTICS:
        (A) LENGTH: 46 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 19:

GGCCGATTAC GATATCCCAA CGACCGAAAA CCTGTATTTT CAGGGT            46

(2) INFORMATION FOR SEQ ID NO: 20:

(i) SEQUENCE CHARACTERISTICS:
              (A) LENGTH: 30 base pairs
              (B) TYPE: nucleic acid
              (C) STRANDEDNESS: both
              (D) TOPOLOGY: both (ii) MOLECULE TYPE: cDNA (xi) SEQUENCE DESCRIPTION: SEQ ID NO: 20:

CAGGTTTTCG GTCGTTGGGA TATCGTAATC                                            30

(2) INFORMATION FOR SEQ ID NO: 21:

(i) SEQUENCE CHARACTERISTICS:
              (A) LENGTH: 47 base pairs
              (B) TYPE: nucleic acid
              (C) STRANDEDNESS: both
              (D) TOPOLOGY: both (ii) MOLECULE TYPE: cDNA (xi) SEQUENCE DESCRIPTION: SEQ ID NO: 21:

GGCCAGATTA CGATATCCCA ACGACCGAAA ACCTGTATTT TCAGGGT                         47

(2) INFORMATION FOR SEQ ID NO: 22:

(i) SEQUENCE CHARACTERISTICS:
              (A) LENGTH: 31 base pairs
              (B) TYPE: nucleic acid
              (C) STRANDEDNESS: both
              (D) TOPOLOGY: both (ii) MOLECULE TYPE: cDNA (xi) SEQUENCE DESCRIPTION: SEQ ID NO: 22:

CAGGTTTTCG GTCGTTGGGA TATCGTAATC T                                          31

(2) INFORMATION FOR SEQ ID NO: 23:

(i) SEQUENCE CHARACTERISTICS:
              (A) LENGTH: 48 base pairs
              (B) TYPE: nucleic acid
              (C) STRANDEDNESS: both
              (D) TOPOLOGY: both (ii) MOLECULE TYPE: cDNA (xi) SEQUENCE DESCRIPTION: SEQ ID NO: 23:

GGCCAAGATT ACGATATCCC AACGACCGAA AACCTGTATT TTCAGGGT                        48

(2) INFORMATION FOR SEQ ID NO: 24:

(i) SEQUENCE CHARACTERISTICS:
              (A) LENGTH: 32 base pairs
              (B) TYPE: nucleic acid
              (C) STRANDEDNESS: both
              (D) TOPOLOGY: both (ii) MOLECULE TYPE: cDNA (xi) SEQUENCE DESCRIPTION: SEQ ID NO: 24:

CAGGTTTTCG GTCGTTGGGA TATCGTAATC TT                                         32

(2) INFORMATION FOR SEQ ID NO: 25:

(i) SEQUENCE CHARACTERISTICS:
              (A) LENGTH: 15 base pairs
              (B) TYPE: nucleic acid
              (C) STRANDEDNESS: both (D) TOPOLOGY: both (ii) MOLECULE TYPE: cDNA (xi) SEQUENCE DESCRIPTION: SEQ ID NO: 25:

ACCGTTTACG TGGAC                                                          15

(2) INFORMATION FOR SEQ ID NO: 26:

(i) SEQUENCE CHARACTERISTICS:
            (A) LENGTH: 31 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO: 26:

TCGAGTCCAC GTAAACGGTT CCCACTTATT A                                        31

(2) INFORMATION FOR SEQ ID NO: 27:

(i) SEQUENCE CHARACTERISTICS:
            (A) LENGTH: 39 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO: 27:

UAUUUUCAGG GUATGGAGAA AAAAATCACT GGATATACC                                 39

(2) INFORMATION FOR SEQ ID NO: 28:

(i) SEQUENCE CHARACTERISTICS:
            (A) LENGTH: 33 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO: 28:

UCCCACUUAU UACGCCCCGC CCTGCCACTC ATC                                      33

(2) INFORMATION FOR SEQ ID NO: 29:

(i) SEQUENCE CHARACTERISTICS:
            (A) LENGTH: 33 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO: 29:

UAUUUUCAGG GUATGCCTGT TCTGGAAAAC CGG                                      33

(2) INFORMATION FOR SEQ ID NO: 30:

(i) SEQUENCE CHARACTERISTICS:
            (A) LENGTH: 34 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO: 30:

UCCCACUUAU UAUUUCAGCC CCAGGGCGGC TTTC                          34

(2) INFORMATION FOR SEQ ID NO: 31:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 31:

AGCCTGCTTT TTTATACTAA CTTGA                                    25

(2) INFORMATION FOR SEQ ID NO: 32:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 32:

TCAAGTTAGT ATAAAAAAGC AGGCT                                    25

(2) INFORMATION FOR SEQ ID NO: 33:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 33:

ACAAGTTTGT ACAAAAAAGC AGGCT                                    25

(2) INFORMATION FOR SEQ ID NO: 34:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 34:

ACAAGTTTGT ACAAGAAAGC AGGCT                                    25

(2) INFORMATION FOR SEQ ID NO: 35:

(i) SEQUENCE CHARACTERISTICS:
        (A) LENGTH: 25 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 35:

ACCACTTTGT ACAAGAAAGC TGGGT                                    25